US008911421B2

(12) United States Patent
Domkowski et al.

(10) Patent No.: US 8,911,421 B2
(45) **Date of Patent: *Dec. 16, 2014**

(54) SYSTEM AND METHOD FOR MIXING THE CONTENTS OF TWO CONTAINERS

(71) Applicant: Hospira, Inc., Lake Forest, IL (US)

(72) Inventors: John A. Domkowski, Kenosha, WI (US); David L. Foshee, Apex, NC (US); Theodore J. Mosler, Raleigh, NC (US); Edward Browka, Chapel Hill, NC (US)

(73) Assignee: Hospira, Inc., Lake Forest, IL (US)

( * ) Notice: Subject to any disclaimer, the term of this patent is extended or adjusted under 35 U.S.C. 154(b) by 41 days.

This patent is subject to a terminal disclaimer.

(21) Appl. No.: 13/573,732

(22) Filed: Oct. 3, 2012

(65) Prior Publication Data

US 2013/0102990 A1 Apr. 25, 2013

Related U.S. Application Data

(60) Provisional application No. 61/542,534, filed on Oct. 3, 2011.

(51) Int. Cl.

*A61M 5/32* (2006.01)
*B65D 25/20* (2006.01)
*A61J 1/14* (2006.01)
*A61J 1/10* (2006.01)
*A61J 1/20* (2006.01)

(52) U.S. Cl.

CPC ............... *B65D 25/20* (2013.01); *A61J 1/1462* (2013.01); *A61J 2001/2041* (2013.01); *A61J 2001/2068* (2013.01); *A61J 1/10* (2013.01); *A61J 2001/201* (2013.01); *A61J 1/2089* (2013.01)

USPC ............ 604/416; 604/403; 604/415; 604/408

(58) Field of Classification Search

CPC ................. A61J 1/10; A61J 1/12; A61J 1/14; A61J 1/1406–1/1437; A61J 2001/2003; A61J 2001/2006; A61J 2001/2048

USPC .................................................. 604/403–416

See application file for complete search history.

(56) References Cited

U.S. PATENT DOCUMENTS 2,176,923 A 10/1939 Nitardy
2,372,181 A 3/1945 Barr (Continued)

FOREIGN PATENT DOCUMENTS

DE 297 21 872 3/1998
EP 0 335 378 10/1989

(Continued)

OTHER PUBLICATIONS

"Special 510(k) Premarket Notification—addEASE 20mm Binary Connector with 17 Ga. Needle," B. Braun Medical, Inc., Mar. 27, 2009. Describing the B. Braun addEASE Connector.

(Continued)

*Primary Examiner* — Philip R Wiest
*Assistant Examiner* — Benjamin Klein
(74) *Attorney, Agent, or Firm* — Brian R. Woodworth

(57) ABSTRACT

A system for mixing the contents of a first container and a second container. The system includes the first container that has container body with an opening fluidly connected to a cavity defined by the container body, a first substance contained in the cavity, and a stopper sealing the opening. The second container includes a port assembly including a port housing connected to the second container and a retainer constructed to connect to the first container. The retainer is configured to rotate and move axially relative to the port housing, wherein relative rotation between the port housing and the retainer causes the retainer to move axially relative to the port housing. The port assembly further includes an axially fixed actuator constructed to force the stopper into the first container when the retainer is rotated relative to the port housing.

19 Claims, 43 Drawing Sheets

(56) References Cited

U.S. PATENT DOCUMENTS 3,290,017 A 12/1966 Davies et al.
3,464,414 A 9/1969 Sponnoble
3,532,254 A 10/1970 Burke et al.
3,857,392 A 12/1974 Ogle
3,872,992 A 3/1975 Larson
4,089,432 A 5/1978 Crankshaw et al.
4,102,451 A 7/1978 Clarke et al.
4,123,091 A 10/1978 Cosentino et al.
4,185,747 A 1/1980 Goncalves
4,194,640 A 3/1980 Crankshaw et al.
4,226,334 A 10/1980 Weiler et al.
4,333,505 A 6/1982 Jones et al.
4,394,922 A 7/1983 Wimmer
4,444,330 A 4/1984 Kasai et al.
4,458,811 A 7/1984 Wilkinson
4,488,656 A 12/1984 Fukuoka et al.
4,526,572 A 7/1985 Donnan et al.
4,544,074 A 10/1985 Evans
4,610,684 A 9/1986 Knox et al.
4,614,267 A 9/1986 Larkin
4,614,515 A 9/1986 Tripp et al.
4,703,864 A 11/1987 Larkin et al.
4,757,911 A 7/1988 Larkin et al.
4,759,756 A 7/1988 Forman et al.
4,770,445 A 9/1988 Steer et al.
4,781,679 A 11/1988 Larkin
4,784,259 A 11/1988 Grabenkort
4,784,658 A * 11/1988 Grabenkort .................. 604/410
4,871,354 A 10/1989 Conn et al.
4,871,654 A 10/1989 Vanmaele et al.
4,936,445 A 6/1990 Grabenkort
4,936,841 A 6/1990 Aoki et al.
4,948,000 A 8/1990 Grabenkort
4,963,441 A 10/1990 Takai et al.
4,998,671 A 3/1991 Lefheit
5,060,812 A 10/1991 Ogle, II
5,064,059 A 11/1991 Ziegler et al.
5,066,280 A 11/1991 Braithwaite
5,066,286 A 11/1991 Ryan
5,088,994 A 2/1992 Porat et al.
5,102,408 A 4/1992 Hamacher
5,139,483 A 8/1992 Ryan
5,176,526 A 1/1993 Hillbish et al.
5,195,994 A 3/1993 Dieringer
5,222,486 A 6/1993 Vaughn
5,290,222 A 3/1994 Feng et al.
5,292,308 A 3/1994 Ryan
5,332,399 A 7/1994 Grabenkort et al.
5,335,773 A 8/1994 Haber et al.
5,358,501 A 10/1994 Meyer
5,380,315 A 1/1995 Isono et al.
5,409,141 A 4/1995 Kikuchi et al.
5,423,793 A 6/1995 Isono et al.
5,462,526 A 10/1995 Barney et al.
5,478,337 A 12/1995 Okamoto et al.
5,526,853 A 6/1996 McPhee et al.
5,527,580 A 6/1996 Ikeda et al.
5,545,152 A 8/1996 Funderburk et al.
5,620,427 A 4/1997 Werschmidt et al.
5,785,701 A 7/1998 Sams et al.
5,855,568 A 1/1999 Battiato et al.
5,928,213 A 7/1999 Barney et al.
5,944,709 A 8/1999 Barney et al.
5,947,954 A 9/1999 Bonaldo
5,989,237 A 11/1999 Fowles et al.
6,004,297 A 12/1999 Steenfeldt-Jensen et al.
6,063,068 A 5/2000 Fowles et al.
6,071,270 A 6/2000 Fowles et al.
6,096,024 A 8/2000 Graves et al.
6,113,583 A 9/2000 Fowles et al.
6,159,192 A 12/2000 Fowles et al.
6,203,535 B1 3/2001 Barney et al.
6,258,078 B1 7/2001 Thilly
6,413,242 B1 7/2002 Michel et al.
6,610,040 B1 8/2003 Fowles et al.
6,729,370 B2 5/2004 Norton et al.
6,846,305 B2 1/2005 Smith et al.
6,874,522 B2 4/2005 Anderson et al.
6,910,573 B2 6/2005 Deans
6,913,595 B2 7/2005 Mastorakis
6,957,745 B2 10/2005 Thibault et al.
6,962,321 B1 11/2005 Savage et al.
7,115,117 B2 10/2006 Shiraishi et al.
7,316,679 B2 1/2008 Bierman
7,347,458 B2 3/2008 Rome et al.
7,473,246 B2 1/2009 Vancaillie et al.
7,497,484 B2 3/2009 Ziman
7,540,863 B2 6/2009 Haindl
7,544,191 B2 6/2009 Peluso et al.
7,600,515 B2 10/2009 Matlock
7,615,041 B2 11/2009 Sullivan et al.
7,862,539 B2 1/2011 Knight
7,938,815 B2 5/2011 Shoji et al.
7,998,134 B2 8/2011 Fangrow et al.
8,075,545 B2 12/2011 Moy et al.
8,162,013 B2 * 4/2012 Rosenquist et al. .......... 141/384
8,216,207 B2 7/2012 Moy et al.
8,221,382 B2 7/2012 Moy et al.
8,241,265 B2 8/2012 Moy et al.
8,512,309 B2 8/2013 Shemesh et al.
8,721,612 B2 5/2014 Domkowski et al.
8,801,689 B2 8/2014 Moy et al.
2002/0082581 A1 6/2002 Di Giovanni et al.
2003/0105448 A1 6/2003 Shiraishi et al.
2003/0106610 A1 6/2003 Roos et al.
2003/0187420 A1 10/2003 Akerlund et al.
2003/0201641 A1 10/2003 Guest
2004/0186457 A1 9/2004 Truitt et al.
2004/0201216 A1 10/2004 Segal et al.
2005/0015075 A1 1/2005 Wright et al.
2005/0045669 A1 3/2005 Thunberg et al.
2005/0055008 A1 3/2005 Paradis et al.
2006/0030832 A1 2/2006 Niedospial et al.
2006/0282061 A1 12/2006 Domkowski et al.
2007/0088315 A1 4/2007 Haindl
2007/0102393 A1 5/2007 Colin et al.
2009/0032489 A1 2/2009 Moy et al.
2009/0036861 A1 2/2009 Moy et al.
2009/0036864 A1 2/2009 Moy et al.
2009/0036865 A1 * 2/2009 Moy et al. ..................... 604/416
2009/0036866 A1 2/2009 Moy et al.
2009/0069783 A1 3/2009 Ellstrom et al.
2009/0259197 A1 10/2009 Christiansen
2009/0270832 A1 10/2009 Vancaillie et al.
2010/0148500 A1 6/2010 Uehara et al.
2010/0152669 A1 6/2010 Rosenquist
2010/0211019 A1 8/2010 Greco
2010/0241088 A1 9/2010 Ranalletta et al.
2011/0015580 A1 1/2011 Stroup et al.
2011/0125128 A1 5/2011 Nord et al.
2011/0137294 A1 6/2011 Calimeri et al.
2011/0193004 A1 8/2011 Lahaye
2012/0136317 A1 5/2012 Teucher et al.
2013/0102990 A1 4/2013 Domkowski
2013/0102991 A1 4/2013 Domkowski
2013/0102992 A1 4/2013 Domkowski
2013/0199643 A1 8/2013 Domkowski
2014/0001063 A1 1/2014 Moy et al.
2014/0005629 A1 1/2014 Moy et al.

FOREIGN PATENT DOCUMENTS

EP 0 633 038 1/1995
EP 0 503 867 2/1997
FR 2931363 11/2009
FR 2952873 5/2011
GB 1419061 12/1975
JP 8243171 9/1996
JP 10024088 1/1998
JP 2002017871 1/2002
JP 2003-200977 7/2003
JP 2007236567 9/2007
JP 2007295998 11/2007
WO 98/14163 4/1998

(56) References Cited

FOREIGN PATENT DOCUMENTS

| | | |
|---|---|---|
| WO | 2008/115102 | 9/1998 |
| WO | 98/44257 | 10/1998 |
| WO | 00/66921 | 11/2000 |
| WO | 01/23026 | 4/2001 |
| WO | 2009/024807 | 2/2009 |
| WO | 2009/035383 | 3/2009 |
| WO | 2010/069361 | 6/2010 |

OTHER PUBLICATIONS

"addEASE Binary Connector with 17 Ga. Needle," B. Braun Medical Inc., 2011. Describing the B. Braun addEASE Connector.

"B. Braun addEASE Binary Connector," Medical Device Recalls, U.S. Food and Drug Administration, Jun. 24, 2010. Describing the B. Braun addEASE Connector.

Extended European Search Report for EP10160160.7 including concise summary of DE 297 21 872 (Oct. 6, 2010).

* cited by examiner

SYSTEM AND METHOD FOR MIXING THE CONTENTS OF TWO CONTAINERS

CROSS-REFERENCE TO RELATED APPLICATIONS

This application claims the benefit of U.S. Provisional Patent Application No. 61/542,534, filed on Oct. 3, 2011, and titled "System and Method for Mixing the Contents of Two Containers," which is incorporated herein by reference in its entirety.

FIELD OF THE INVENTION

This invention relates generally to a system and method for mixing the contents of two separate containers. The system avoids discharge of the contents and mixture into the environment while maintaining their sterility.

BACKGROUND OF THE INVENTION

Many compounds for medical use are packaged separately from the diluents used to reconstitute or dilute them, and facilitate their intravenous or subcutaneous delivery to a patient. These medical compounds are packaged in a variety of known pharmaceutical containers (e.g., vials) in solid form (e.g., lyophilized or spray-dried), liquid form, and other forms. Prior to administration of these compounds to a patient, the compounds are mixed with the diluents. If desired, the diluents can contain additional active compounds.

In order to mix a compound with a diluent, it is desirable to provide a system for mixing the compound and diluent that does not expose the compound, diluent, or resulting mixture to the external environment prior to and during mixing. Such exposure could negatively affect the sterility of the mixture, or, in the case of hazardous compounds, could place the user (e.g., a healthcare worker) in danger by exposing them to the hazardous compounds.

Systems for facilitating the safe transfer and mixing of medical compounds and diluents stored in separate containers are known. For example, a system involving the packaging of a medicament and a diluent in separate containers, which may be connected to one another at the time of use for convenient and safe mixing of the medicament and diluent in a sterile environment is currently sold by Hospira, Inc. (Lake Forest, Ill.) under the trademark ADD-VANTAGE®. The ADD-VANTAGE® system is described in U.S. Pat. Nos. 4,703,864; 4,757,911; 4,784,259; 4,784,658; 4,936,445; 4,948,000; 5,064,059; and 5,332,399, each of which is incorporated herein by reference in its entirety.

In one example of the ADD-VANTAGE® system, a flexible diluent container includes a receiving port configured to receive a medicament vial closed by a vial stopper. The receiving port is positioned at the top end of the diluent container (i.e., the end of the diluent container that is on top when the diluent container is hung for delivery of its contents to a patient). The flexible diluent container further includes a stopper removal member configured to connect to the vial stopper by engaging an undercut or shouldered recess in the exposed end of the vial stopper. Securement of the vial and the diluent container is accomplished by threadable engagement of threads that circumscribe the outside of the neck portion (which defines the vial opening) of the vial with complementary threads within the diluent container port. Additionally, ratchet teeth, which circumscribe the outside of a skirt member of the vial, engage complementary ratchet teeth located on the interior of the diluent container port. The slopes of the ratchet teeth are such that once engagement is initiated, the vial cannot be backed out of the port without causing visible damage to the vial and/or port, thereby obviating any contamination which may be occasioned by vial-container disengagement and reengagement. In other words, the ratchet teeth are "one-way" ratchet teeth. As the stoppered vial is advanced into and engaged with the port of the diluent container, the vial stopper advances onto the stopper removal member. The stopper removal member is thereby secured to the stopper such that the stopper may subsequently be pulled and removed (via manipulation of the stopper removal member) from the vial, thereby allowing the contents of the two containers to be mixed. The system can then be hung for delivery of the mixture to a patient. To hang the system, the vial is provided with a hanger at its proximal end (i.e., the end opposite the stopper).

The flow path created as a result of activating the stopper removal member of the ADD-VANTAGE® system is defined by the neck of the vial and the dimension of the flow channel defined through the port of the diluent container. The dimension of this flow path is sufficient to permit the contents of the diluent container to flow readily into and out of the vial, (e.g., by "sloshing" the diluent container). By providing significant flow of fluid between the vial and the diluent container, the ADD-VANTAGE® system provides quick and thorough mixing. Further, because the vial is positioned at the top end of the diluent container when the contents of the diluent container are delivered to a patient, any contents remaining in the vial will flow downward into the diluent container.

Another example of a delivery system similar to the ADD-VANTAGE® system is disclosed in U.S. Pat. No. 8,216,207, which is incorporated herein by reference in its entirety. This patent describes a connector that establishes fluid communication between a medicament vial and a diluent container using a feature that pushes the stopper of a medicament vial into the vial upon connecting the medicament vial to the diluent container via the connector. Then upon further insertion of the medicament vial into the connector, the stopper of the diluent container is dislodged thereby establishing fluid communication between the medicament vial and the diluent container.

Another example of a system for transferring and mixing medical compounds and diluents stored in separate containers is the add-EASE binary connector sold by B. Braun Medical, Inc. A first end of the add-EASE connector includes a structure for receiving and securing the connector to a pharmaceutical vial. The first end includes a first spike for penetrating an elastomeric stopper sealing the vial. The second end of the add-EASE connector includes a structure for receiving and securing the connector to a port of a diluent container. The second end also includes a second spike for penetrating an elastomeric closure associated with the port of the diluent container. Once the add-EASE connector has been secured to both the vial and the diluent container, pressure is applied to the contents of the diluent container. This pressure results in a force being applied to a plug member positioned within the first spike, thereby moving the plug from the first spike and into the vial. Because of the relatively narrow flow channel defined by the first and second spikes of the add-EASE connector, it is necessary to pump or "milk" diluent out of the diluent container and into the vial in order to reconstitute and/or dilute the drug contained in the vial. It also is necessary to pump or "milk" the resulting diluent/drug mixture out of the vial back into the diluent container for delivery to the patient. Further, because the diluent container port is positioned at the bottom of the diluent container (i.e., at the end of the diluent container that is positioned closest to the floor when the contents of the diluent container are delivered to a patient) the dimension of the flow channel defined by the first and second spikes must remain small in order to prevent contents of the diluent container from flowing back into the vial (rather than flowing to the patient).

While the above described systems provide solutions for certain medication delivery challenges, the inventors have identified a need in the art for an improved system for mixing substances that provides more convenience and handling, and improves operator and patient safety.

SUMMARY

In one aspect, the invention is directed to system for mixing contents of a first container with contents of a second container. The system includes a first container having contents, a second container having contents, a device constructed to establish fluid communication between the first container and the second container, and a hanger for hanging the system, wherein the hanger is operable only when fluid communication between the first container and the second container has been established.

In a further aspect, the device includes a port housing connected to the second container, and the device further includes a main body constructed to connect to the first container. The port housing rotates relative to the main body, wherein fluid communication is established upon rotation of the port housing relative to the main body. For example, the port housing and the main body rotate from a first position to a second position, wherein the device prevents fluid communication in the first position and the device establishes fluid communication in the second position.

In various embodiments, the hanger is connected to the device, the first container or the second container. The device may also include one or more antirotational members that limit rotation from the second position to the first position.

In another aspect, the invention is directed to a method for preventing errors in the delivery of an intravenous medicament. The method includes providing a first container having contents for intravenous delivery; providing a second container having contents for intravenous delivery; providing a hanger; preventing use of the hanger when the first container and the second container are not in fluid communication; and allowing use of the hanger when the first container and the second container are in fluid communication. In one aspect of this embodiment, the second container includes a device configured for connecting the first container and the second container, the device having a first position in which the first container and the second container are not in fluid communication, the device having a second position in which the first container and the second container are in fluid communication.

In yet another embodiment, the invention is directed to a port assembly for connecting a first container and a second container, the port assembly includes a hanger configured to transition from a first, non-activated condition to a second, activated condition, the port assembly further constructed to move between a first position in which the first and second containers are not in fluid communication and a second position in which the first and second containers are in fluid communication, wherein movement of the port assembly from the first position to the second position causes the hanger to move from the first, non-activated condition to the second, activated condition.

In one aspect, the port assembly includes a circumferential guide slot, the hanger being at least partially positioned within the circumferential guide slot when the hanger is in the first, non-activated condition, the hanger and the circumferential guide slot constructed for relative motion therebetween, the circumferential guide slot being constructed to release the hanger to the second, activated condition upon movement of the port assembly from the first position to the second position.

BRIEF DESCRIPTION OF THE DRAWINGS

Various exemplary embodiments are described herein with reference to the following drawings:

FIG. 36A is an isometric view of the outer retainer part of the retainer shown in FIGS. 34A-D.

FIG. 36B is a top view of the outer retainer part shown in FIG. 36A.

FIG. 36C is a side view of the outer retainer part shown in FIG. 36A.

FIG. 36D is a cross-sectional view of the outer retainer part shown in FIG. 36A.

FIG. 37A is an isometric view of an exemplary seal between the retainer and first container of the system shown in FIGS. 25A-B.

FIG. 37B is a top view of the seal shown in FIG. 37A.

FIG. 37C is a side view of the seal shown in FIG. 37A.

FIG. 37D is a cross-sectional view of the seal shown in FIG. 37A.

FIG. 38A is an isometric view of an exemplary activation collar of the port assembly shown in FIGS. 25A-B.

FIG. 38B is a top view of the activation collar shown in FIG. 38A.

FIG. 38C is a side view of the activation collar shown in FIG. 38A.

FIG. 38D is a bottom view of the activation collar shown in FIG. 38A.

Figure 38A:
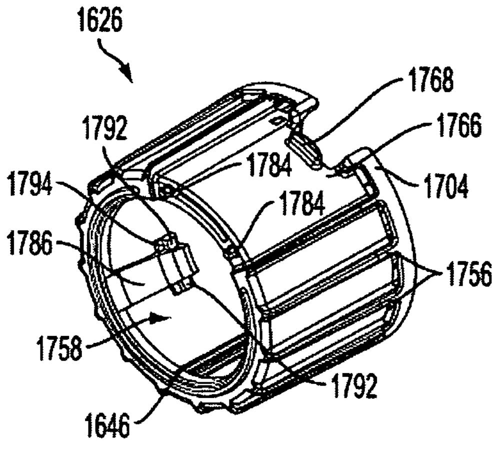
Figure 38B:
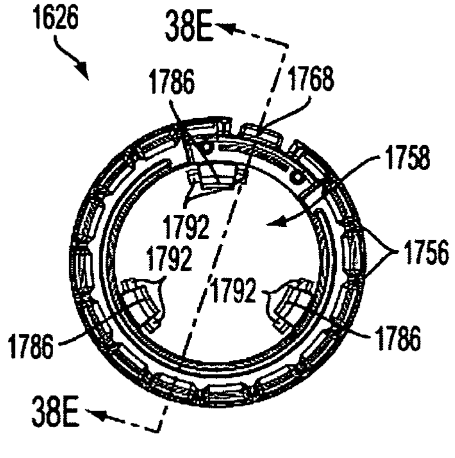
Figure 38C:
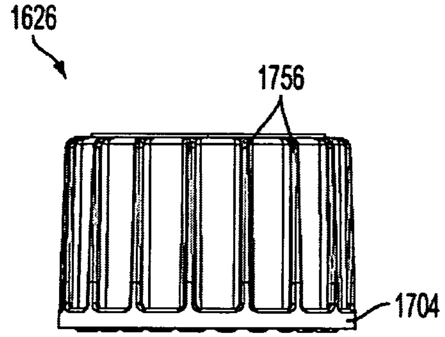
Figure 38D:
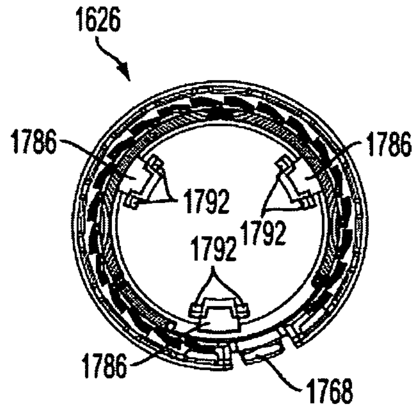
Figure 38E:
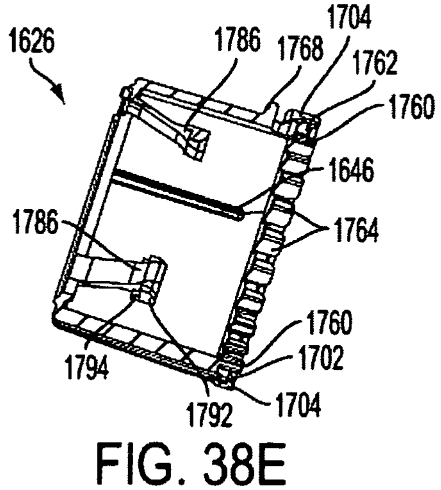

FIG. 38E is a cross-sectional view of the activation collar shown in FIG. 38A.

Figure 25A:
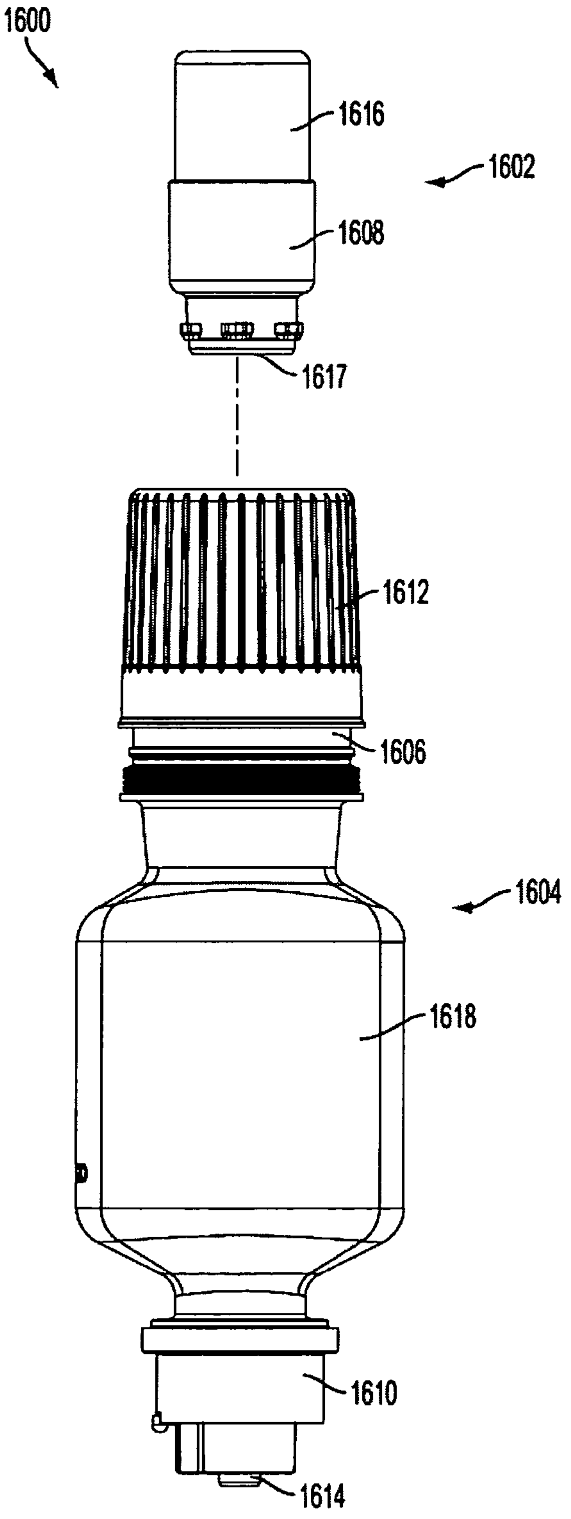
FIG. 25A illustrates a partially exploded view of another exemplary system for mixing the contents of two containers.
Figure 25B:
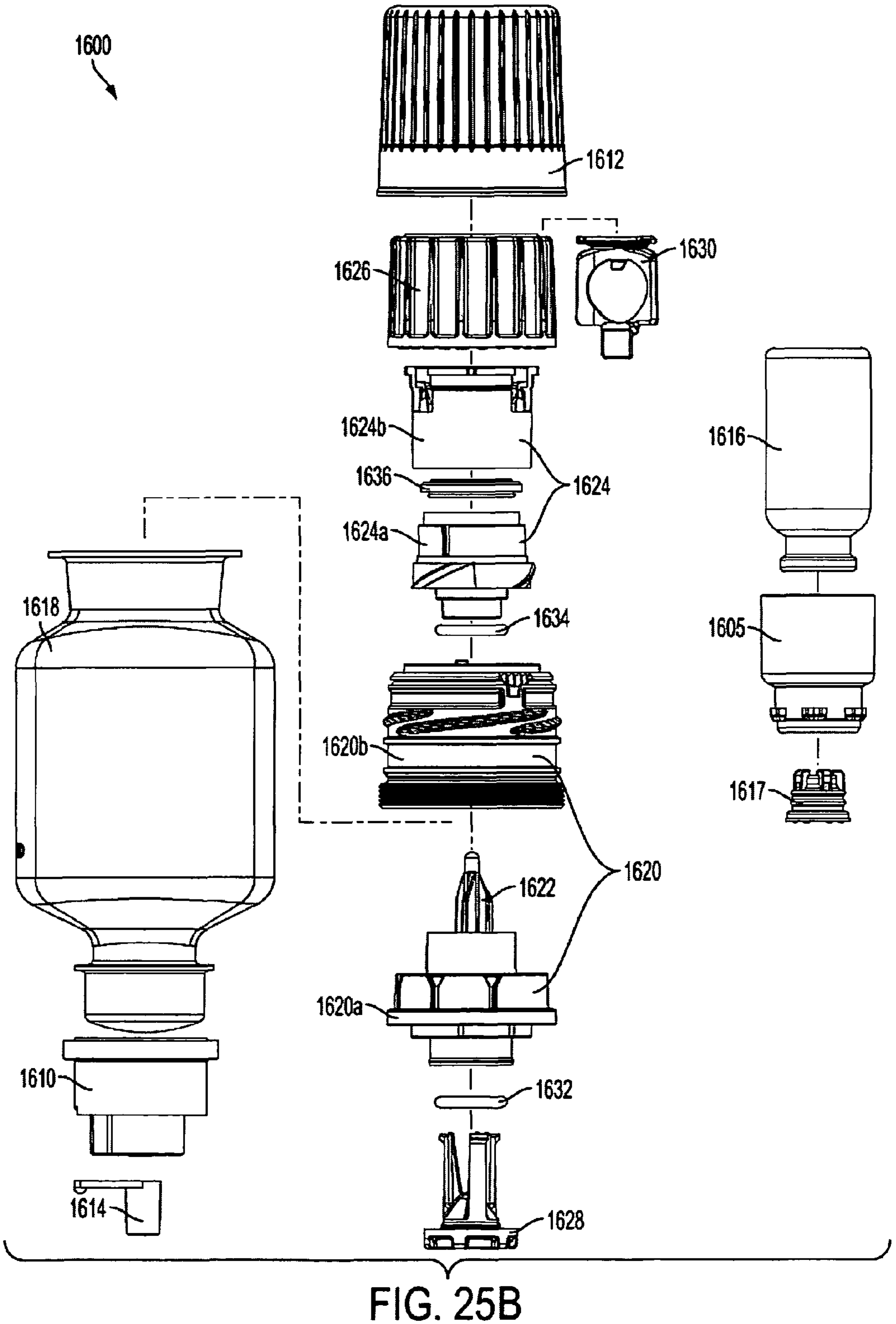
FIG. 25B illustrates a fully exploded view of the system shown in FIG. 25A.
Figure 39A:
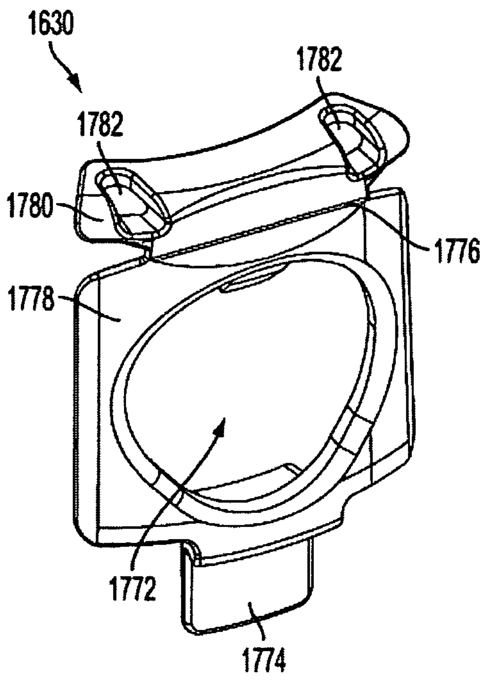

FIG. 39A is an isometric view of an exemplary hanger of the port assembly shown in FIGS. 25A-B.

Figure 39B:
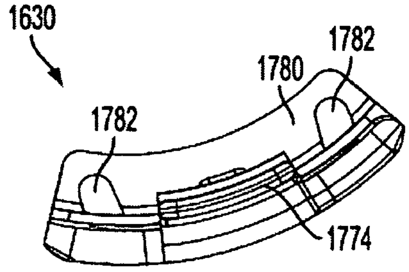

FIG. 39B is a bottom view of the hanger shown in FIG. 39A.

Figure 39C:
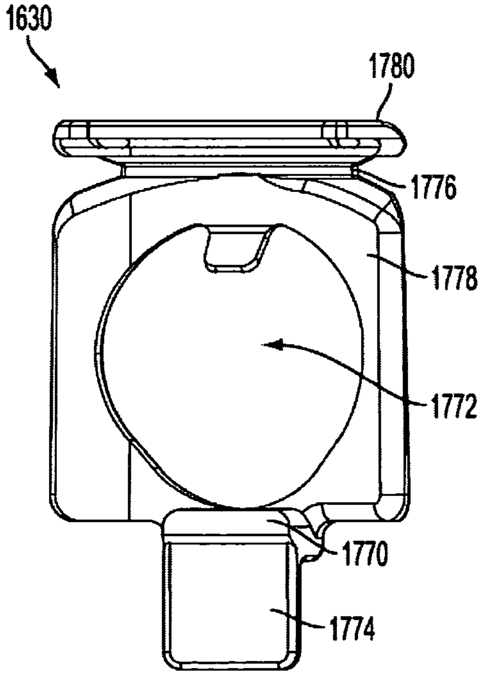

FIG. 39C is another isometric view of the hanger shown in FIG. 39A.

Figure 39D:
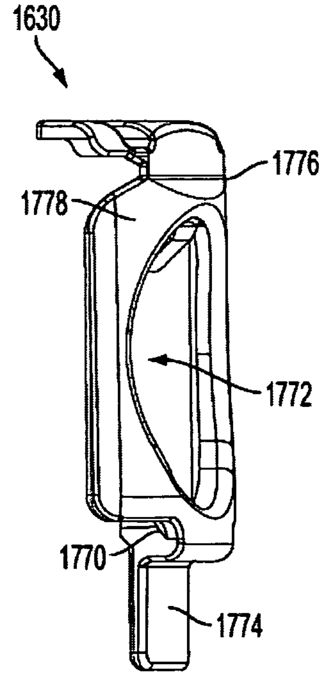

FIG. 39D is another isometric view of the hanger shown in FIG. 39A.

Figure 40A:
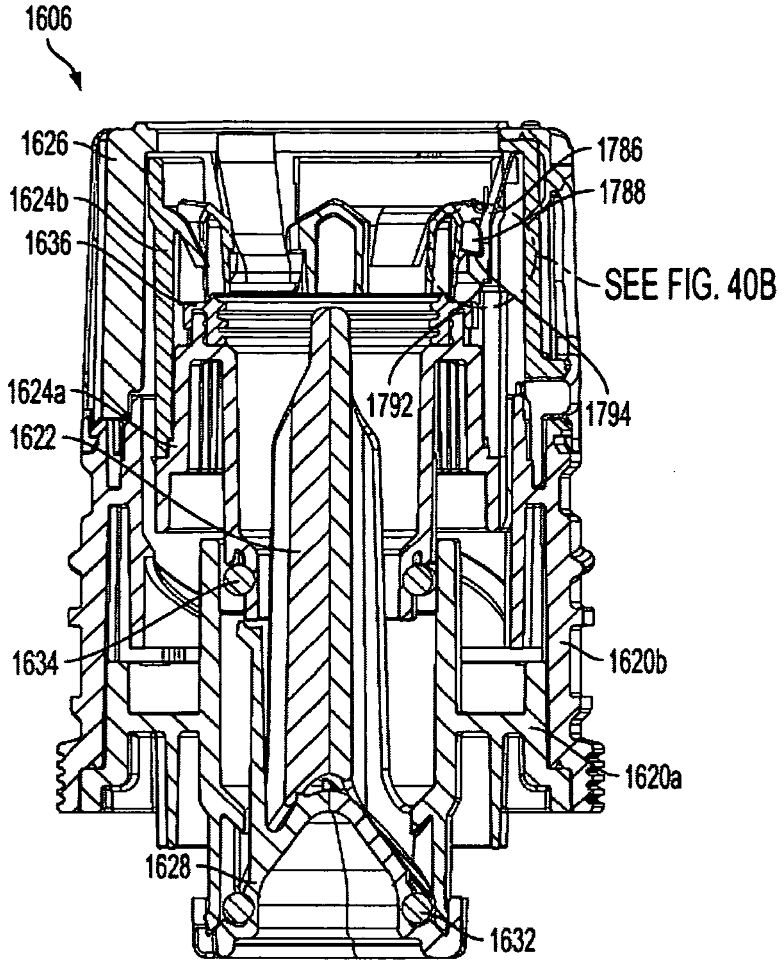

FIG. 40A is a cross-sectional view of an exemplary port assembly that can be used with system shown in FIGS. 25A-B, in the docked position.

Figure 40B:
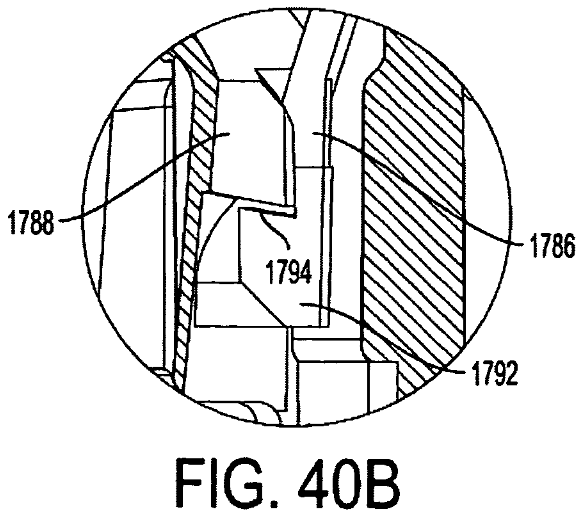

FIG. 40B is a zoomed-in view of the locking mechanism of the port assembly shown in FIG. 40A.

DETAILED DESCRIPTION

Figure 1:
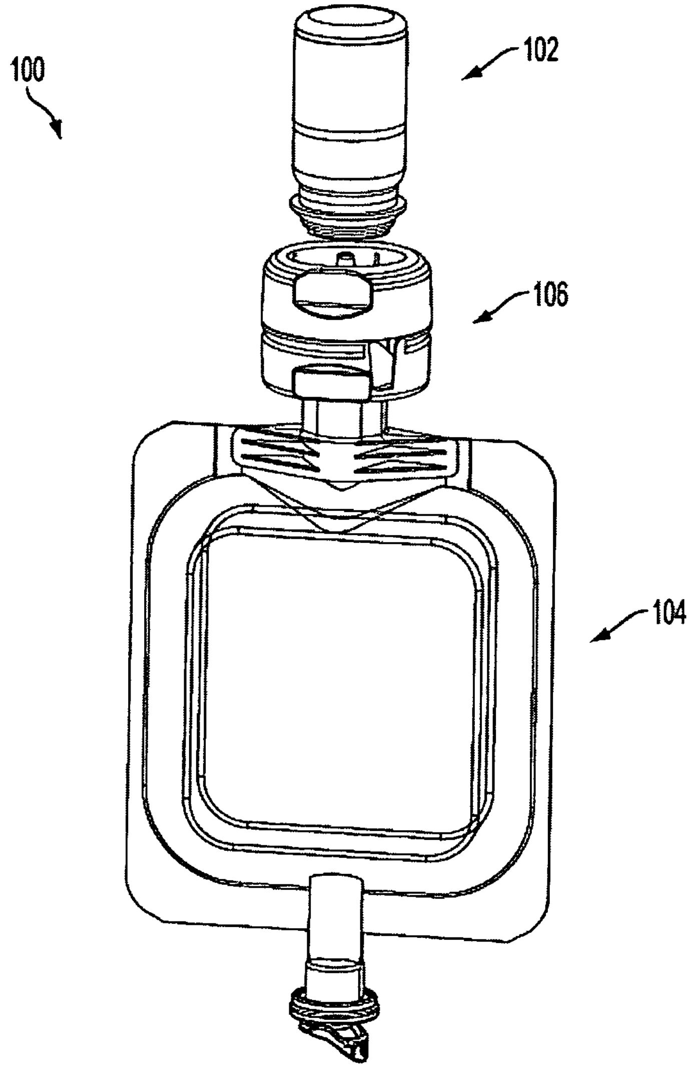
FIG. 1 is a partially exploded isometric view of an exemplary system for mixing the contents of two containers.

The system and corresponding method disclosed herein allow a user (e.g., a pharmacist or other healthcare worker) to mix the contents (e.g., a medicament and a diluent) of two separate containers and then deliver the combined mixture (e.g., a medicinal fluid) to a patient while maintaining sterility of the contents and mixture and preventing unwanted release of the contents and mixture into the environment. FIG. 1 illustrates an exemplary two-component system 100. The system 100 includes (1) a first container 102 containing a first substance and (2) a second container 104 containing a second substance, the second container 104 having a port assembly 106 at its proximal end for receiving the first container 102.

In one embodiment, the first container 102 is a medicament container in the form of a vial having an exterior housing and the second container 104 is a diluent container in the form of a flexible intravenous (IV) solution bag. The flexible bag may be formed from first and second opposing sheets of flexible material that are joined and sealed at the edges to provide a fluid tight cavity for containing a diluent therein. At one edge thereof, the opposing sheets of the flexible diluent container are sealed around at least a portion of the port assembly 106 to mount the port assembly 106 to the second container 104. In one embodiment, the IV bag is constructed of a non-PVC DEHP-free material providing a vapor barrier capability that is sufficient to permit diluent or drug product to be stored therein without the use of an overwrap. For example, the IV bag can be constructed of the materials utilized by Hospira, Inc. in the manufacture of its VISIV® flex container. Other materials for the second container can be used as long as they can be connected to a port assembly 106.

Although described and shown herein as being mounted to the second container 104, the port assembly 106 may be provided as a separate and stand-alone device that connects the first and second containers 102, 104, thereby resulting in a three-component system (i.e., the first container 102, the second container 104, and the port assembly 106).

As used herein, the terms "proximal" and "distal" refer to the opposing directions associated with the orientation of the components of the system. For example, as shown in FIGS. 1, 6A, 6B, 7A and 7B and as more fully described herein, the distal portion of the port assembly 106 is secured to the proximal end of the second container 104, and the proximal portion of the port assembly is configured to receive the distal end of the first container 102.

FIGS. 2A-F illustrate one embodiment of the first container 102. As shown, the first container 102 includes a vial 108 having an exterior housing that includes a body cap 110 and a label sleeve 112. Connected to the body cap 110 is a removable top cap 114. The vial 108 includes a body portion 116 and a neck portion 118 having an annular flange 119 at its distal end that defines an opening 120 in which a stopper 122 is located. In its sealed position, the stopper engages both the opening 120 and the annular flange 119. The opening 120 may be of constant diameter throughout the neck portion 118 of the vial 108 or may have a larger diameter at its distal end (i.e., the end open to the environment) to facilitate the transition of the stopper 122 from a first sealed position in the opening 120 to a second unsealed position within the cavity of first container 102. The larger opening at the distal end can be accomplished by simply enlarging the radius of the edge 121 of the opening 120, thereby allowing a smoother transition of the stopper 122 into the cavity of the vial 108.

Figure 15A:
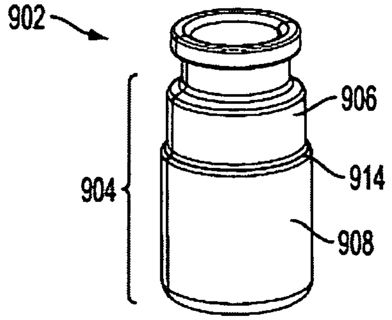
FIG. 15A is an isometric view of another exemplary vial that can be used with the system shown in FIG. 1.

In another embodiment of the vial, as shown in FIG. 15A, the vial 902 may be double stepped. In other words, instead of having a body portion 904 of substantially constant diameter, the distal portion 906 of the body 904 may have a diameter that is smaller than the diameter of the proximal portion 908 of the body 904 as further described below.

Turning back to FIGS. 2A-F, the stopper 122 seals the opening 120 and prevents the contents in the cavity of the vial 108 from escaping out of the opening 120. The stopper 122 has a body portion 124 that is configured to be positioned within the opening 120 of the vial 108 and a top surface 126 that is outwardly facing from the neck 118 when the stopper 122 is in the sealed position shown in FIG. 2B. In one embodiment, the top surface 126 of the stopper 122 has a depression 128 to assist in reducing the force necessary to transition the stopper 122 to the second unsealed position within the cavity of the vial 108 (i.e., the "push-in force") when the first container 102 is docked to the port assembly 106. The depression also acts as a target for a syringe needle or cannula when the contents of the vial are extracted without the use of the system described herein. In an alternate embodiment, there is no depression in the top surface 126 of the stopper 122.

As shown, the stopper 122 has an annular flange 130 radially extending from the body portion 124. The flange 130 is beneficial for maintaining the stopper 122 position in the vial 108, especially when a needle or cannula is inserted through stopper 122. In embodiments where the stopper 122 is a dual-use stopper (i.e., capable of being used with the system described herein or being used separately with a syringe needle or cannula), the stopper 122 is secured tightly enough to the vial 108 that a syringe needle or cannula can be inserted through the stopper 122 to make additions to and/or extract contents from the vial 108 without dislodging the stopper 122. At the same time, the stopper 122 maintains the appropriate push-in force to permit the stopper 122 to be pushed into the vial 108 upon insertion of the first container 102 into the port assembly 106. The stopper push-in force should be achievable by the average user when using the system described herein.

An undercut (not shown) may be provided about the circumference of the stopper 122 at the point at which the underside of flange 130 meets stopper body portion 124. Such an undercut serves as a hinge to assist in reducing the stopper push-in force by more easily enabling flange 130 to fold upwardly when the stopper 122 is being pushed into the vial 108 as the first container 102 is advanced into the port assembly 106 of the second container 104. The undercut may be in the form of a groove having a width in the range of about 0.03-0.1 inches. In an alternative embodiment, the width of the undercut may be in the range of about 0.04-0.07 inches. It will be appreciated by those of ordinary skill in the art that the dimension and shape of the undercut may vary depending upon, among other things, (1) the material from which stopper 122 is constructed and (2) the desired stopper push-in force. In an embodiment where the diameter of the opening 120 is greater near the distal end of the opening, as described above, the stopper push-in force is further reduced as such a configuration allows the flange 130 to fold more easily.

The body cap 110 of the first container 102 is generally positioned around the neck 118 and an upper region of the body portion 116 of the vial 108. The body cap 110 is configured to sealingly engage the vial 108 and the port assembly 106 of the second container 104 such that any diluent, medicament, and/or other contents or combination of contents is prevented from escaping out of the fluid flow path established between the first and second containers 102, 104 during use (e.g., during docking of the first container 102 to the port assembly 106, during activation, during mixing, or during drug delivery to a patent). To assist in providing a sealing engagement with the port assembly 106, the body cap 110 has at least one mating member that engages a complimentary mating member of the port assembly 106 as more fully described below. In one embodiment, the mating member of the body cap 110 is an annular flange 132 that extends radially outward from the sidewall of the body cap 110. As shown, the annular flange 132 is positioned adjacent the distal end 134 of the body cap 110.

Figure 6B:
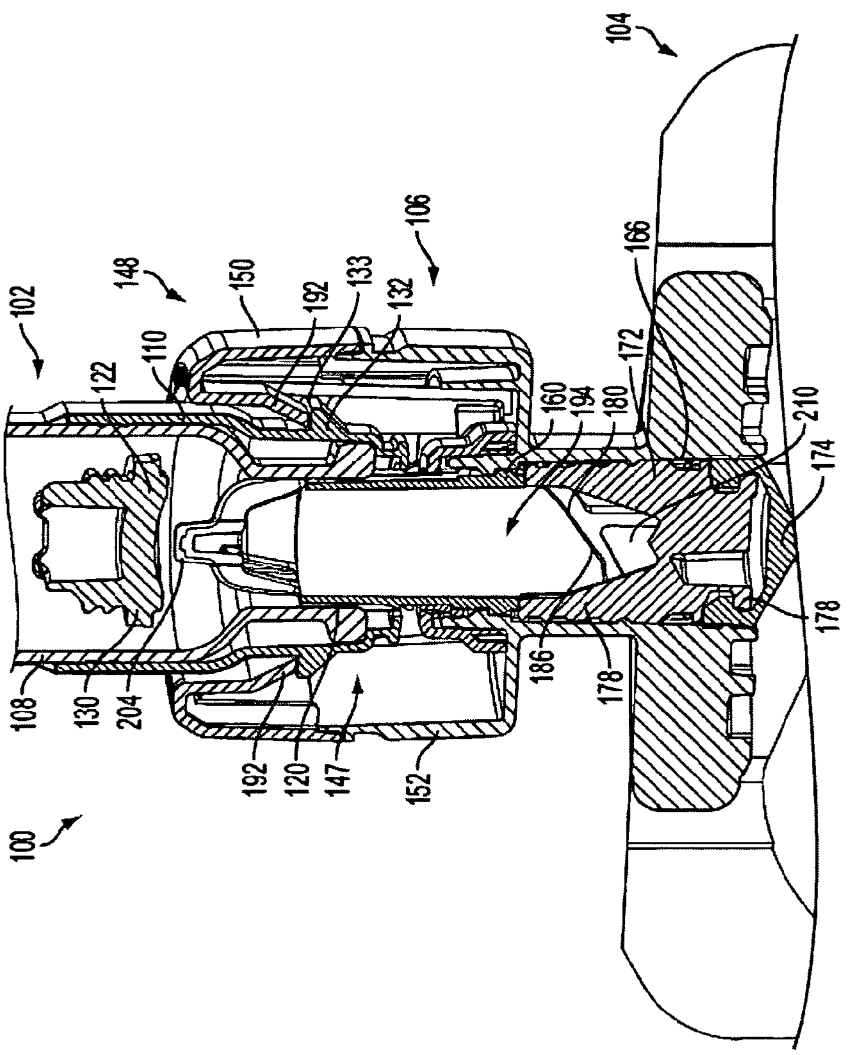
FIG. 6B is a cross-sectional view of the system shown in FIG. 6A.

As shown best in FIG. 6B, the tapered geometry of the annular flange 132 helps to center the first container 102 in the port assembly 106 during the docking step while the underside 133 of the annular flange 132 helps securely dock the first container 102 to the port assembly 106 by providing a surface for the retention tabs 192 of the port assembly 106 to engage. In the depicted embodiments, the annular flange 132 has a circular circumferential perimeter that is sized and shaped to fit within the proximal cavity 147 of the port assembly 106 and to engage retention tabs 192 of the port assembly 106. In alternative embodiments, the annular flange 132 may have an interrupted circumferential perimeter (e.g., one or more gaps or voids are present about the circumference).

As illustrated in one embodiment of the body cap shown in FIGS. 19A-19E, the body cap 1302 may be configured to partially cover the opening 1303 of the vial 1306 and the stopper 1304. Such a configuration helps to maintain the position of the body cap 1304 on the vial 1306. As shown, the distal end of the body cap 1302 extends radially inward over a portion of the opening 1303 of the vial 1306 and the top surface 1310 of the stopper 1304, while providing an opening 1312 through which the stopper 1304 can be accessed by, for example, a syringe needle or cannula. In addition to helping maintain the position of the body cap 1302 on the vial 1306, the radially inward extending portion (herein sometimes referred to as "the annular sealing member") 1314 of the distal end of the body cap 1302 forms a fluid seal with the actuator 1316 when the first container 1318 is docked to the port assembly (only the actuator 1316 is shown) of the second container (not shown), as shown in FIGS. 19B-E. In one embodiment, the portion of the stopper 1304 that is accessible through the opening 1312 of the body cap 1302 is elevated so that it lies in substantially the same plane as the radially inward extending portion 1314. The elevated portion of the stopper 1304 can act as a target for a syringe needle or cannula in the event it is desirable to access the vial in that fashion.

In one embodiment, the entire body cap 1304 including the radially inward extending portion 1314 in composed of a single material. In other embodiments, the radially inward extending portion 1314 may be composed of a different material than the rest of the body cap 1304. In either case, the radially inward extending portion 1314 should be elastic/resilient enough to form a fluid seal with the actuator 1316 when the first container 1318 is docked to the port assembly of the second container.

Figure 15B:
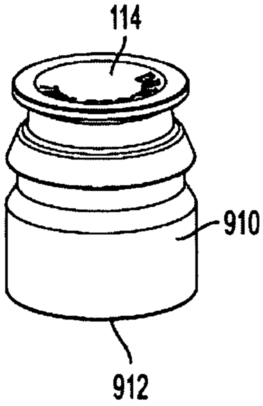
FIG. 15B is an isometric view of an exemplary body cap that can be used with the vial shown in FIG. 15A.
Figure 15C:
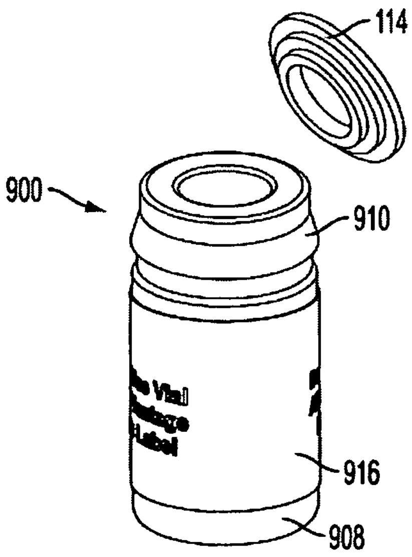
FIG. 15C is an isometric view of another exemplary first container comprising the vial and body cap of FIGS. 15A and 15B respectively.

In an embodiment of the first container 900 having a double-stepped vial 902, as shown in FIGS. 15A-C, the body cap 910 circumscribes the distal portion 906 (smaller diameter portion) of the body 904 of the vial 902 such that the proximal end surface 912 of the body cap 910 abuts the transition ledge 914 between the distal and proximal portions 906, 908 of the double stepped vial 902. The difference between the diameters of the distal and proximal portions 906, 908 is such that when the body cap 910 is applied to the vial 902, the outer perimeter of the body cap 910 is flush with the outer surface of the proximal portion 908 of the vial 902. When a shrink sleeve 916 is placed over the vial 902 and body cap 910, the sleeve 916 lays flat on the vial 902 and body cap 910. When the sleeve is a shrink sleeve 916, the reformed shape of the sleeve 916 after it is heated and shrunk in place will aid in securing the body cap 910 the vial 902 and may also create a sterility barrier that protects the underside of the body cap 910 including the vial stopper. In one embodiment, the shrink sleeve 916 may be transparent so that when the vial 902 and body cap 910 are also transparent, an operator can view a needle syringe or cannula being inserted into the container 900. The shrink sleeve 916 may also contain one or more glue strips on the inside of the sleeve 916 that further aids in securing the cap 910 to the vial 902.

Referring back to FIG. 2B, the body cap 110 may also include first and second rib seals 146. The rib seals 146 are protrusions extending radially inward from the interior surface of the body cap 110 to engage the vial 108 and to provide an additional seal against contaminants entering the cavity 138 of the body cap 110. The annular rib seals 146 may be located anywhere along the interior wall of the body cap 110 as long as they seal against the outer surface of the vial 108. In one embodiment, each rib seal 146 is interrupted twice at approximately 180 degrees to allow for venting of the cavity 138, however, in such an embodiment, the interruptions of the first rib seal 146 may be offset 90 degrees from the interruptions of the second rib seal 146 to provide a tortuous path for the preservation of sterility of the cavity 138 of the body cap 110. Of course other degrees of offset between the rib seals are possible.

The body cap may be made of polypropylene, but many suitable materials would be known to one of skill in the art. The vial and body cap may be suitable for radiation sterilization at a minimum of 34 kGy. Accordingly, other suitable materials for the body cap include, for example, PCT and DEHP.

Figure 2A:
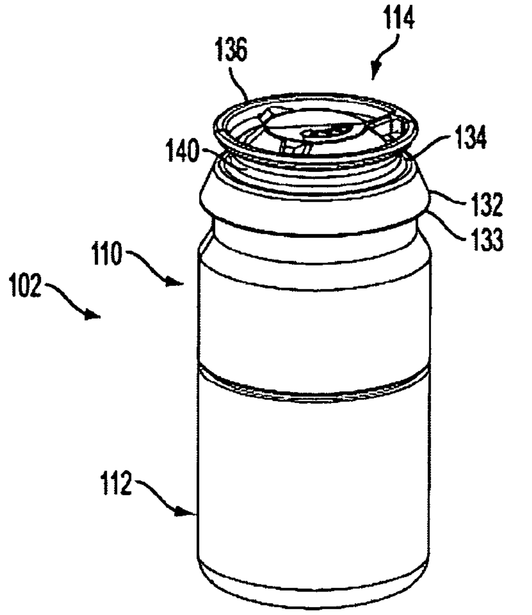
FIG. 2A is an isometric view of an exemplary first container of the system shown in FIG. 1.
Figure 2B:
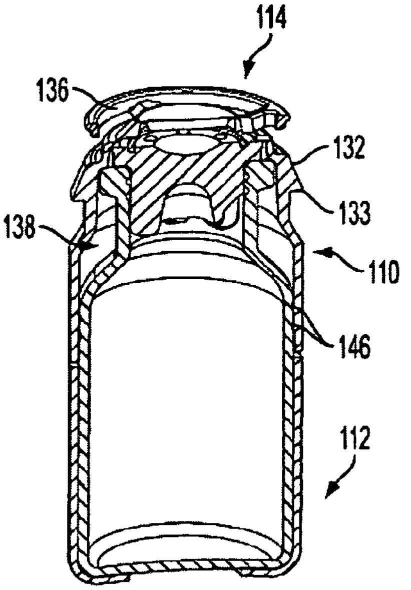
FIG. 2B is a cross-sectional view of the first container shown in FIG. 2A without the vial.
Figure 2C:
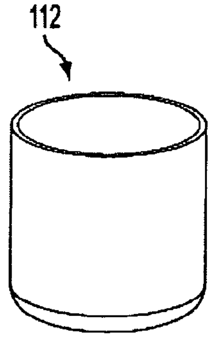
FIG. 2C is an isometric view of the label sleeve of the first container shown in FIG. 2A.
Figure 2D:
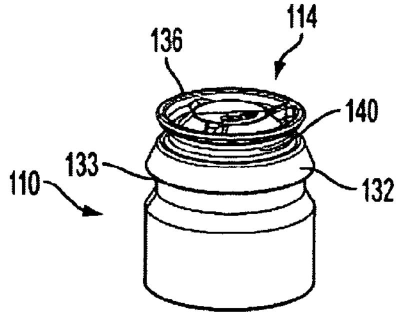
FIG. 2D is an isometric view of the body cap and top cap of the first container shown in FIG. 2A.
Figure 2E:
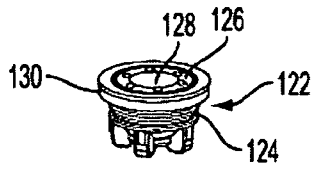
FIG. 2E is an isometric view of the stopper of the first container shown in FIG. 2A.
Figure 2F:
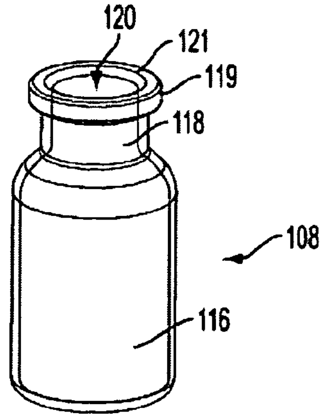
FIG. 2F is an isometric view of the vial of the first container shown in FIG. 2A.

A removable top cap 114 may be provided at the distal end of the body cap 110. In one embodiment, as shown in FIGS. 2A, 2B, and 2D, the top cap 114 has a pull ring 136 associated therewith to assist in removing the top cap 114 from the body cap 110. The top cap 114 prevents the first container 102 from being docked to the port assembly 106 prior to its removal. The top cap 114 also protects the first container 102 from any attempted tampering by generally providing a protective seal over the opening to the body cap 110 to seal the internal cavity 138 of the body cap 110 from the outside environment and to prevent access to the stopper 122. A thin wall 140 joins the top cap 114 to the body cap 110 and can be ruptured to disconnect the top cap 114 from the body cap 110. To remove the top cap 114, a user pulls on the pull ring 136, which in turn ruptures the thin wall 140 connecting the top cap 114 to the body cap 110, thereby disconnecting the top cap 114 from the body cap 110. Because thin wall 140 is ruptured in the process of removing top cap 114 from body cap 110, top cap 114 cannot be easily reattached, thus providing evidence of possible tampering with the contents of first container 102. The body cap 110 and top cap 114 may be manufactured integrally from a low density polyethylene. However, it will be appreciated that a variety of materials, and combinations of materials, can be used in the manufacture of body cap 110 and top cap 114.

Figure 3A:
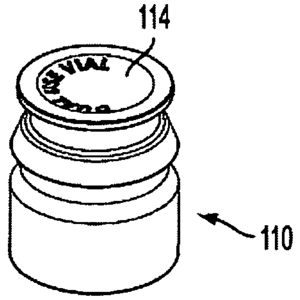
FIG. 3A is an isometric view of another exemplary body cap and top cap that may be used with the first container shown in FIGS. 2A-F.
Figure 3B:
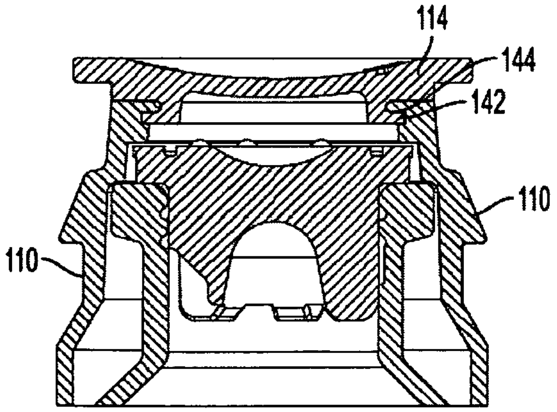
FIG. 3B is a cross-sectional view of the body cap and top cap shown in FIG. 3A.
Figure 4A:
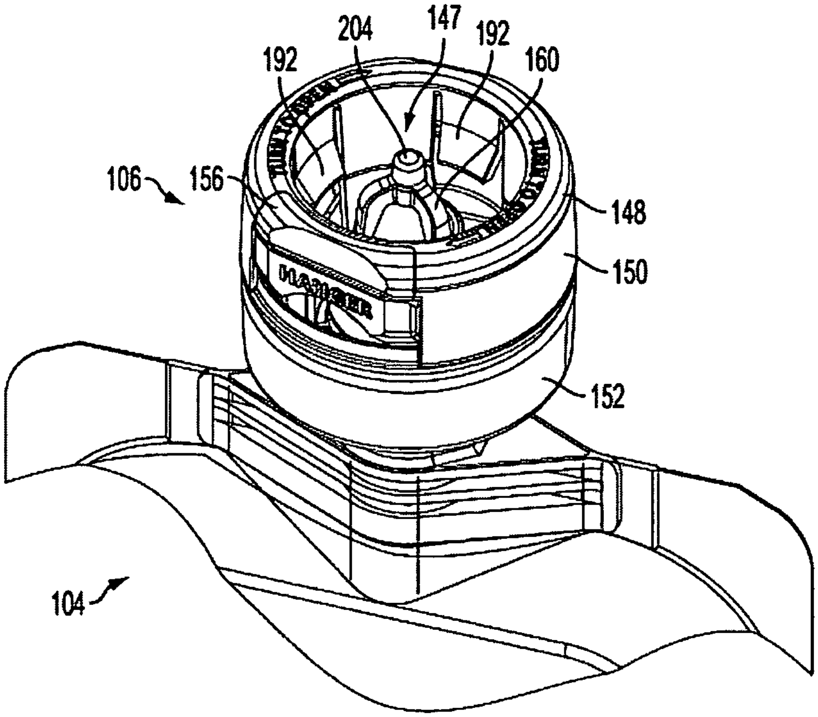
FIG. 4A is an isometric view of an exemplary second container and port assembly of the system shown in FIG. 1.
Figure 4B:
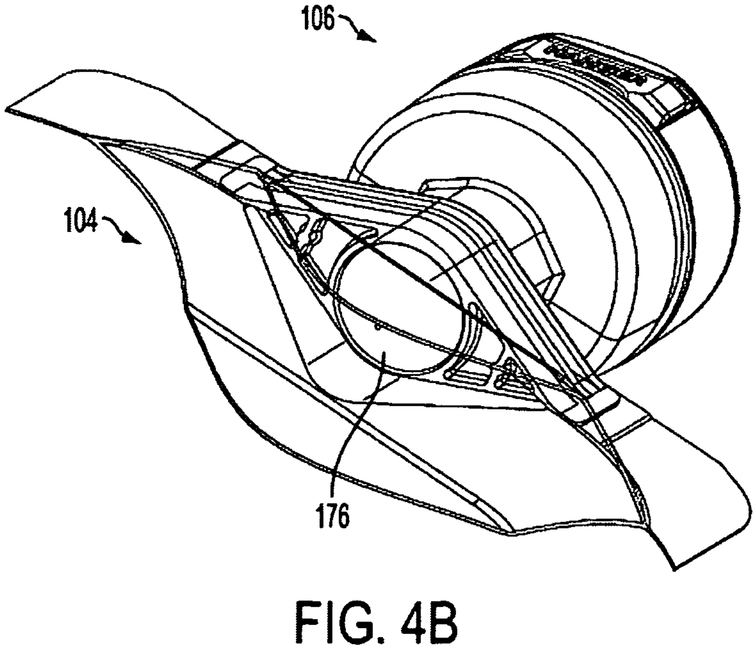
FIG. 4B is another isometric view of the second container and port assembly shown in FIG. 4A.

In another embodiment of the top cap 114 shown in FIGS. 3A and 3B, the top cap 114 does not include a pull ring 136. Rather, the top cap 114 engages the body cap 110 via an annular flange 142 that engages a compatible annular recess 144 in the interior wall of the body cap 110. Those skilled in the art will appreciate that other attachment means can also be used.

In a further embodiment of the top cap shown in FIGS. 9A-9E, the top cap 302 engages the body cap 304 via a partially circumferential radial protrusion 306 that engages a compatible radial groove 308 in the exterior wall of the body cap 304. As shown, the top cap 302 includes a pull ring 310 in the form of an annular rim. In the untampered state, the pull ring 310 is attached to the body of the top cap 302 via two frangible pull ring attachment features 312 (only one is shown) disposed on opposite sides of the top cap 302 and a tab 314 formed by frangible surfaces 316 extending from a side wall 318 of the top cap 302 to a position on the top surface 320 of the top cap 302. To remove the top cap 302, a user pulls up on the pull ring 310 which causes the frangible pull ring attachment features 312 to fracture. Further pulling on the pull ring 310 causes the two frangible surfaces 316 to fracture thus allowing the radial protrusion 306 to be disengaged from the radial groove 308 such that the top cap 302 can be completely removed from the body cap 302. Depending on the desired cap removal force, alternative embodiments may include a different number of frangible pull ring attachment features 312 and surfaces 316. Because the frangible attachment features 312 and surfaces 316 are ruptured in the process of removing the top cap 302 from the body cap 304, the top cap 302 cannot be easily reattached, thus providing evidence of possible tampering with the contents of first container.

Figure 10A:
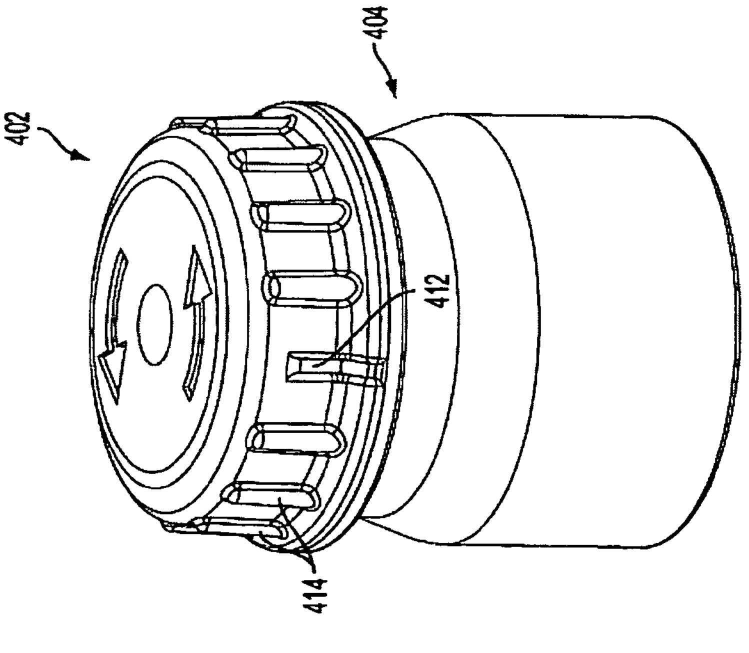
FIG. 10A is an isometric view of another exemplary body cap and top cap that may be used with the first container shown in FIGS. 2A-F.
Figure 10B:
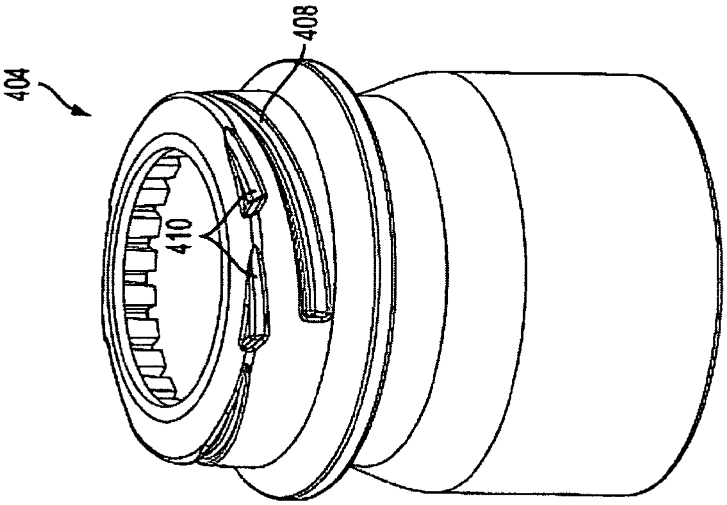
FIG. 10B is an isometric view of the body cap shown in FIG. 10A.
Figure 10C:
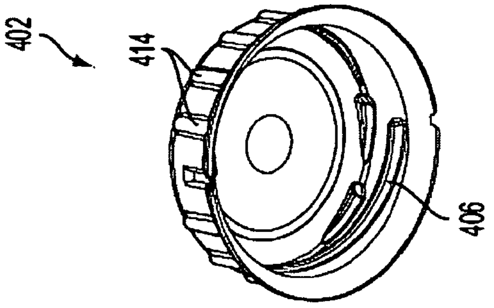
FIG. 10C is an isometric view of the top cap shown in FIG. 10A.

In yet another embodiment of the top cap shown in FIGS. 10A-10C, the top cap 402 engages the body cap 404 via compatible thread features 406, 408. To prevent reattachment of the top cap 402 to the body cap 404, the diameter of the female thread 408 of the body cap 404 increases as it rises vertically (i.e., the depth of the thread groove decreases). Thus, as the top cap 402 is rotated relative to the body cap 404 to unscrew the top cap 402 from the body cap 404, the male thread 406 of the top cap 402 is forced to turn through the increasing diameter of the female thread 408 of the body cap 404, which causes the top cap 402 to deform (expand radially outwardly) as it is removed. Once removed, the resilient nature of the top cap 402 causes the top cap 402 to return substantially to its undeformed configuration. The increasing diameter of the female thread 408 of the body cap 404 prevents reattachment of the top cap 402 by making it difficult to thread the top cap 402 onto the body cap 404. To further prevent reattachment of the top cap 402 to the body cap 404, the body cap 404 includes anti-threading features 410, which obstruct the male thread 406 of the top cap 402 from entering the female thread 408 of the body cap 404. Thus, the user is prevented from threading the top cap 402 onto the body cap 404. Moreover, the top cap 402 may include a frangible surface 412 that fractures due to the deformation caused as the top cap 402 is removed from the body cap 404. Alternative embodiments may include a different number of frangible surfaces 412. Because of the combination of the frangible surface 412 rupturing in the process of removing top cap 402 from body cap 404, the increasing diameter of the thread 408 of the body cap 404, and the anti-threading features 410 of the body cap 404, top cap 402 cannot be easily reattached to the body cap 408, thus providing evidence of possible tampering with the contents of first container. As shown, the top cap 402 includes ridges 414 that assist in the removal of the top cap 402 by allowing a user to more easily grip and rotate the top cap 402.

Figure 16A:
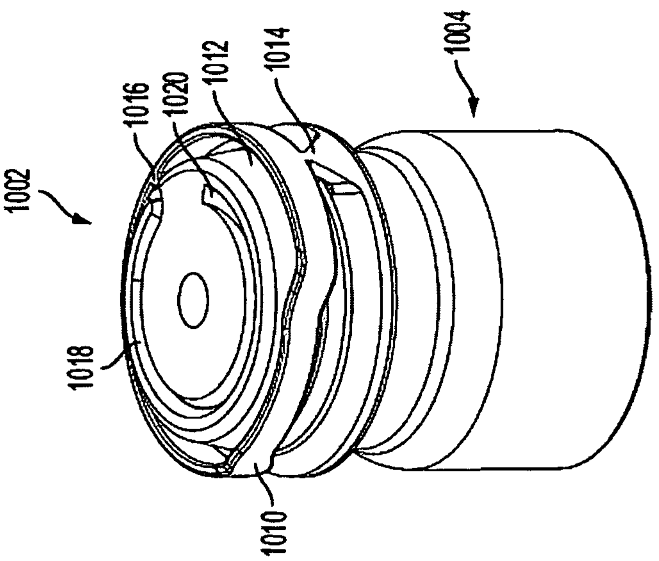
FIG. 16A is an isometric view of another exemplary body cap and top cap that may be used with the first container shown in FIGS. 2A-F.
Figure 16B:
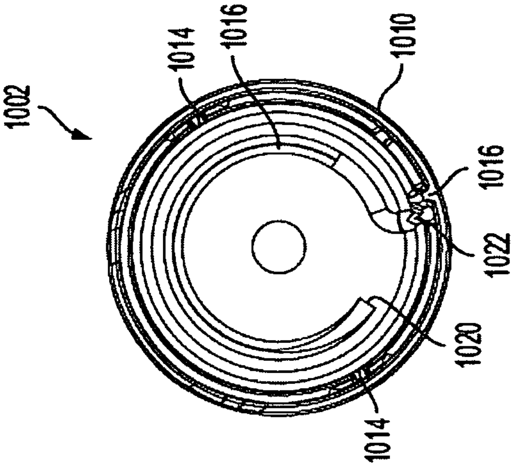
FIG. 16B is a top view of the body cap and top cap shown in FIG. 16A.
Figure 16C:
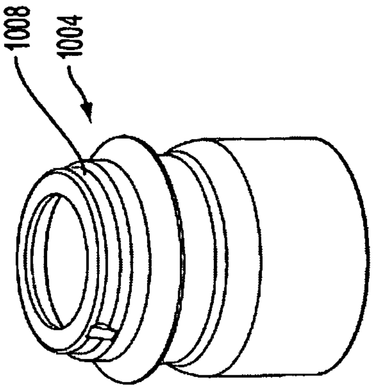
FIG. 16C is an isometric view of the body cap shown in FIG. 16A.

In another embodiment of the top cap shown in FIGS. 16A-C, the top cap 1002 engages the body cap 1004 via a partially circumferential radial protrusion (not shown) that engages a compatible radial groove 1008 in the exterior wall of the body cap 1004. As shown, the top cap 1002 includes a pull ring 1010 in the form of an annular rim. In the untampered state, the pull ring 1010 is attached to the body 1012 of the top cap 1002 via two frangible pull ring attachment features 1014 disposed on opposite sides of the top cap 1002 and a bridge 1016. To remove the top cap 1002, a user pulls up on the pull ring 1010 which causes the frangible pull ring attachment features 1014 to fracture. Further pulling on the pull ring 1010 causes the partially circumferential frangible path 1018 to fracture at the region 1022 adjacent the bridge 1016 and then continue to fracture until the end stop 1020 of the frangible path 1018 is reached. At this point, the radial protrusion of the top cap can be disengaged from the radial groove 1008 of the body cap 1004 such that the top cap 1002 can be completely removed from the body cap 1004. Depending on the desired cap removal force, alternative embodiments may include a different number of frangible pull ring attachment features 1014 or a different frangible path geometry (e.g., one that spans more or less of the circumference of the top cap 1002). Because the frangible attachment features 1014 and partially circumferential path 1018 are ruptured in the process of removing top cap 1002 from body cap 1004, top cap 1002 cannot be easily reattached, thus providing evidence of possible tampering with the contents of first container.

As shown in the embodiment of the second container 104 illustrated in FIGS. 4A-5C, the second container 104 is secured to the distal portion of the port assembly 106. The port assembly 106 has a main body 148 that is configured to receive the first container 102 and engage the body cap 110 of the first container 102 such that the first container 102 can be securely docked to the assembly 106. To activate the system after the first container 102 is docked, a user rotates the main body 148 relative to the port housing 152 (i.e., the portion of the port assembly 106 that is secured to the second container 104). As shown best in the exploded views of FIGS. 5B and 5C, the port assembly 106 generally includes (i) a port housing 152; (ii) a plug member 154; (iii) a main body 148 having an activation collar 150, and a retaining feature having retention tabs 192 to secure the first container; and (iv) an actuator 160. The main body 148 may also optionally include a hanger 156. The port assembly 106 is covered with a removable cap 162 in order to maintain sterility of the assembly 106 prior to use. The various components of the port assembly may be manufactured from materials that are autoclavable and/or UV sterilizable.

In the embodiment shown in FIGS. 4A-5C, the port housing 152 serves as a mount for the opposing flexible sheets of the IV bag. In one embodiment, the port housing 152 has a semi-elliptical outer shape to assist in sealing the second container 104 to the port assembly 106. Any known sealing technique in the art may be used such as heat sealing, RF welding, or adhesive. The proximal end of the port housing 152 defines a cavity 164 that is configured to receive and engage the main body 148 such that the main body 148 can rotate relative to the port housing 152.

Axially aligned and supported in the cavity 147 of the main body 148 is the actuator 160 having a flow passageway 194 through its interior that is substantially axially aligned with the interior bore 166 of the port housing. The actuator 160 is secured to (and supported axially by) the main body 148 such that rotation of the main body 148 results in corresponding rotation of the actuator 160. Accordingly, in this embodiment, little to no relative rotation between the actuator 160 and main body 148 should exist. In addition, the actuator 160 should be secured to the main body 148 to prevent fluid leakage between the actuator 160 and the main body 148. Securement may be achieved using any known connection mechanisms in the art. As shown, the actuator 160 includes a sealing ring 214 to provide a leak-proof seal between the actuator 160 and the main body 148. In alternative embodiments the actuator 160 may include a plurality of sealing rings 214 for sealing securement to the main body 148. In one particular embodiment, the actuator is molded in a double-shot process wherein a rigid material for the body of the actuator 160 and a resilient material for the sealing ring 214 are molded together.

The proximal end of the actuator 160 is formed of a plurality of sidewall members or ribs 196 that extend from a shoulder 198 of the body portion 200 of the actuator 160 towards the proximal end of the cavity 147. In one embodiment, the proximal end of the actuator 160 is comprised of three ribs 196 with gaps 202 therebetween. The ribs 196 define at least a portion of the flow passageway 194 of the actuator 160 and the gaps 202 provide access from the cavity 147 into the flow passageway 194. When the first container is docked to the port assembly 106, the actuator 160 enters the opening 120 of the first container 102 thereby forcing the stopper 122 out of its sealed position in the opening 120 of the first container 102 to its unsealed position in the cavity of the first container 102. As a result, fluid communication between the flow passageway 194 of the actuator 160 and the cavity of the first container 102 is established.

In one embodiment, the outermost diameter of the ribs 196 (i.e., where the ribs 196 meet the shoulder 198) of the actuator 160 is approximately equal to the inside diameter of the opening 120 of the first container 102. The proximal ends of the ribs 196 are angled inwardly toward the actuator tip 204 (i.e., the portion of the actuator 160 that initially contacts the stopper 122 of the first container 102 during docking) The actuator 160 may be constructed of a relatively rigid material so that it is capable of displacing the stopper 122 into the cavity of the first container 102 upon docking of the first container to the port assembly 106. As shown, the actuator 160 includes two sealing rings 216 that engage the inner surface of the neck portion 118 of the vial 108 after the actuator enters the opening 120 during docking, thereby creating a fluid seal and preventing leakage of the contents of the first container 102 after docking. In alternative embodiments a different number of sealing rings 216 may be used. In one particular embodiment, the actuator is molded in a double-shot process wherein a rigid material for the body of the actuator 160 and a resilient material for sealing rings 216 are molded together.

In an embodiment where the distal end of the body cap 1302 extends radially inward over a portion of the opening of the vial 1306 and the top surface 1310 of the stopper 1304 while providing an opening 1312 through which the stopper 1304 is accessible, as shown in FIGS. 19A-E, the actuator 1316 may or may not include sealing rings 216. As noted above, in such an embodiment, the radially inward extending portion 1314 of the distal end of the body cap 1302 forms a fluid seal with the actuator 1316 when the first container 1318 is docked to the port of the second container, as shown in FIGS. 19B-E.

Figure 5A:
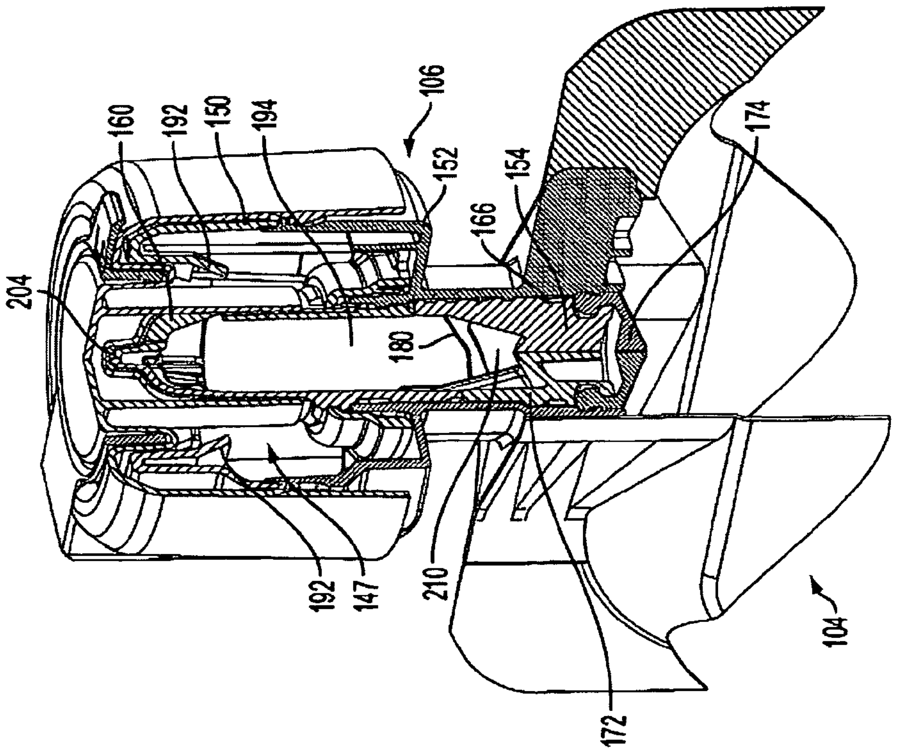
FIG. 5A is a partial cross-sectional isometric view of the port assembly and second container shown in FIGS. 4A-B.
Figure 5B:
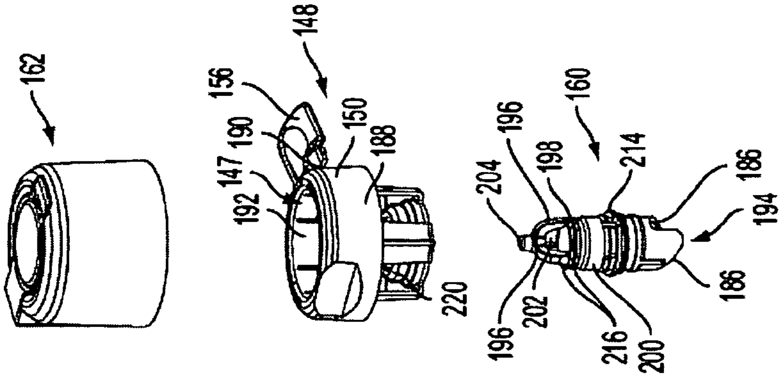
FIG. 5B is an exploded isometric view of the main body, actuator, and cap of the port assembly shown in FIG. 5A.

Turning back to the embodiment shown in FIG. 5B, the distal end of the actuator 160 (herein sometimes referred to as a "cam member") includes two angled surfaces 186, each sloping in opposite directions. These angled surfaces 186 are configured to interact with complimentary angled surfaces 180 of the plug retainer 172 in a cam-like fashion during activation of the system as described in detail below. Alternative embodiments of the actuator 160 may include a single angled surface 186 at the distal end that is configured to interact with a single angled surface 180 of the plug retainer 172.

After docking the first container 102 to the port assembly 106 but prior to activation of the system, plug member 154 prevents fluid communication between the first and second containers 102, 104 by sealing the bore 166 of the port housing 152. The plug member 154 may be a single unitary component or comprised of multiple components such as a plug retainer 172 and a plug stopper 174, as shown best in FIG. 5C. In such a two-component embodiment, the plug stopper 174 is configured to prevent contents from escaping into or out of the second container 104 through the interior bore 166 of port housing 152. The plug stopper 174 includes an annular recess 176 that is configured to engage an annular flange 177 of the plug retainer 172. Alternative embodiments may include any other known connection means in the art.

Figure 5C:
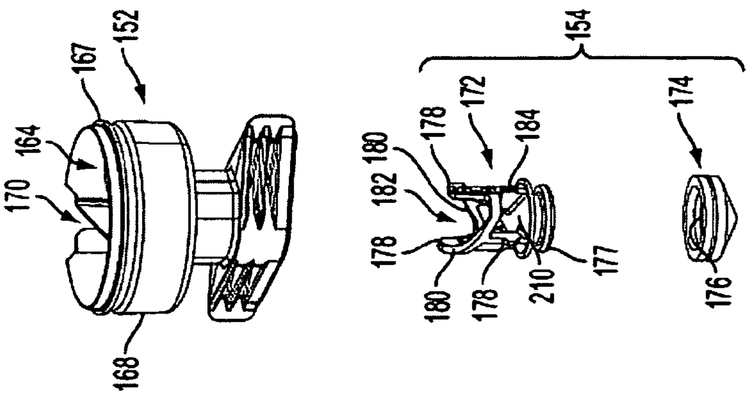
FIG. 5C is an exploded isometric view of the port housing and plug member of the port assembly shown in FIG. 5A.

As shown best in FIG. 5C, the plug retainer 172 has a plurality of legs 178 extending proximally away from the plug stopper 174. Any number of legs are possible, for example, two, three or four. The legs 178 partially define a central bore 182 in the plug retainer 172 that is axially aligned with the bore 166 of the port housing 152. Additionally, between each leg 178 and below the portions of the plug retainer 172 that form the proximal angled surfaces 180, multiple inlet/outlet windows 210 are provided that allow access to the central bore 182. The windows 210 are in direct fluid communication with the contents of the second container 104 after activation of the system 100, which causes the plug stopper 174 to move distally into the cavity of the second container 104 without releasing the plug stopper 174. Further, one or more of the legs 178 includes a splined protrusion 184 that engages a corresponding groove (not shown) in the internal surface of the interior bore 166 of the port housing 152 so that the plug member 154 can slide axially relative to the port housing 152 and the actuator 160 during activation. The splined protrusion 184 may run the length of the leg 178, a portion of the length of the leg 178, or be comprised of multiple protrusions distributed along the length of the leg 178. Moreover, each leg 178 need not include the same splined protrusion 184.

In an alternative embodiment, the plug retainer 172 may include one or more legs 178 that include snap features (not shown) in addition to one or more legs 178 that include a splined protrusion 184. Such snap features may be configured to engage compatible snap features (not shown) on the inner surface of the bore 166 of the port housing 152. These snap features may provide tactile feedback to the user during activation and may also ensure that the plug member 154 does not inadvertently move in the proximal direction (i.e., to its pre-activation configuration) after activation. In other words, as the plug member 154 moves in the distal direction, snap features of the legs 178 may advance into engagement with compatible snap features on the inner surface of the bore 166 of the port housing 152. This may help to ensure that the optimum fluid flow path is maintained between the first and second containers 102, 104 after activation so that the contents of the containers may be sufficiently mixed.

The splined engagement between the plug retainer 172 and the port housing 152 allows the plug member 154 to slide axially relative to the port housing 152 but prevents relative rotation therebetween. Those skilled in the art will appreciate that in an alternative embodiment, one or more of the legs 178 may contain an axially oriented groove that engages a corresponding spline on the internal surface of the interior bore 166.

As mentioned above, the proximal angled surfaces 180 of the plug retainer 172 are configured such that they cooperate with the distal angled surfaces 186 of the actuator 160 during activation of the system 100. Prior to activation, the angled surfaces 180 of the plug retainer 172 are substantially parallel to the angled surfaces 186 of the actuator 160. Accordingly, as a user rotates the main body 148 (which in this embodiment the actuator 160 is rotationally and axially fixed) relative to the port housing 152 (which in this embodiment the plug retainer 172 is rotationally fixed but free to move axially via the splined engagement), the actuator 160 undergoes corresponding rotation, which results in the distal angled surfaces 186 of the actuator 160 contacting the proximal angled surfaces 180 of the plug retainer 172. As the actuator 160 rotates, the distal angled surfaces 186 of the actuator 160 act as a cam that translate the rotational motion of the actuator 160 into linear motion of the plug member 154, which forces the plug stopper 174 and a portion of the plug retainer 172 into the cavity of the second container thereby placing the windows 210 of the plug retainer 172 in direct fluid communication with cavity of the second container 104 and opening a fluid flow path from the cavity of the second container 104, through the plug retainer 172 and the actuator 160, to the cavity of the first container 102.

The distal angled surfaces 186 of the actuator 160 and the proximal angled surfaces 180 of the plug retainer 172 should be dimensioned such that the desired vertical displacement of the plug member 154 is achieved when the system 100 is activated by rotating the main body 148.

Figure 11C:
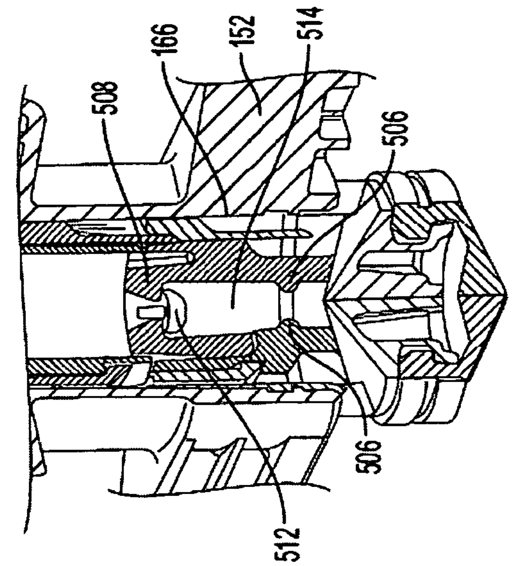
FIG. 11C is a cross-sectional view of the plug retainer of FIG. 11A in the activated position within an exemplary port assembly.
Figure 11B:
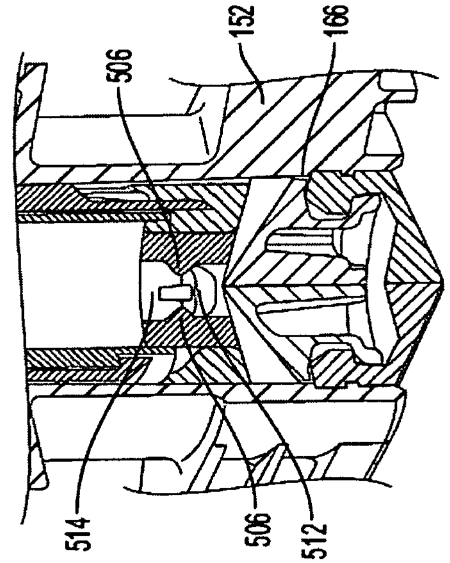
FIG. 11B is a cross-sectional view of the plug retainer of FIG. 11A in the unactivated position within an exemplary port assembly.
Figure 11A:
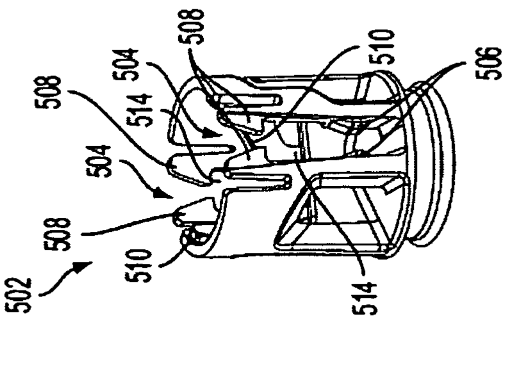
FIG. 11A is an isometric view of another exemplary plug retainer that may be used with the system shown in FIG. 1.

In another embodiment of the plug retainer shown in FIGS. 11A-11C, the plug retainer 502 includes two body pins 504, each having two distally located snap features 506 and two proximally located snap features 508. In addition, like the embodiment described above, the plug retainer 502 includes two angled surfaces 510 that interact with the two angled surfaces 186 of the actuator 160 during activation of the system in the same manner as described above. In the pre-activated state, as shown in FIG. 11B, the distally located snap features 506 are located just above latch features 512 of the port housing 152. The latch features 512 are located on opposite sides of the inner surface of the bore 166 of the port housing 152. As described above, during activation of the system, the actuator 160 forces the plug retainer 502 in the distal direction. This distal movement causes the two distally located snap features 506 to interact with the latches 512 of the port housing thereby causing the body pins 504 to flex until the snap features 506 disengage and move past the latches 512. As the actuator 160 continues to rotate, the plug retainer 502 continues to move in the distal direction until the proximally located snap features 508 come into contact with the latch features 512, as shown in FIG. 11C, thereby preventing further distal displacement of the plug retainer 502. The system is now in its activated state. In this embodiment, the combination of the slots 514 defined by the body pins 504 and the latches 512 on the inner surface of the bore 166 of the port housing 152 ensure that the plug retainer 502 is rotationally fixed within the port housing 152 but free to move axially.

As noted above, and as shown for example in FIGS. 5B and 8A-8C, the main body 148 of the port assembly 106 includes a collar 150 by which a user can rotate the main body 148. As shown, the collar 150 is an annular feature having a consistent outer surface. In alternative embodiments the outer surface may include depressions and/or ridges that enable a user to easily grab and rotate the main body 148. The main body 148 is rotatably engaged to the port housing 152 by any engagement features known in the art that allow the main body 148 to rotate relative to the port housing 152. In one embodiment, the engagement features include an annular flange 167 on the outside surface of the wall 168 of the port housing 152 that engages an annular recess (not shown) on an inner surface of the activation collar 150 to allow rotation but prevent axial disengagement between the main body 148 and the port housing 152.

The main body 148 also includes a proximally facing annular sealing surface 220 that is configured to abut a distal surface of the vial 108 (e.g., the distally facing surface of the annular flange 119) and/or body cap 110 of the first container 102 when the first container 102 is docked to the port assembly 106. This sealing engagement helps to prevent any diluent and/or medicament from escaping out of the fluid flow path established between the first and second containers 102, 104 during use.

As shown, the main body 148 includes multiple resilient retention tabs 192 that are configured to engage the annular flange 132 of the first container 102 to dock the first container 102 to the port assembly 106. As shown, the tabs 192 extend distally and radially inward from the proximal end of the main body 148 such that they are positioned within the cavity 147 of the main body 148. In the embodiment shown in FIGS. 4A-5B, there are four tabs 192 substantially equally spaced around the axis of the main body 148. However, any number of tabs 192, for example, two, three or four, are appropriate as long as they secure the first container 102 to the port assembly 106. In one embodiment, the main body 148 includes a single, resilient annular ring that uniformly collars and engages the entire annular flange 132 of the first container 102.

The tabs 192 may be constructed of a flexible material to allow the tabs 192 to be flexed when the first container 102 is inserted into the port assembly 106, and to thereafter allow the tabs 192 to spring back into their original position once the annular flange 132 of the first container 102 passes the distal end of the tabs 192, thereby securely docking the first container 102. Accordingly, the tabs 192 allow the first container 102 to be inserted into the port assembly 106 but prevent removal of the first container 102 from the port assembly 106 after the distal end of the first container 102 is inserted a predetermined distance into the cavity 147. This predetermined distance corresponds to the insertion required for the tabs 192 to engage the annular flange 132 of the first container 102. By preventing removal of the first container 102 from the port assembly 106, drug tampering, contamination, and accidental discharge of the contents is prevented.

In one embodiment, the port assembly 106 includes a hanger 156 for conveniently hanging the system on an appropriate device (e.g., pole, rack or stand). When the port assembly 106 is in a non-activated condition, the hanger 156 is not accessible to the user (e.g., nurse). Upon activation of the system, the hanger 156 transitions from the non-activated non-hanging condition to an activated hanging condition which releases the hanger 156 and presents it for proper use, rendering it is operable by the user. In one embodiment, the release of the hanger 156 and the establishment of fluid communication occur simultaneously. For instance, the hanger is operable only when fluid communication between the first container and the second container has been established.

As shown best in FIG. 5B, the hanger 156 is provided at a gap in the side wall 188 of the collar 150 and is attached to the main body 148 via a hinge 190 (e.g., a living hinge, a pin hinge, or any other hinge known in the art). As shown best in FIG. 5C, a wall 168 defining the cavity 164 overlaps itself so as to provide a partially circumferential guide slot 170 for housing the hanger so that the hanger is at least partially positioned within the slot prior to activation and for guiding the hanger 156 from a non-activated non-hanging condition to the activated hanging condition when the main body 148 is rotated relative to the port housing 152 from a first position to a second position and fluid communication between the first container and the second container has been established. The amount of rotation needed to release the hanger 156 from the guide slot 170 and activate the system can vary, and in particular, may be between about 120-200 degrees.

Figure 8C:
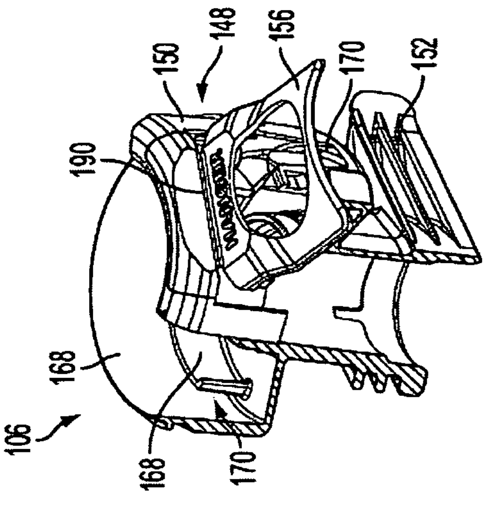
FIG. 8C is a partial cross-sectional isometric view of the portion of the port assembly of FIG. 8A after activation when the hanger is in an activated hanging configuration.

The hinge mechanism 190 may include a spring or be composed of a resilient material that biases the hanger 156 away from the main body 148 when the hanger 156 is released from the port housing 152 upon activation of the system. Accordingly, when the main body 148 is sufficiently rotated, the biasing force causes the hanger 156 to pivot away from the main body 148 so that the hanger is operable and the system can be easily hung for use as shown in FIGS. 5B and 8C. In embodiments where the hinge does not include a spring, once the main body 148 is sufficiently rotated, the hanger 156 is made available (i.e., the hanger is in the activated hanging condition) for a user to manually manipulate for hanging.

Figure 12A:
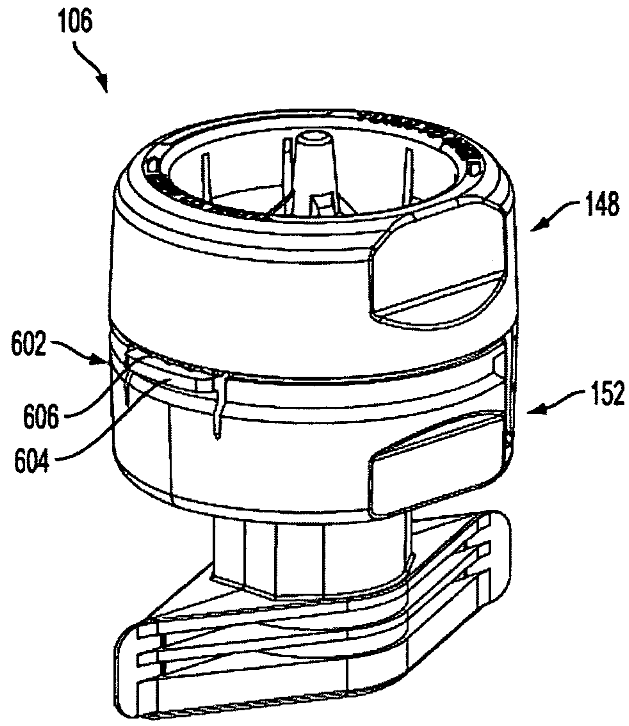
FIG. 12A is an isometric view of another exemplary port assembly that may be used with the system shown in FIG. 1, where the port assembly has a locking mechanism.
Figure 12B:
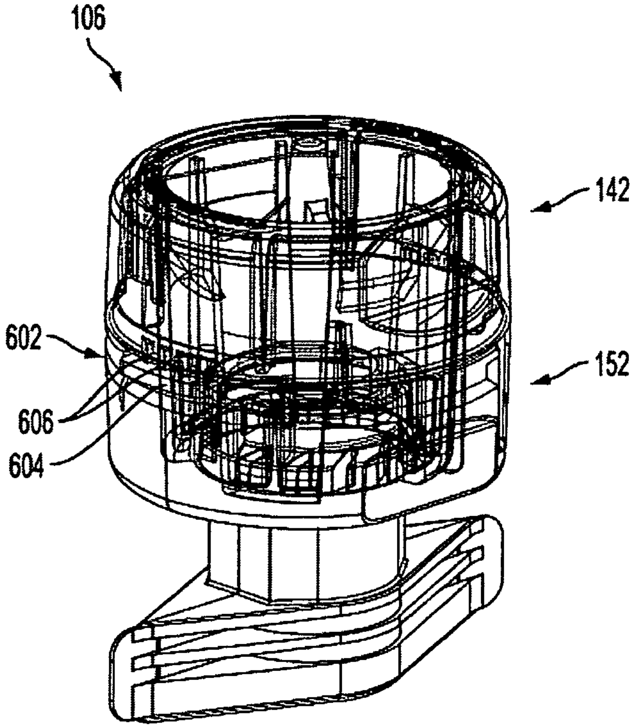
FIG. 12B is a semi-transparent isometric view of the port assembly shown in FIG. 12A.
Figure 13A:
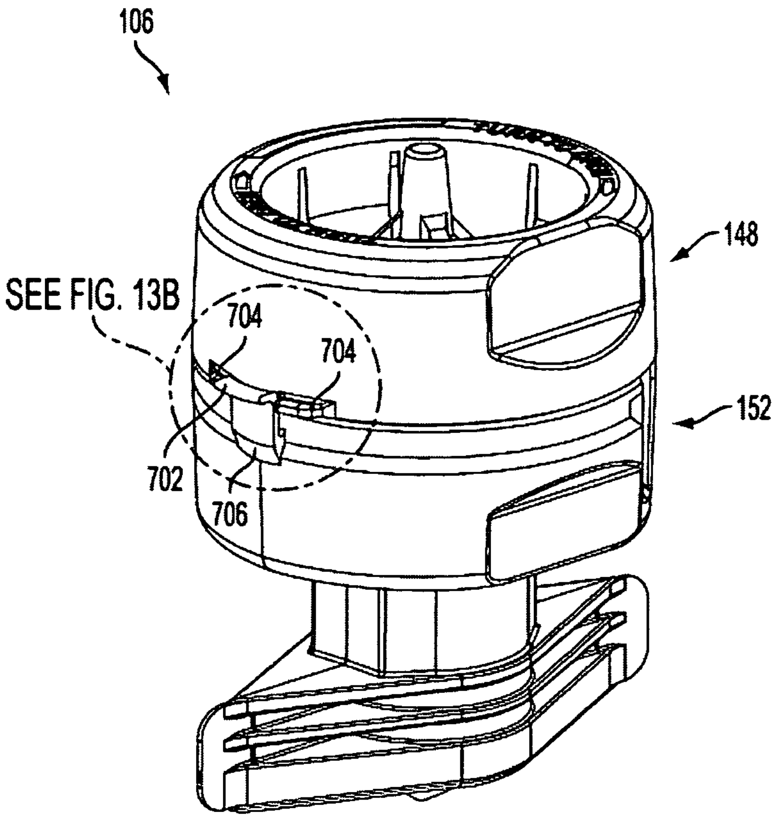
FIG. 13A is an isometric view of another exemplary port assembly that may be used with the system shown in FIG. 1, where the port assembly has another exemplary locking mechanism.
Figure 13B:
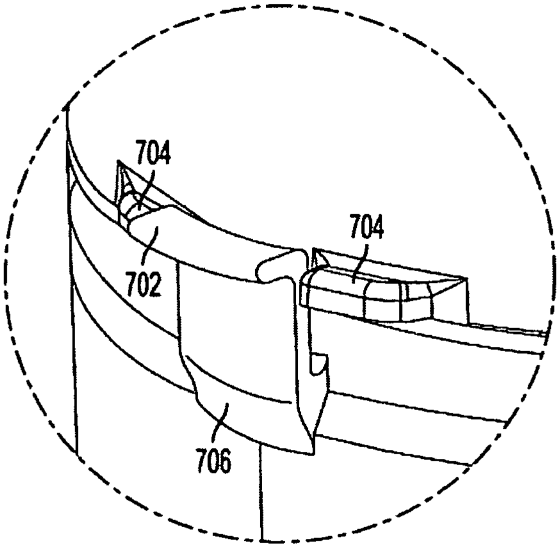
FIG. 13B is a zoomed-in isometric view of the locking mechanism shown in FIG. 13A.
Figure 14A:
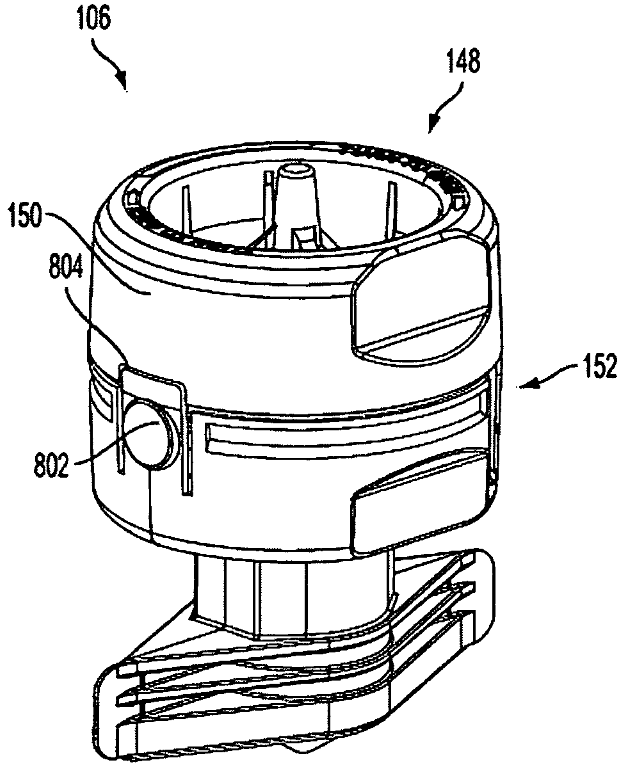
FIG. 14A is an isometric view of another exemplary port assembly that may be used with the system shown in FIG. 1, where the port assembly has another exemplary locking mechanism.
Figure 14B:
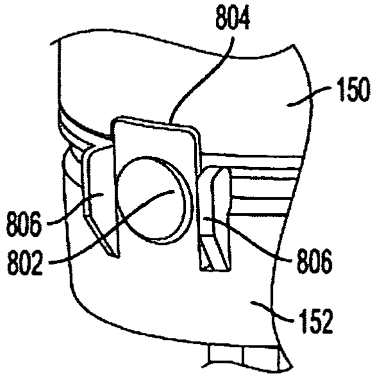
FIG. 14B is a zoomed-in isometric view of another exemplary port assembly that may be used with the system shown in FIG. 1, where the port assembly has another exemplary locking mechanism.

Turning now to FIGS. 12A and 12B, the port assembly 106 may be provided with a locking mechanism 602 that prevents inadvertent rotation between the main body 148 and the port housing 152. This helps prevent discharge of the contents of the second container 104 into the environment before the first container 102 is docked to the port assembly 106 and also prevents inadvertent/premature mixing of the contents of the containers after docking. In one embodiment, the port housing 152 may be provided with a tab 604 having ratchet teeth 606 that engage complimentary ratchet teeth (not shown) on an inside surface of the collar 150 of the main body 148. To unlock the port housing 152 from the main body 148, a user pushes the tab 604 radially inward thereby disengaging the ratchet teeth 606. In an alternative embodiment, as shown in FIGS. 13A and 13B, the port housing 152 may be provided with a tab 702 that is rotationally constrained by two protrusions 704 of the main body 148. To unlock the port housing 152 from the main body 148, a user pushes down on the tab 702 thereby causing the tab 702 to rotate downward about its base 706 to a position in which the tab 702 is no longer constrained by the protrusions 704, thereby allowing the main body 148 to rotate relative to the port housing 152. In yet another embodiment, as shown in FIGS. 14A-14B, the port housing 152 may be provided with a tab 802 that is rotationally constrained by a cutout 804 in the collar 150 of the main body 148. To unlock the port housing 152 from the main body 148, a user pushes the tab 802 radially inward until the tab 802 is located radially inward from the wall of the collar 150, thereby allowing the main body 148 to rotate relative to the port housing 152. To further prevent inadvertent rotation of the main body 148 relative to the port housing 152, the tab 802 may be protected by barriers 806 that extend radially outward form the side wall of the port housing 152. These barriers 806 help ensure that the tab 802 is intentionally depressed only when the system is ready for activation.

Figure 17A:
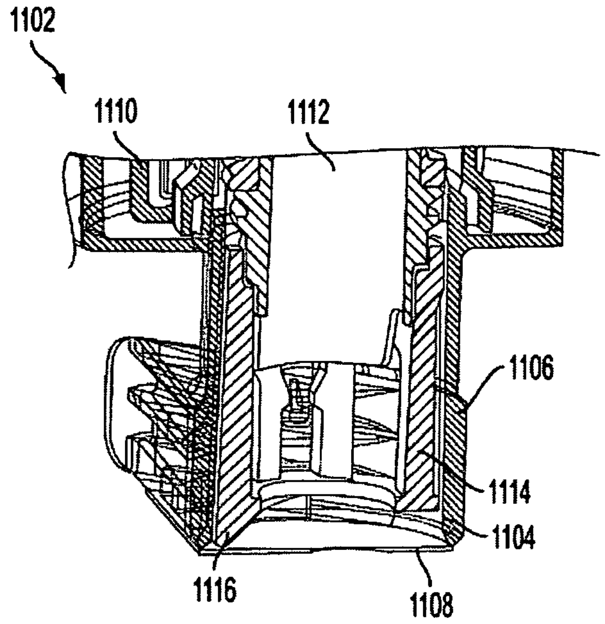
FIG. 17A is a cross-sectional view another exemplary port assembly that can be used in the system shown in FIG. 1.

In another embodiment of the port assembly 1102, as shown in FIG. 17A, the distal end of the bore 1104 of the port housing 1106 is sealed with a septum or film 1108 instead of a plug stopper 174 as described above. In such an embodiment, fluid communication is established between the first and second containers when the septum or film 1108 is ruptured during activation (i.e., rotation of the main body 1110/actuator 1112). In one such embodiment, a cutting member 1114 may be fixed to the actuator 1112, which is in turn fixed to the main body 1110 such that rotation of the main body 1110 causes corresponding rotation of the actuator 1112 and cutting member 1114. Alternatively, the actuator 1112 and cutting member 1114 may be manufactured as a single unitary component. In an embodiment where the actuator 1112 and cutting member 1114 are two separate components, the actuator 1112 may be fixed to the cutting member 1114 using any known technique in the art.

Figure 17B:
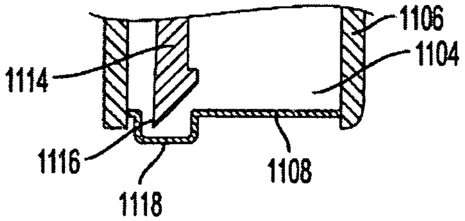
FIG. 17B is a zoomed-in cross-sectional view of the cutting edge and septum of the port assembly shown in FIG. 17A.

Located at the distal end of the cutting member 1114 is a cutting edge 1116. As shown in FIG. 17B, the cutting edge 1116 may be located within a pocket or depression 1118 of the septum or film 1108 prior to rotation of the main body 1110. After docking the first container to the second container, a user rotates the main body 1110, which causes the cutting edge 1116 to undergo corresponding rotation thereby exiting the pocket or depression 1118 and slicing the septum or film 1108 which in turn provides fluid communication between the first and second containers. Unlike the embodiments described above, the actuator and cutting member do not need to have compatible cam-like surfaces nor is there a need for any splined engagement with the port housing because the rotary motion of the actuator does not need to be translated into linear motion of the cutting member. Instead, the combination of the actuator 1112 and cutting member 1114 needs to rotate with the main body 1110 but relative to the port housing 1106. With the exception of this significant difference, it should be understood, that many of the other features described above with respect to the embodiments are equally applicable to this embodiment. However, in another embodiment, it is possible to include compatible cam-like surfaces on the distal end of the actuator 1112 and proximal end of the cutting member 1114 in a similar manner as that described above. In such an embodiment, a splined engagement may be provided between the port housing 1106 and cutting member 1114. Accordingly, as the user rotates the main body 1110, the actuator 1112 undergoes corresponding rotation which causes the cutting member 1114 to be axially displaced in the distal direction. Such axial displacement causes the cutting edge 1116 to penetrate the septum or film 1108 thereby providing fluid communication between the first and second containers. In such an embodiment, the septum or film 1108 does not need to be provided with a pocket 1118.

Figure 18A:
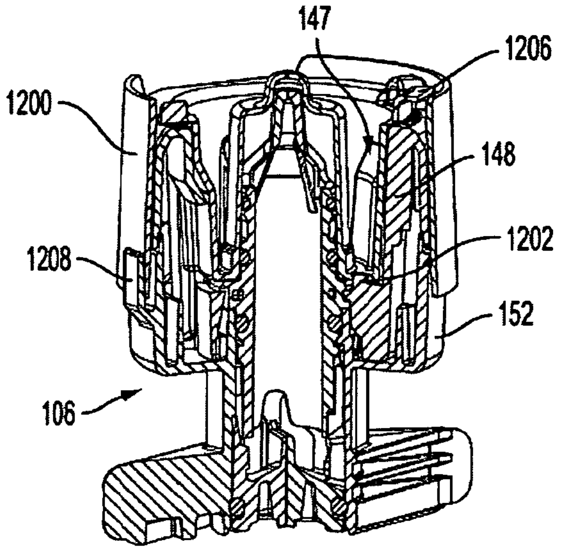
FIG. 18A is a partial cross-sectional isometric view of an exemplary cover for a port assembly that may be used with the system shown in FIG. 1.
Figure 18B:
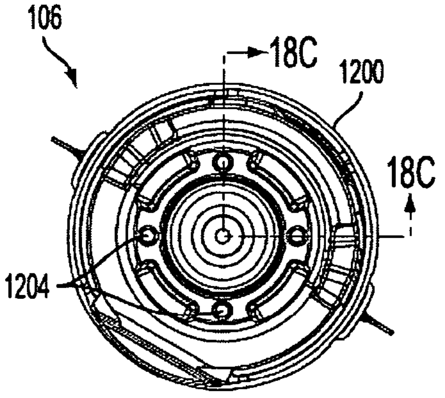
FIG. 18B is a top view of the cover shown in FIG. 18A.
Figure 18C:
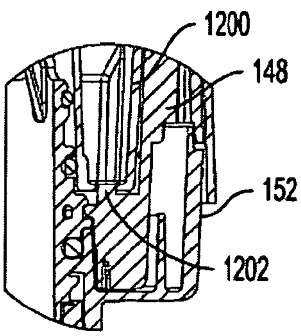
FIG. 18C is a zoomed in view of a post in its undeformed state for attaching the cover shown in FIG. 18A to a port assembly.

The port assembly 106 may be provided with a tamper evident cover that protects the proximal cavity 147 of the port assembly. As shown in FIGS. 18A-C, the tamper evident 1200 cover is contoured to the port assembly 106 and is configured to completely surround the main body 148 and at least a portion of the port housing 152. To secure the tamper evident cover 1200 to the port assembly 106, the main body 148 may be provided with a plurality of attachment posts 1202 that are configured to fit within a corresponding number of post holes 1204 in the tamper evident cover 1200. Any number of posts 1202 and corresponding holes 1204 may be used.

To secure the tamper evident cover 1200 to the port assembly 106, the posts 1202 are aligned with the holes 1204 and then the tamper evident cover 1200 is seated within the proximal cavity 147. Once the tamper evident cover 1200 is completely seated, the attachment posts 1202 are deformed using ultrasonic staking or any other suitable known method in the art. Such deformation locks the tamper evident cover 1200 in place. To remove the cover 1200, a user pulls up on the pull tab 1206 provided near the proximal end of the cover 1200. After the cover 1200 has been removed, either the holes 1202 or the poles 1204, or both, are fractured and/or deformed, which provides evidence of tampering.

In addition to being attached to the main body 148 via the posts 1202, the tamper evident cover 1200 may be engaged to the port housing 152 via a slotted engagement 1208, where a portion of the tamper evident cover 1200 extends into a slot (or groove) of the port housing 152. This slotted engagement 1208 may prevent rotation of the tamper evident cover 1200 and the main body 148, which helps to ensure that the port assembly 106 is not unintentionally activated.

Figure 6A:
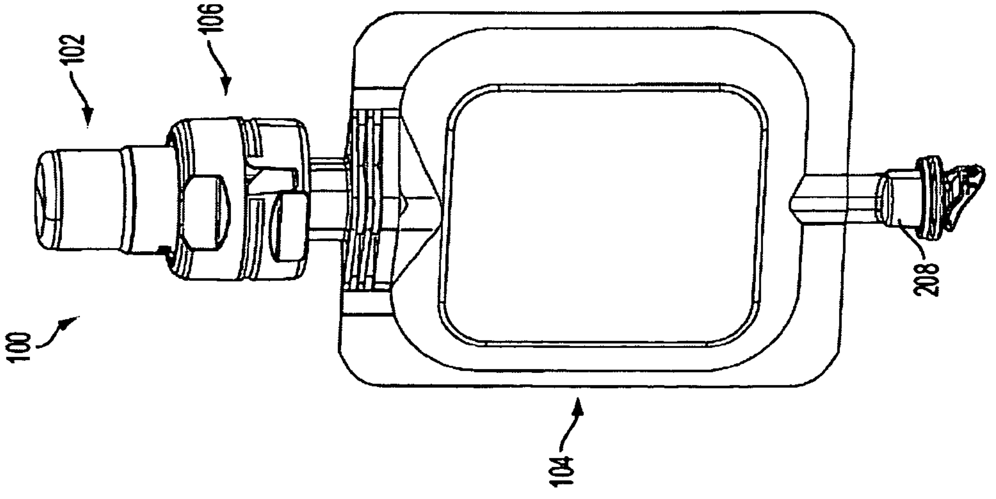
FIG. 6A is an isometric view of the system shown in FIG. 1 in the docked position.
Figure 7B:
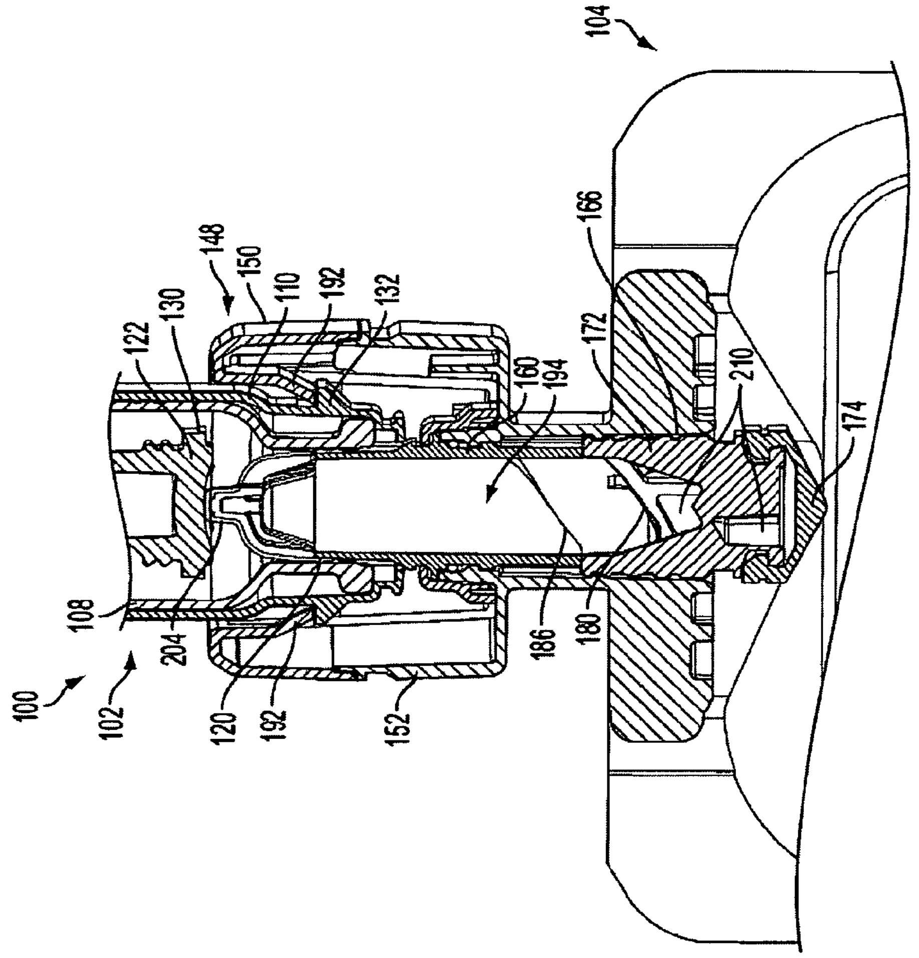
FIG. 7B is a cross-sectional view of the system shown in FIG. 7A.
Figure 7A:
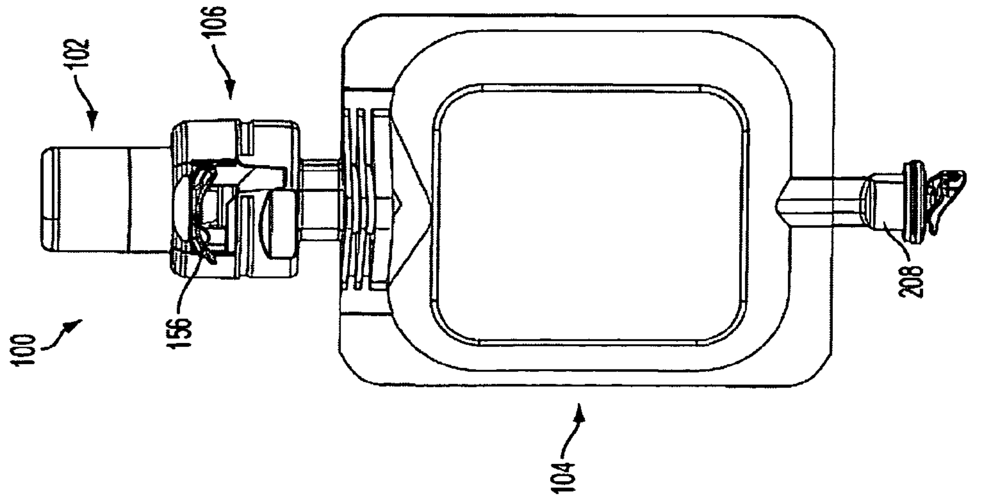
FIG. 7A is an isometric view of the system shown in FIG. 1 in the activated position.

In accordance with a method of the present invention, a user can mix the contents of two containers following a simple two-step process. First, the first container 102 is docked to the port assembly 106 of the second container 104, as shown in FIGS. 6A-6B. Second, following the docking step, the system 100 is activated, which places the cavities of the containers 102, 104 in fluid communication, as shown in FIGS. 7A-7B. The simple two-step process helps to ensure the proper medication dose and can prevent errors associated with the preparation and delivery of medication.

In addition, the method of the invention includes the prevention of errors in the delivery of intravenous medicaments by preventing the use of a hanger associated with the system 100 when the first container and the second container are not in fluid communication. The system can be configured to allow use of the hanger only when the first container and the second container are in fluid communication, which can prevent an error such as a provider administering only the contents of the diluent container without the contents of the medicament container.

In one embodiment, the first container 102 holds a medicament and can be maintained separate from the second container 104 that holds a diluent until, for example, the medicament is requested by a doctor. After a prescription for the medicament is ordered, a pharmacist or other healthcare worker will locate the first container 102 containing the requested medicament and remove the top cap 114 from the body cap 110. The pharmacist or other healthcare worker will also remove the cap 162 from the port assembly 106 of the second container 104. The first container 102 can now be "docked" to the port assembly 106, typically in the pharmacy, by pushing the stoppered end of the first container 102 into the port assembly 106, as shown in FIGS. 6A-6B.

When the first container 102 is moved axially into the port assembly 106, the annular flange 132 of the body cap 110 contacts the retention tabs 192 of the main body and flexes the tabs 192 radially outward to allow the flange 132 to move past the tabs 192. After the flange 132 passes the distal most point of the tabs 192, the tabs 192 will spring back to their original, unflexed positions, thereby locking the first container 102 in the docked position. During this docking step, the tip 204 of the actuator 160 forces the stopper 122 of the first container 102 into the internal cavity of the first container 102, thereby bringing the flow passageway 194 of the actuator 160 into fluid communication with the contents of the first container 102. In one embodiment, during the docking step, the stopper 122 is forced into the cavity of the first container 102 prior to the tabs 192 springing back to their original unflexed positions.

In order to ensure that the actuator 160 is able to push the stopper 122 completely into the cavity of the first container 102, the tip 204 of the actuator 160 is sufficiently long and narrow enough so that when the stopper flange 130 folds upward while being pushed into the first container 102, such upward folding does not interfere with the insertion of the actuator 160 into the opening 120/neck 118 of the first container 102. In other words, the tip 204 of the actuator 160 should be configured such that the stopper flange 130 does not become wedged between the actuator 160 and the wall of the opening 120/neck 118 as it folds upwards.

Figure 19C:
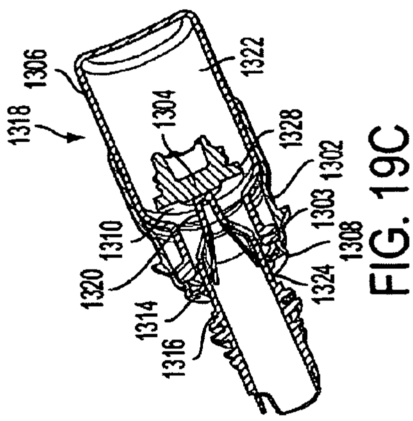
FIG. 19C is a cross-sectional view of the first container shown in FIG. 19A, where the actuator is in the activated position.
Figure 19E:
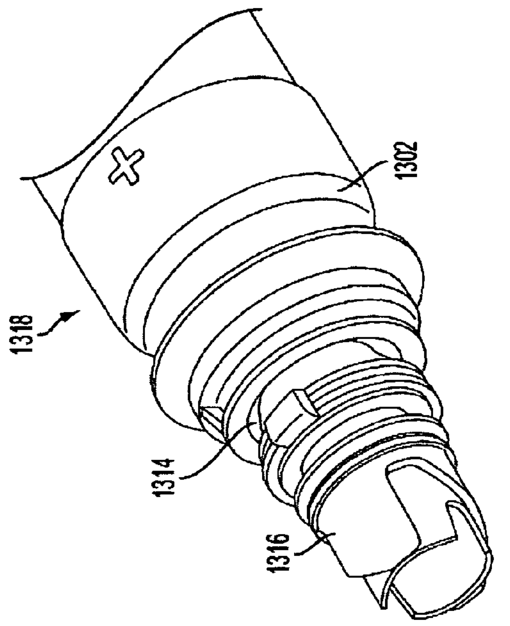
FIG. 19E is another isometric view of the first container shown in FIG. 19A, where the actuator is in the activated position.
Figure 19B:
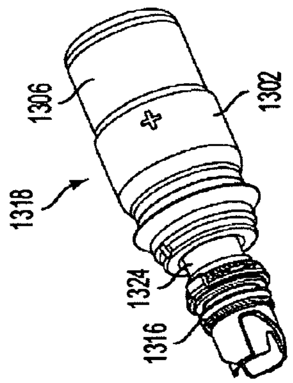
FIG. 19B is another isometric view of the first container shown in FIG. 19A, where the actuator is in the activated position.
Figure 19A:
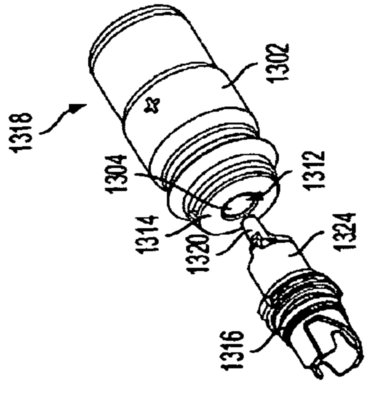
FIG. 19A is an isometric view of another exemplary first container that can be used in the system shown in FIG. 1, where the actuator is in the unactivated position.
Figure 19D:
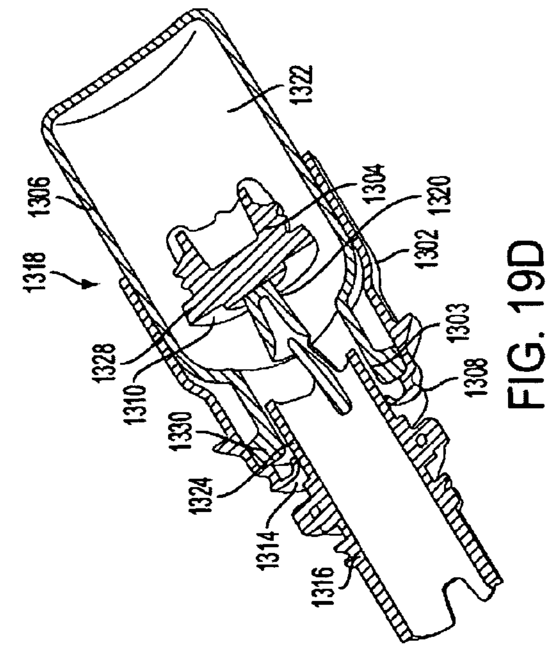
FIG. 19D is another cross-sectional view of the first container shown in FIG. 19A, where the actuator is in the activated position.

In an embodiment where the distal end of the body cap 1302 extends radially inward over a portion the opening of the vial 1306 and the top surface 1310 of the stopper 1304, as shown in FIGS. 19A-E, the pharmacist or other healthcare worker removes the top cap, aligns the actuator tip 1320 with the opening 1312 formed by the radially inward extending portion 1314, and then docks the first container 1318 to the port assembly of the second container. During this docking step, the actuator tip 1320 contacts the exposed portion of top surface 1310 of the stopper 1304 and then as the actuator 1316 passes through the opening 1312 it forces the stopper 1304 of the first container 1318 into the internal cavity 1322 of the first container 1318, as shown in FIGS. 19C-D.

Because of the elastic/resilient properties of the radially inward extending portion 1314 of the body cap 1302 and the fact that the diameter of the opening 1312 is less than the diameter of the body portion 1324 of the actuator 1316, docking causes the radially inward extending portion 1314 of the distal end of the body cap 1302 to form a fluid seal with the body portion 1324 of the actuator 1316 when the first container 1318 is docked to the port assembly of the second container. In addition, as shown in FIGS. 19B-E, the inwardly extending portion 1314 of the distal end of the body cap 1302 is bent towards or into the opening of the vial 1306 as the first container 1318 is docked to the port assembly. Such bending is achievable due to the void left from where the flange 1328 of the stopper 1304 engaged the shoulder 1330 of the vial 1306 prior to docking.

The configuration and material of the stopper 122 should be selected such that the force required to push stopper 122 into the interior of first container 102 during docking (i.e., the “push-in force”) is appropriate in view of the mechanical strength of the system and ergonomics. It will be appreciated that the stopper push-in force should be great enough to prevent inadvertent docking while simultaneously being small enough to permit both (i) the various components of the system to be constructed of relatively low-cost materials and (ii) a clinician to readily dock the first container 102 to the port assembly 106. In one embodiment, the stopper push-in force is in the range of about 4-20 pounds of force. In another embodiment, the stopper push-in force is in the range of about 5-15 pounds of force. In a further embodiment, the stopper push-in force is in the range of about 8-13 pounds of force.

As the flange 132 of the first container 102 is forced past the tabs 192, the pharmacist or healthcare worker will typically hear an audible “pop,” signaling that the flange 132 has passed over the tabs 192 and that the first container 102 is docked. As noted above, in this position, the tabs 192 preclude reverse axial movement and thus do not allow the first container 102 to be intentionally or unintentionally removed/undocked from the port assembly 106, thereby preventing possible tampering.

In the docked but unactivated state, as shown in FIGS. 6A-6B, the first container 102 is open but the contents of the first container 102 remain separate from the contents of the second container 104; however, the first container 102 is fixed to the port assembly 106 of the second container 104 and as noted above, cannot be removed therefrom without generally destroying various of its components. Thus, at this point, the first container 102 is mechanically connected to the port assembly 106 but is not yet in fluid communication with the second container 104. The two containers 102, 104 can remain in the docked state without activating the system 100 and mixing the contents for an extended period typically limited only by the shelf life of the contents in the two containers 102, 104. At any time after the first container 102 is docked to the port assembly 106, a nurse or other healthcare worker can activate the system 100, thereby enabling mixing of the contents in the first container 102 with the contents in the second container 104.

Referring now to FIGS. 7A-7B, to activate the system 100, a user grips the collar 150 of the main body 148 of the port assembly 106 and rotates (either clockwise or counterclockwise depending on design) it a predetermined amount relative to the port housing 152 from a first position to a second position. As noted above, the predetermined amount of rotation can vary. In one embodiment, the rotation required to activate the system 100 is between 120-200 degrees. If the port assembly 106 includes a lock mechanism that prevents the main body 148 from rotating relative to the port housing 152, then the user must unlock the assembly 106 before rotating the main body 148. Various locking mechanisms have been described above with reference to FIGS. 12A-14B.

As the user rotates the main body 148, the actuator 160 undergoes corresponding rotation, which causes the distal angled surfaces 186 of the actuator 160 to cooperate with the proximal angled surfaces 180 of the plug retainer 172 in cam-like fashion. Because the actuator 160 is fixed axially while the plug retainer 172 is free to move axially but rotationally fixed via the splined engagement described above, the plug retainer 172 is forced in the distal direction. As the plug retainer 172 moves in the distal direction so does the plug stopper 174 that is attached thereto, thereby placing the cavity of the second container 104 into fluid communication with the cavity of the first container 102. At this point the contents of the containers can be mixed. When the user has sufficiently rotated the main body 148 such that the system 100 is activated, the inlet/outlet windows 210 of the plug retainer 172 are located at least partially within the cavity of the second container 104 so that the contents of the containers are free to flow into and out of the flow path created by the bore 182 of the plug retainer 172, the bore 166 of the port housing 1652, and the flow passageway 194 of the actuator 160.

The main body 148 and or port housing 152 may include features that lock the system 100 in the activated (second) position after rotation. Further, these features may provide an audible or tactile signal to the user that the system has been activated. Thus, the user will be alerted when the system 100 is activated and the user will not continue to rotate the main body 148, thereby preventing possible damage to the system 100. Even further, the activation collar 188 of the main body 148 may include a window in which a visible signal may be viewed when the system is in the activated state.

Depending on the orientation of the system 100 and the characteristics of the contents, mixing may immediately commence without assistance from the user. However, in order to sufficiently mix the contents, the user may have to invert or tip the system 100, shake the system 100, and/or squeeze/milk either or both of the containers 102, 104. Once the contents are sufficiently mixed, the composition may be delivered to a patient through the outlet 208. Delivery of the contents of first and second containers to the patient will require that an IV line of known construction be fluidly connected to the outlet 208 of the second container 104.

In addition to establishing fluid communication between the containers, the rotation of the main body 148 relative to the port housing from a first position that prevents fluid communication to a second position that establishes fluid communication, places the hanger 156 of the port assembly 106 in an activated hanging condition, as shown best in FIGS. 7A and 8C. As the main body 148 rotates (see FIG. 8B), the hanger 156 slides along the guide slot 170 formed by the overlap of the side wall 168 of the port housing 152. Near or at the end of rotation, the hanger 156 exits the circumferential guide slot 170. The system can now be hung, perhaps on a standard IV stand. In the hanging position, the first container 102 should be above the second container 104 so that any contents of the first container 102 that are not mixed or reconstituted with the contents of the second container 104 will tend to flow (due to gravity) into the second container 104. In some embodiments, the port housing includes antirotational members that limit or prevent rotation from the second position to the first position.

As noted above, an additional aspect of one embodiment of the two-component mixing system described herein, is that after the top cap 114 is removed from the body cap 110, the contents of the first container 102 can be accessed with a syringe needle or cannula to either remove some of the contents thereof, add a small amount of diluent to the contents thereof, or a combination of adding contents and removing contents from the first container 102. To perform such operations, the pharmacist or other healthcare worker may pierce the stopper 122 with the needle of a syringe to access the cavity of the first container 102. In this embodiment, the first container 102 can be used as a standard pharmaceutical vial (i.e., a vial that is accessed using a hypodermic needle associated with a syringe) or as a component of the two-component mixing system. Stopper 122 may be constructed of a polymeric material that is resistant to coring when a hypodermic syringe needle is pushed therethrough.

The configuration and material of stopper 122 may be selected such that the force required to push a hypodermic syringe needle therethrough is ergonomically acceptable to clinicians. In one embodiment, the force required to pierce stopper 122 with a hypodermic syringe needle is less than 1.5 pounds of force. In an alternative embodiment, the force required to force a hypodermic syringe needle through stopper 122 is in the range of about 0.5-1.0 pounds of force. It is desirable that the material used to construct the stopper 122 be a material that is inert to the intended contents of first container 102. Where first container 102 is intended to contain a medicament, the material of construction of the stopper 122 is ideally a material that is already approved by regulatory agencies for use with the medicament, thereby minimizing or eliminating the need to undertake extensive compatibility testing to ensure that there is no undesirable interaction between the medicament and the stopper 122.

FIGS. 20A-24F illustrate another embodiment of a port assembly 1400 that can be used to mix the contents of two separate containers. As shown best in FIG. 20F, the port assembly 1400 generally comprises four components: (i) a port housing 1402 with an integral actuator 1404, (ii) an actuator seal 1406, (iii) a main body comprising a retainer 1408 and an activation collar 1410, and (iv) a hanger 1412 (partially shown in FIG. 20E). The retainer 1408 of the main body is configured to receive and engage a first container 102 such that the first container 102 can be securely docked to the assembly 1400 without dislodging the stopper 122 from the opening/neck 120/118 of the first container 102. FIG. 20F shows the first container 102 in the docked position in the port assembly 1400 but does not show the specific features of the first container 102. To activate the system after docking the first container 102, a user rotates the activation collar 1410 of the main body relative to the port housing 1402, which causes the retainer 1408 to rotate and move axially in the distal direction relative to the port housing 1402. As the retainer 1408 moves in the distal direction, (1) the actuator 1404, which is axially fixed in the port housing 1402, forces the stopper 122 out of the opening/neck 120/118 of the first container 102 and into the cavity of the first container 102, and (2) the actuator seal 1406 (which is attached to the retainer 1408) slides distally past the openings 1414 in the actuator 1404, thereby establishing fluid communication between the first and second containers 102, 104 via the fluid passageway 1416 of the actuator 1404.

As noted above, in the port assembly 1400 shown in FIGS. 20A-24F, the first container 102 can be docked to the port assembly 1400 without dislodging the stopper 122 of the first container 102 from the opening/neck 120/118 of the first container 102. Accordingly, when the first container 102 is docked to the port assembly 1400, the actuator tip 1442 is positioned slightly below the stopper 122, or in some embodiments such as the one shown is FIG. 20F, the actuator tip 1442 may actually contact the stopper 122 without dislodging the stopper 122 from the opening/neck 120/118 of the first container 102. This may be beneficial because it allows the first container 102 to be docked to the second container 104 without exposing the medicament in the first container 102 to the outside environment. Therefore, the shelf life of the medicament is not compromised.

In the embodiment of the port housing 1402 shown in FIGS. 21A-E, the distal portion 1418 of the port housing 1402 serves as a mount for a second container 104. As shown, the distal portion 1418 of the port housing 1402 has a semi-elliptical outer shape, which assists in sealing a second container 104 to the port housing 1402. Any known sealing technique in the art may be used such as heat sealing, RF welding, or a blow-fill-seal procedure. In other embodiments, the second container 104 may mounted directly to the cylindrical outer surface 1420 of the port housing 1402. In such an embodiment, the port housing 1402 may not include a distal portion 1418 with a semi-elliptical outer shape. Instead, the port housing 1402 may terminate at the distal end 1422 of the cylindrical portion 1420 of the port housing 1402.

The proximal end of the port housing 1402 is configured to rotatably attach to the activation collar 1410 using any engagement features known in the art that allow the activation collar 1410 to rotate relative to the port housing 1402. In the embodiment shown in FIGS. 20F, 21E, and 24F, the engagement features includes an annular recess 1424 on the outside surface 1426 of the outer annular lip 1428 of the port housing 1402 that engages annularly spaced protrusions 1430 on the inner surface 1432 of the outer annular skirt 1434 of activation collar 1410 to allow rotation but prevent axial disengagement between the activation collar 1410 and the port housing 1402. In another embodiment, the activation collar 1410 may be provided with an annular recess while the port housing 1402 is provided with annular protrusions. While a plurality of annularly spaced protrusions 1430 are shown, other embodiments may include a single annular protrusion that circumscribes the inner surface 1432 of the outer annular skirt 1434 of the activation collar 1410.

The interior of the port housing 1402 defines a threaded cavity 1436, 1480 that is open at its proximal end and configured to engage corresponding threads 1438 on the outer surface 1440 of the retainer 1408. As such, the retainer 1408 can be threaded into the port housing 1402 during activation of the system. As the retainer 1408 is threaded into the port housing 1402, the retainer 1408 moves axially in the distal direction relative to the port housing 1402.

Figure 21A:
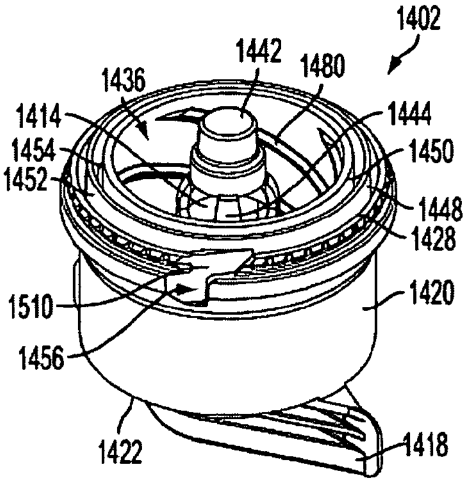
FIG. 21A is an isometric view of an exemplary port housing of the port assembly shown in FIGS. 20A-F.
Figure 21B:
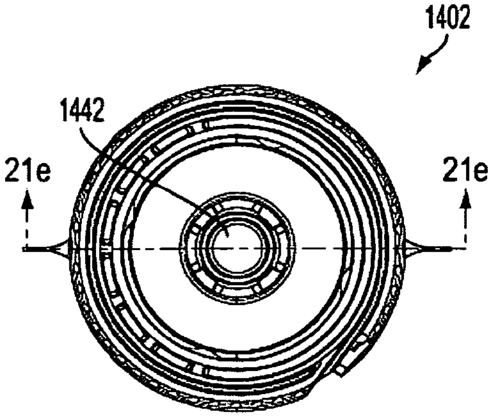
FIG. 21B is a top view of the port housing shown in FIG. 21A.
Figure 21C:
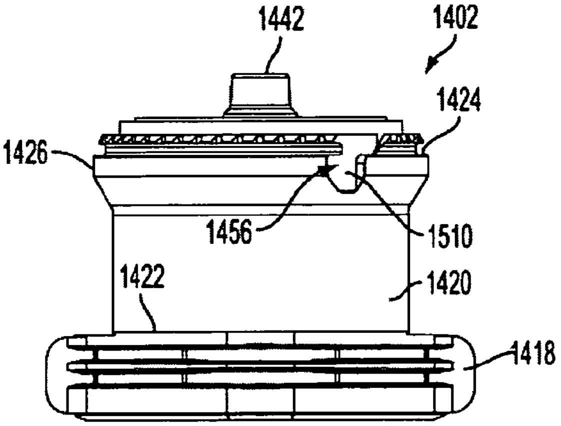
FIG. 21C is a side view of the port housing shown in FIG. 21A.
Figure 21D:
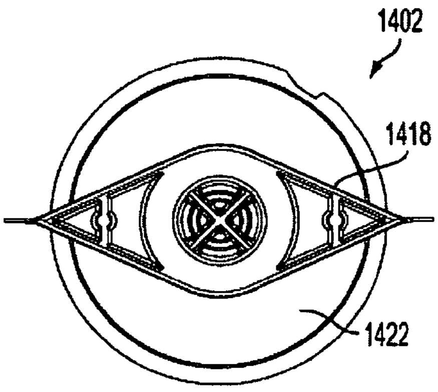
FIG. 21D is a bottom view of the port housing shown in FIG. 21A.
Figure 21E:
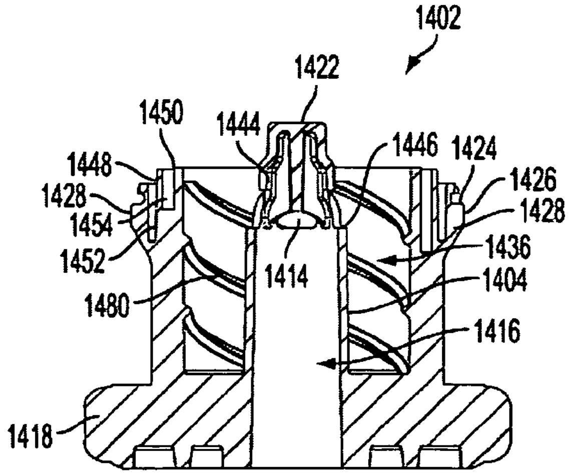
FIG. 21E a cross-sectional view of the port housing shown in FIG. 21A.

As shown best in FIG. 21E, axially aligned in the cavity 1436 of the port housing 1402 is an actuator 1404 that extends from the distal elliptical portion 1418 of the port housing 1402 past the proximal end of the port housing 1402. In embodiments that do not include a distal elliptical portion 1418, the actuator 1404 may extend from the distal portion of the cylindrical body 1420 of the port housing 1402. Additionally, in other embodiments, the actuator 1404 may terminate at or below the proximal end of the port housing 1402.

The actuator 1404 defines a flow passageway 1416 through its interior that extends from the distal end of the port housing 1402 and terminates at the openings 1414 in the actuator 1404 near the actuator tip 1442. As shown, the actuator 1404 is an integral part of the port housing 1402, however, in other embodiments, the actuator 1404 may be a separate component that is secured to (and supported axially by) the port housing 1402. In such an embodiment, the actuator 1404 may be secured to the port housing 1402 using any known connection mechanisms in the art.

The proximal portion of the actuator 1404 is formed of a plurality of sidewall members or ribs 1444 that extend from a shoulder 1446 of the actuator 1404 and terminate at the actuator tip 1442. In one embodiment, the proximal portion of the actuator 1404 comprises four ribs 1444 with openings 1414 therebetween that provide access to the flow passageway 1416. In other embodiments, a different number of ribs 1444 and openings 1414 may be used as long as the structural integrity of the actuator 1404 is such that it can force the stopper 122 of the first container 102 into the cavity of the first container 102 during activation. Additionally, the openings 1414 should allow for sufficient fluid flow such that the contents of the first and second containers 102, 104 can be easily mixed.

The outermost diameter of the ribs 1444 (i.e., where the ribs 1444 meet the actuator shoulder 1446) is approximately equal to the inside diameter of the opening 120 of the first container 102. The actuator 1404 may be constructed of a relatively rigid material so that it is capable of forcing the stopper 122 into the internal cavity of the first container 102 upon activation of the system. In one embodiment, the actuator 1404 may include one or more sealing rings (not shown) that circumscribe the outer surface of the actuator 1404 and engage the inner surface of the opening 120/neck portion 118 of the first container 102 after the actuator 1404 enters the opening 120 during activation, thereby creating a fluid seal and preventing leakage of the contents of the first container 102. In such an embodiment, the actuator 1404 may be molded according to a double-shot process where a rigid material for the actuator 1404 and a resilient material for sealing rings are molded together.

As shown best in FIGS. 21A and 21E, the proximal portion of the port housing 1402 comprises three concentric annular lips 1428, 1448, 1450 that define two annular channels 1452, 1454 therebetween. The outer channel 1452 is a circumferential guide slot that is configured to house the hanger 1412 prior to activation and to guide the hanger 1412 to the exit slot 1456 in the outer annular lip 1428. The inner annular channel 1454 is configured to receive the inner skirt 1458 and guide tab 1459 of the activation collar 1410 to provide stability and to ensure smooth rotation of the activation collar 1410 relative to the port housing 1402. The outer annular lip 1428 includes a recess 1424 that circumscribes its outer surface 1426, which as noted above, is configured to receive the protrusions 1430 on the inner surface 1432 of the outer skirt 1434 of the activation collar 1410 to allow rotation but prevent axial disengagement between the activation collar 1410 and the port housing 1402.

Figure 22A:
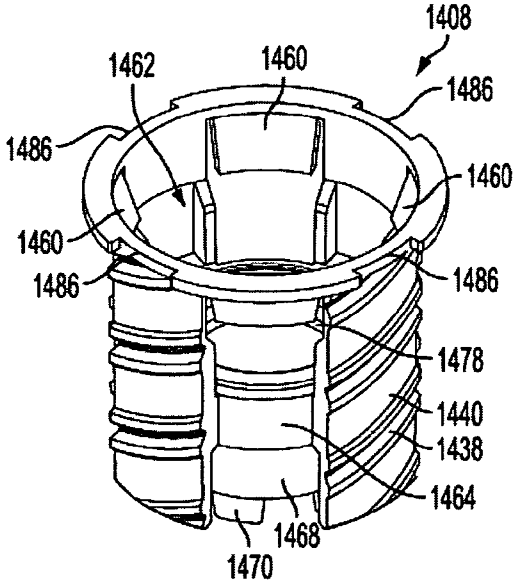
FIG. 22A is an isometric view of an exemplary retainer of the port assembly shown in FIGS. 20A-F.
Figure 22B:
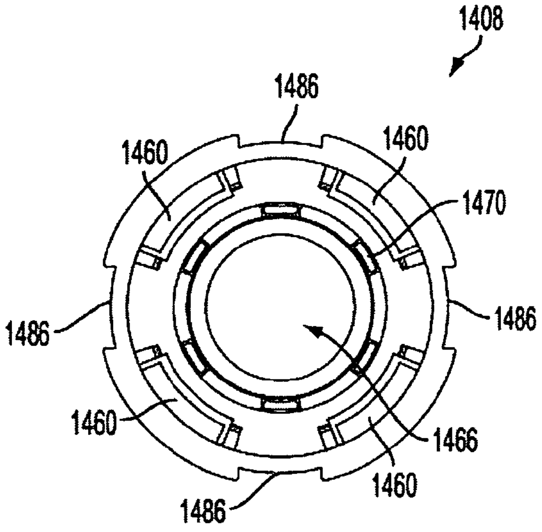
FIG. 22B is a top view of the retainer shown in FIG. 22A.
Figure 22C:
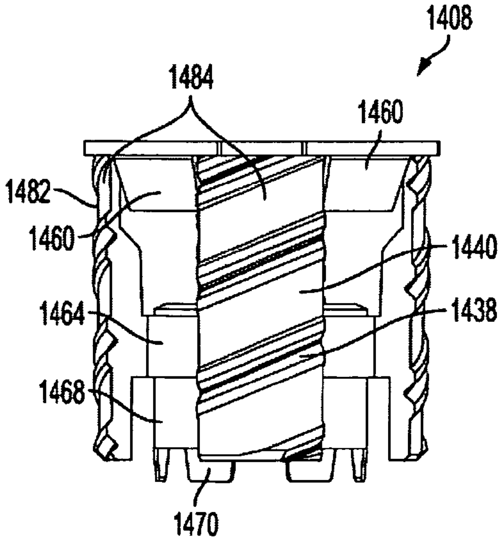
FIG. 22C is a side view of the retainer shown in FIG. 22A.

The retainer 1408 is configured to receive and dock the first container 102. As shown in FIGS. 22A-22C, the retainer 1408 includes four resilient retention tabs 1460 that are configured to engage the annular flange 132 of the first container 102 when the first container 102 is inserted into the cavity 1462 of the retainer 1408. As shown, the tabs 1460 extend distally and radially inward from the proximal end of the retainer 1408. As shown best in FIG. 22B, the four tabs 1460 are substantially equally spaced around the axis of the retainer 1408. However, any number of tabs 1460, for example, two, three or four, are appropriate as long as they secure the first container 102 to the port assembly 1400. In one embodiment, the retainer 1408 includes a single resilient annular ring that uniformly collars and engages the entire annular flange 132 of the first container 102.

The tabs 1460 may be constructed of a flexible material to allow the tabs 1460 to be flexed when the first container 102 is inserted into the port assembly 1400, and to thereafter allow the tabs 1460 to spring back into their original position once the annular flange 132 of the first container 102 passes the distal end of the tabs 1460, thereby securely docking the first container 102 to the port assembly 1400. Accordingly, the tabs 1460 allow the first container 102 to be inserted into the port assembly 1400 but prevent easy removal of the first container 102 from the port assembly 1400 after the first container 102 is inserted a predetermined distance into the cavity 1462. This predetermined distance corresponds to the insertion required for the tabs 1460 to engage the annular flange 132 of the first container 102. By preventing removal of the first container 102 from the port assembly 1400, drug tampering, contamination, and accidental discharge of the contents of the containers 102, 104 is prevented.

Figure 23A:
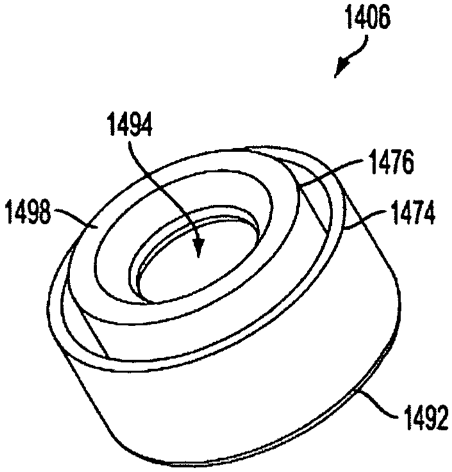
FIG. 23A is an isometric view of an exemplary actuator seal of the port assembly shown in FIGS. 20A-F.
Figure 23B:
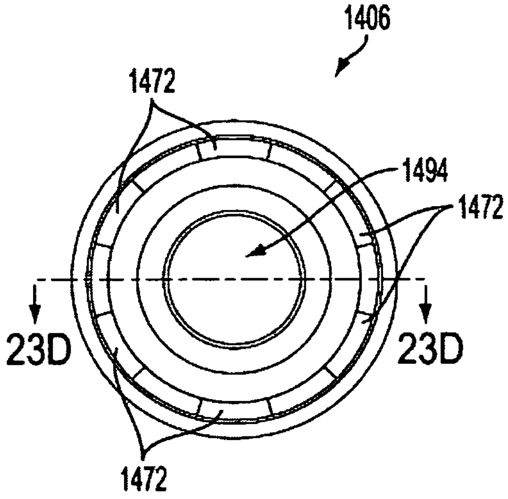
FIG. 23B is a top view of the actuator seal shown in FIG. 23A.
Figure 23C:
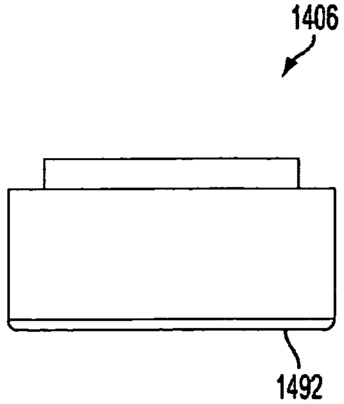
FIG. 23C is a side view of the actuator seal shown in FIG. 23A.
Figure 23D:
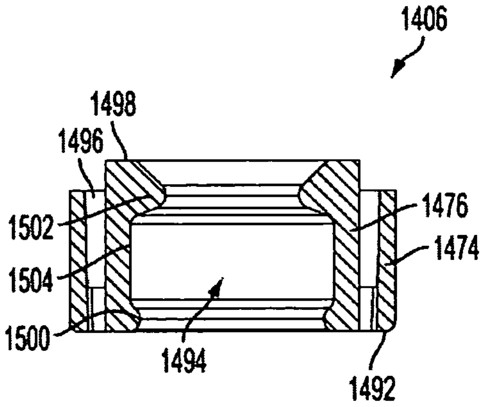
FIG. 23D is a cross-sectional view of the actuator seal shown in FIG. 23A.

The cylindrical distal portion 1464 of the retainer 1408 includes a bore 1466 that is configured to allow the retainer 1408 to move distally about the actuator 1404 during activation. The cylindrical distal portion 1464 is also configured to retain the actuator seal 1406 such that the retainer 1408 and seal 1406 rotate and move axially together. In the embodiment shown in FIGS. 22A-C, the distal portion 1464 of the retainer 1408 includes an annular skirt 1468 having six tabs 1470 that are configured to engage six corresponding slots 1472 between the two concentric annular lips 1474, 1476 of the actuator seal 1406, as shown in FIG. 23B. Adhesive, snap fit, pressure fit, etc. may be used to help secure the tabs 1470 in slots 1472. In other embodiments, the retainer 1408 may not include tabs 1470 and instead, the seal 1406 may be attached to the retainer 1408 using known connection mechanisms in the art. The annular skirt 1468 of the retainer 1408 may comprise any number of tabs 1470, for example, two, three or four. In one embodiment, the annular skirt 1468 comprises a single annular ring.

Figure 20A:
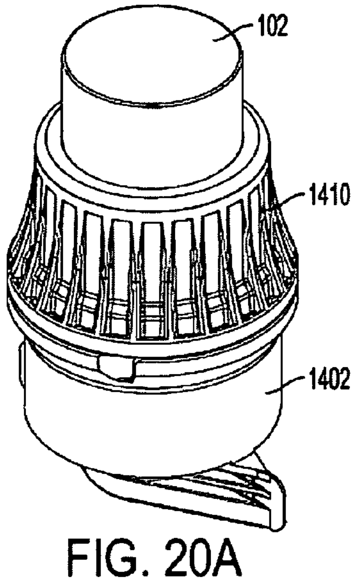
FIG. 20A is an isometric view of another exemplary first container and port assembly.
Figure 20B:
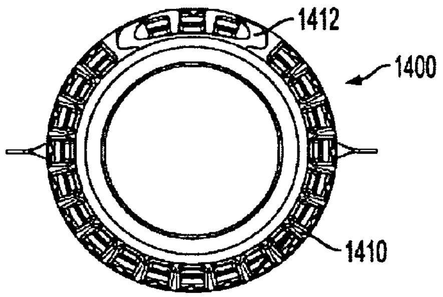
FIG. 20B is a top view of the first container and port assembly shown in FIG. 20A.
Figure 20C:
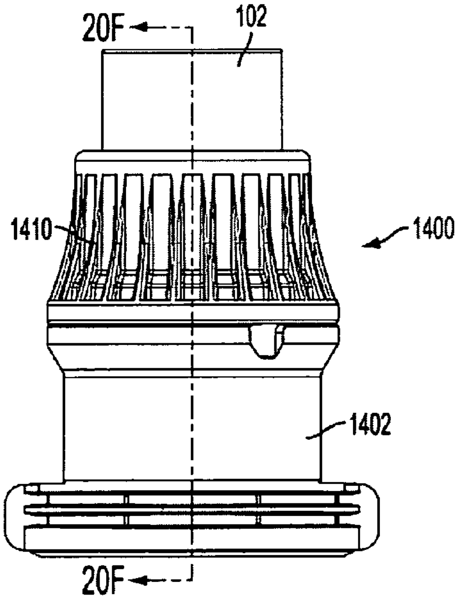
FIG. 20C is a side view of the first container and port assembly shown in FIG. 20A.
Figure 20E:
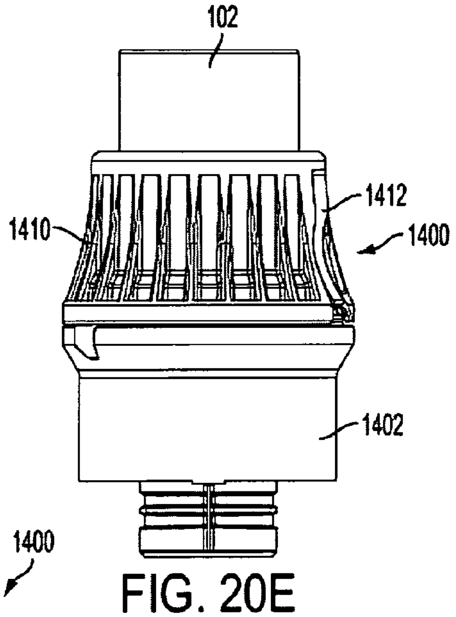
FIG. 20E is another side view of the first container and port assembly shown in FIG. 20A.
Figure 20D:
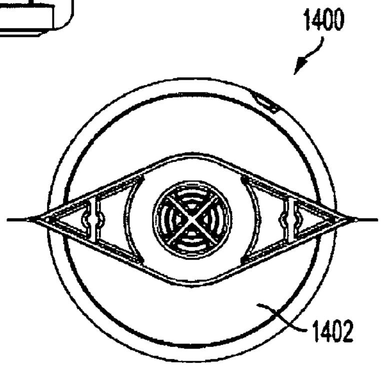
FIG. 20D is a bottom view of the first container and port assembly shown in FIG. 20A.
Figure 20F:
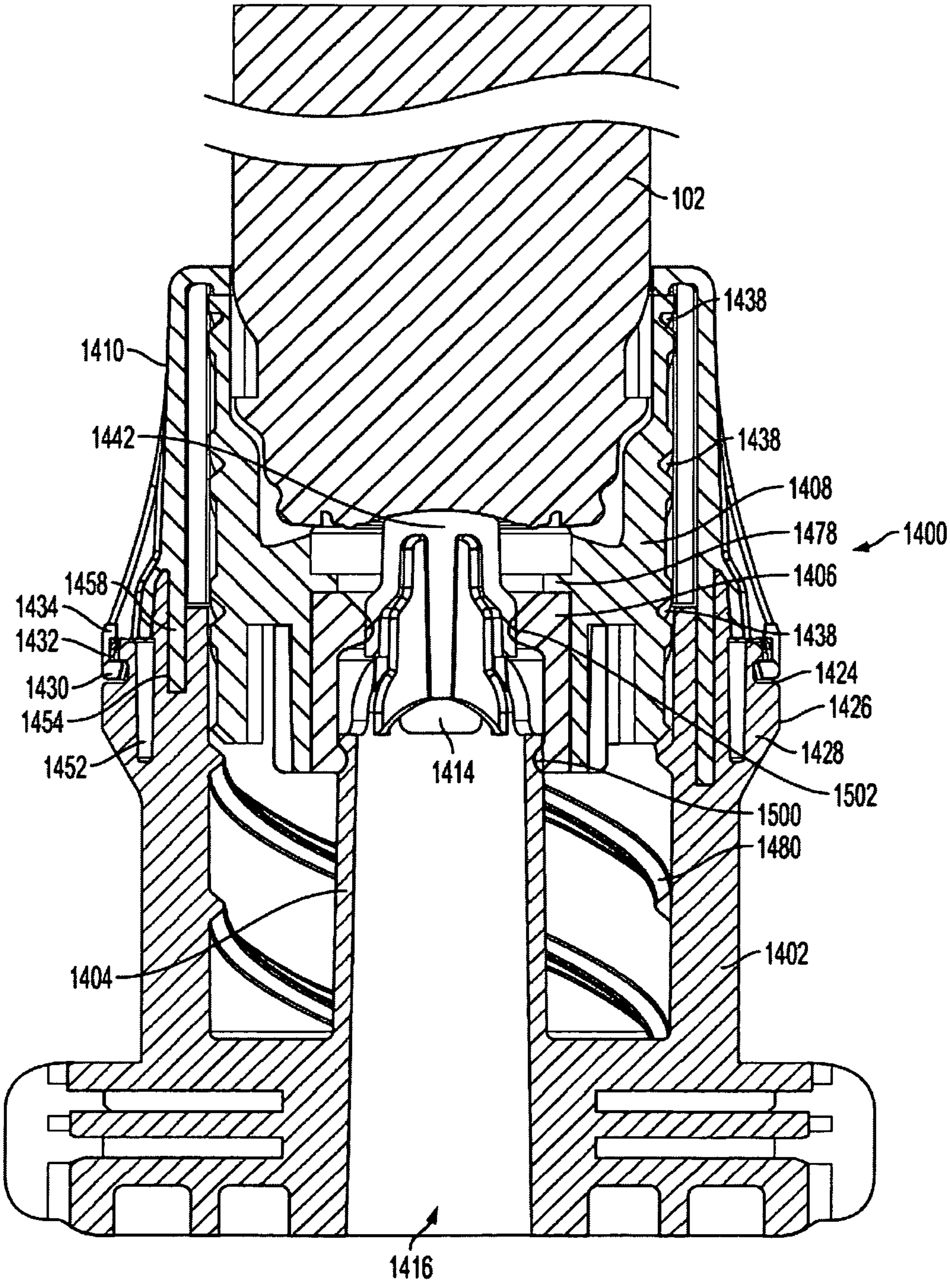
FIG. 20F is a cross-sectional view of the first container and port assembly shown in FIG. 20A.

As shown best in FIGS. 20F and 22A, the retainer 1408 also includes a flange 1478 that extends inward from the inner surface of the bore 1466, against which the proximal end of the inner annular skirt 1476 of the actuator seal 1406 abuts.

The outer surface 1440 of the retainer 1408 includes external threads 1438 that, as noted above, are complimentary to the internal threads 1480 of the port housing 1402. The threads 1438, 1480 allow the retainer 1408 to be threaded into the port housing 1402 during activation of the system. As shown, the outer wall of the retainer 1408 comprises four portions 1484 that are equally spaced around the axis of the retainer 1408. In other embodiments, the outer wall may comprise any number of portions 1484 or may be continuous cylindrical shell.

The retainer 1408 also includes four radial notches 1486 at its proximal end that are equally spaced around the axis of the retainer 1408 and are configured to engage corresponding splines 1488 on the internal surface 1490 of the activation collar 1410. Engagement between the splines 1488 and notches 1486 allows the retainer 1408 to rotate with the activation collar 1410 while moving distally along the splines 1488 relative to the activation collar 1408 as the retainer 1408 is threaded into the port housing 1402 during activation of the system. As the activation collar 1408 is rotated relative to the port housing 1402, the engagement between the splines 1488 of the collar 1408 and the notches 1486 of the retainer 1408 causes the retainer 1408 to rotate. In turn, this rotation causes the retainer 1408 to be threaded into the port housing 1402. As the retainer 1408 is threaded into the port housing 1402, the axially fixed actuator 1404 forces the stopper 122 of the first container 102 into the cavity of the first container 102. In other embodiments, the same functional relationship between the retainer 1408 and activation collar 1410 may be accomplished by providing the outer surface of the retainer 1408 with spline-like features and the inner surface 1490 of the activation collar 1410 with notches/grooves.

In one embodiment, the retainer 1408 may be provided with a proximally facing annular seal on the proximal surface of the flange 1478 of the retainer 1408. In such an embodiment, the annular seal abuts and seals against the distal surface of the first container 102 (e.g., the distally facing surface of the annular flange 119) when the first container 102 is docked to the port assembly 1400. This sealing engagement helps to prevent any diluent and/or medicament from escaping out of the fluid flow path established between the first and second containers 102, 104 during use. In addition to or instead of a proximally facing annular seal, the retainer 1408 may be provided with an annular seal that projects radially inward and seals against a lateral surface of the first container 102 when the first container 102 is docked to the port assembly 1400. Such a radial seal may help ensure sealing engagement between the first container 102 and the port assembly 1400 regardless of any axial movement of the first container 102 after docking.

As shown in FIGS. 23A-D, the actuator seal 1406 generally comprises two concentric annular lips 1474, 1476 that extend proximally from the base 1492 of the seal 1406. As shown, the inner annular lip 1476 defines an axial bore 1494 and is longer than the outer annular lip 1474, however, in other embodiments, the annular lips 1474, 1476 may be the same length or the outer annular lip 1474 may be longer than the inner annular lip 1476. The annular gap 1496 between the lips 1474, 1476 is configured to receive at least a portion of the skirt 1468 of the retainer 1408 such that the actuator seal 1406 can be secured to the main body 1408. At the bottom of the annular gap 1496 there are six slots 1472 that correspond to the six tabs 1470 of the skirt 1468 of the main body 1408. These slots 1472 are configured to receive the tabs 1470 of the skirt 1468. As noted above, adhesive, snap fit, pressure fit, etc. may be used to help secure the tabs 1470 in slots 1472. When the actuator seal 1406 is secured to the retainer 1408, the proximal surface 1498 of the inner annular lip 1476 abuts or is in close proximity to the distal surface of the inner bore flange 1478 of the retainer 1408, as shown in FIG. 20F.

The actuator seal 1406 also includes two sealing beads 1500, 1502 that extend from the inner surface 1504 of the inner annular lip 1476 into the bore 1494. The sealing beads 1500, 1502 are configured to seal against the actuator 1404 such that when the system is in the non-activated position, the proximal flange 1502 seals above the openings 1414 in the actuator 1404 while the distal flange 1500 seals below the openings 1414 in the actuator 1404, as shown in FIG. 20F. After activating the system, the retainer 1408 and actuator seal 1406 slide together distally about the actuator 1404 until both sealing beads 1500, 1502 are located below the openings 1414 in the actuator 1404. Accordingly, the openings 1414 in the actuator 1404 are able to communicate with the contents of the first container 102. As shown, the proximal bead 1502 extends further into the bore 1494 of the actuator seal 1406 than the distal bead 1500. This ensures that the proximal bead 1502 can seal against the reduced diameter of the proximal portion of the actuator 1404 prior to activation. In other embodiments, both sealing beads 1500, 1502 may be the same size. The beads 1500, 1502 each provide a fluid seal with the actuator 1404 that prevents the escape of fluid prior to and during activation.

Turning to FIGS. 24A-F, the activation collar 1410 is generally cylindrical with a flare at its distal end. The outer surface of the activation collar 1410 is provided with ribs/ridges 1506 so that a user can easily grip and rotate the activation collar 1410 in order to activate the system. In other embodiments, the outer surface of the activation collar 1410 may be smooth, provided with depressions/dimples or bumps instead of ribs 1506, or may simply be provided with a surface finish that enhances the friction between the activation collar 1410 and user's hands. The diameter of the bore 1508 that extends through the activation collar 1410 is larger than the outside diameter of the first container 102 so that the first container 102 can be inserted through the proximal opening of the bore 1508 and docked to the retainer 1408 of the port assembly 1400.

As shown, the activation collar 1410 includes four pairs of splines 1488. Each pair of splines 1488 is spaced to correspond to the width of the notches 1486 in the retainer 1408. In another embodiment, each pair of splines 1488 may be replaced with a single spline having a width that corresponds to each respective notch 1486. Any number of splines 1488 and corresponding notches 1486 is possible as long as rotation of the activation collar 1410 can be translated into rotation of the retainer 1408 and so that the retainer 1408 can slide axially along the splines 1488.

As noted above, the distal end of the activation collar 1410 is configured to rotatably attach to the port housing 1402. As shown best in FIGS. 20F and 24F, the distal end of the activation collar 1410 includes two concentric annular skirts 1434, 1458. The inner annular skirt 1458 and guide tab 1459 is configured to fit within the inner annular channel 1454 of the port housing 1402 to stabilize the activation collar 1410 and ensure that it easily rotates relative to the port housing 1402. The outer annular skirt 1434 includes a plurality of annularly spaced protrusions 1430 on its inner surface 1432 that are configured to engage the annular recess/groove 1424 in the outer surface 1426 of the outer annular lip 1428 of the port housing 1402, which allows rotation but prevents axial disengagement between the activation collar 1410 and the port housing 1402.

Figure 24A:
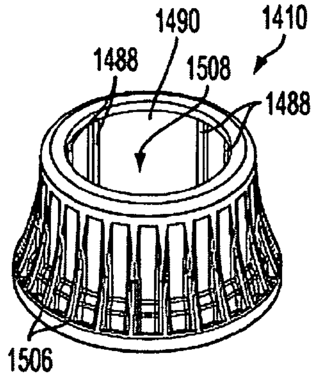
FIG. 24A is an isometric view of an exemplary activation collar of the port assembly shown in FIGS. 20A-F.
Figure 24B:
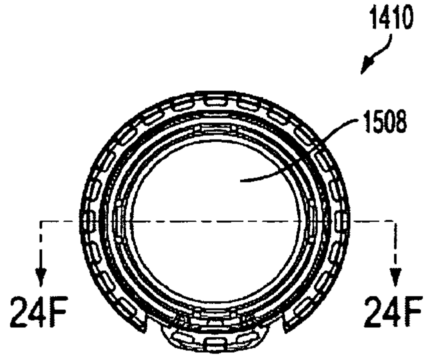
FIG. 24B is a bottom view of the activation collar shown in FIG. 24A.
Figure 24C:
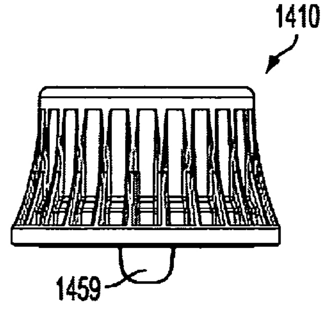
FIG. 24C is a side view of the activation collar shown in FIG. 24A.
Figure 24D:
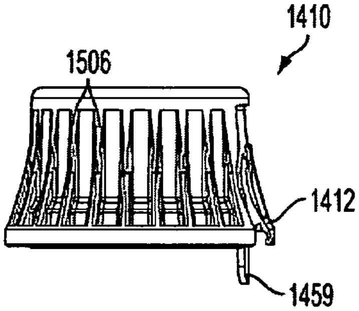
FIG. 24D is another side view of the activation collar shown in FIG. 24A.
Figure 24E:
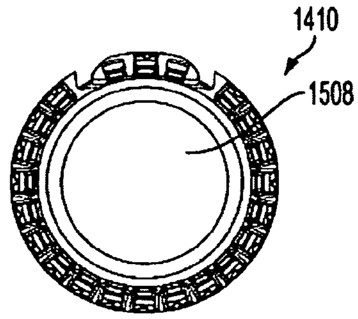
FIG. 24E is a top view of the activation collar shown in FIG. 24A.
Figure 24F:
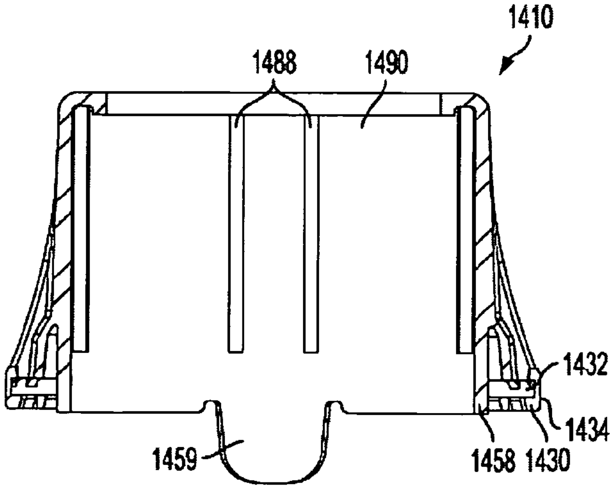
FIG. 24F is a cross-sectional view of the activation collar shown in FIG. 24A.

Also, as partially shown in FIGS. 20E and 24D, the port assembly 1400 includes a hanger 1412 for conveniently hanging the system on an appropriate device (e.g., pole, rack or stand). When the port assembly 1400 is in a non-activated non-hanging condition, the hanger 1412 is not accessible to the user. Upon activation of the system, the hanger 1412 transitions from the non-activated non-hanging condition to an activated hanging condition which releases the hanger 1412, presents it for proper use, and is operable by the user. In one embodiment, the release of the hanger 1412 and the establishment of fluid communication occur simultaneously.

Turning to FIGS. 21A-E, prior to activation, a distal portion of the hanger 1412 is positioned in the circumferential guide slot 1452 of the port housing 1402; however, as the activation collar 1410 is rotated in order to activate the system, the hanger 1412 slides within the guide slot 1452 until the distal portion contacts the angled surface 1510 which forces the hanger 1412 out of the guide slot 1452 via the exit slot 1456. The amount of rotation needed to transition the hanger 1412 from the non-activated non-hanging position to the activated hanging position and to activate the system may vary, and in particular may be between about 120-200 degrees.

Figure 8B:
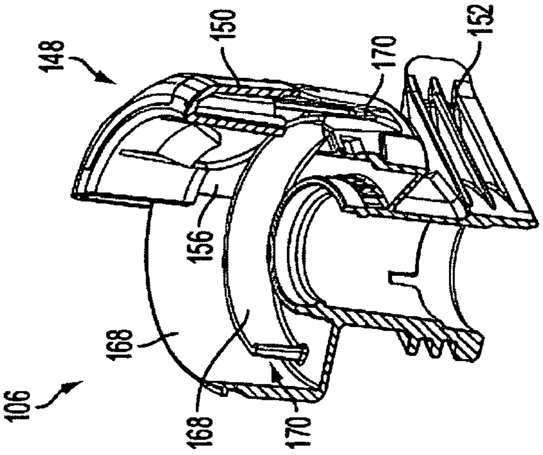
FIG. 8B is a partial cross-sectional isometric view of the portion of the port assembly of FIG. 8A during activation.
Figure 8A:
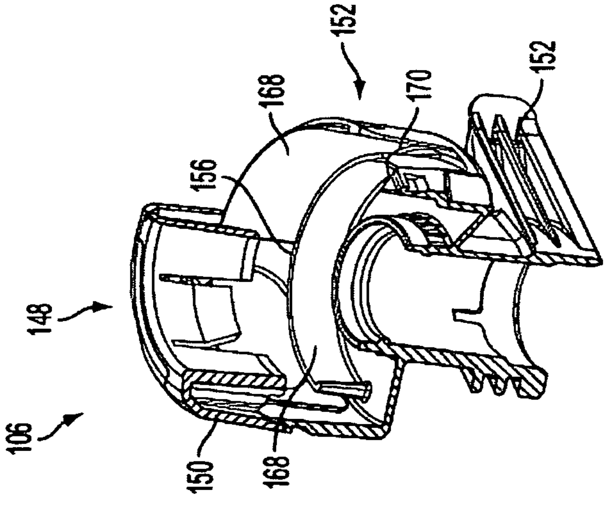
FIG. 8A is a partial cross-sectional isometric view of a portion of an exemplary port assembly of the system shown in FIG. 1, including the hanger, before activation.
Figure 9A:
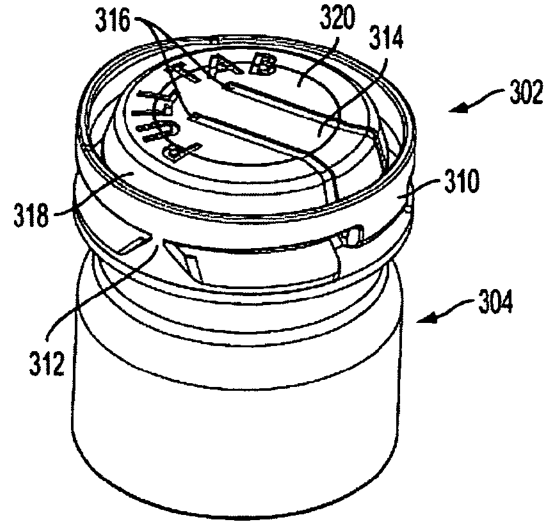
FIG. 9A is an isometric view of another exemplary body cap and top cap that may be used with the first container shown in FIGS. 2A-F.
Figure 9B:
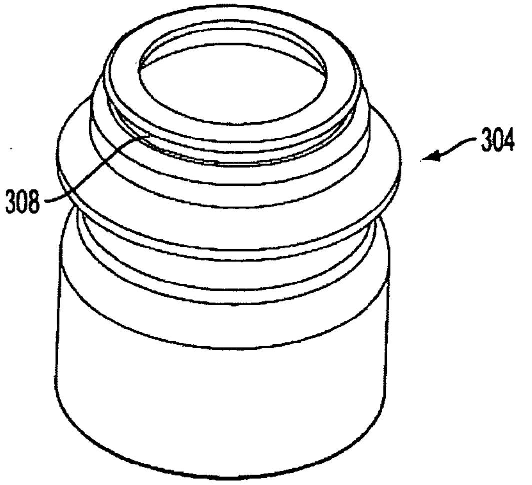
FIG. 9B is an isometric view of the body cap shown in FIG. 9A.
Figure 9C:
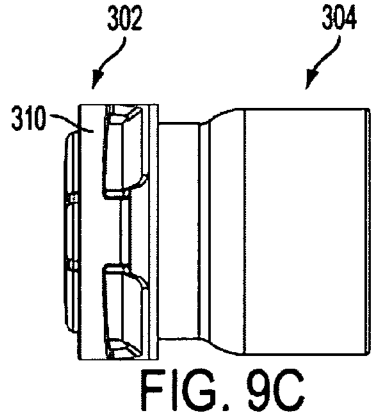
FIG. 9C is a side view of the body cap and top cap shown in FIG. 9A.
Figure 9D:
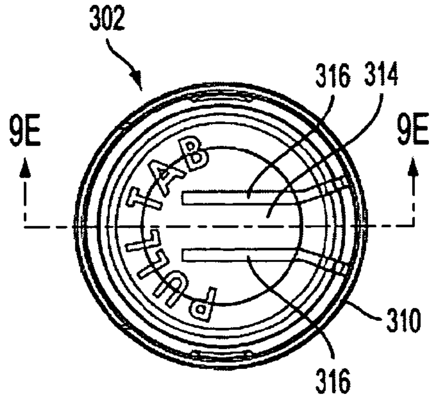
FIG. 9D is a top view of the body cap and top cap shown in FIG. 9A.
Figure 9E:
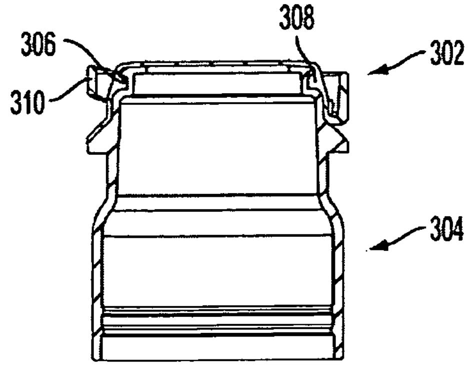
FIG. 9E is a cross-sectional view of the body cap and top cap shown in FIG. 9A.

As explained with respect to FIGS. 8A-C above, the hanger 1412 may be hinged (e.g., by a living hinge, a pin hinge, or any other hinge known in the art) to the activation collar 1410. The hinge mechanism connecting the hanger 1412 to the activation collar 1410 may include a spring or be composed of a resilient material that biases the hanger 1412 away from the retainer 1408 when the hanger 1412 is released from the port housing 1402 upon activation of the system. Accordingly, when the activation collar 1410 is sufficiently rotated, the biasing force causes the hanger 1412 to pivot away from the collar 1410 so that the system can be easily hung for use. In embodiments where the hinge does not include a spring, once the activation collar 1410 is sufficiently rotated, the hanger 1412 is made available for a user to manually manipulate for hanging.

In other embodiments, the hanger is connected to the first or second containers, and the hanger is operable only upon the establishment of fluid communication between the first and second containers.

The port assembly 1400 shown in FIGS. 20A-24F may be provided with a locking mechanism that prevents inadvertent rotation of the activation collar 1410 relative to the port housing 1402. Such locking mechanisms are shown and described with reference to FIGS. 12A-14C and FIGS. 40A-B below.

FIGS. 25A-40B illustrate another exemplary two-component system 1600 that allows a user (e.g., a pharmacist or other healthcare worker) to mix the contents of two separate containers (e.g., a medicament and a diluent) and then deliver the mixture (e.g., a medicinal fluid) to a patient while maintaining sterility of the contents and mixture and preventing unwanted release of the contents and mixture into the environment. The system 1600 includes (1) a first container 1602 containing a first substance and (2) a second container 1604 containing a second substance, the second container 1604 having a port assembly 1606 at its proximal end for receiving and connecting to the first container 1602. Although described and shown herein as being mounted to the second container 1604, in another embodiment, the port assembly 1606 may be provided as a separate and stand-alone device that connects the first and second containers 1602, 1604.

In the embodiment shown in FIG. 25A, the first container 1602 is a medicament container in the form of a vial 1616 that is sealed by a stopper 1617. As shown, the 1616 vial is partially encased with a body cap 1608 that is configured to engage the port assembly 1606 of the second container 1604. The second container 1604 is a diluent container in the form of a blow-fill-seal container 1618 with (1) the port assembly 1606 at its proximal end for receiving and engaging the first container 1602 and (2) an administration port 1610 at its distal end for delivering a medicinal fluid to the patient. The first container 1602, port assembly 1606, and administration port 1610 may each be provided with a protective cap to help maintain sterility of the system 1600 prior to use. As shown in FIG. 25A, the port assembly 1606 and administration port 1610 are provided with protective caps 1612 and 1614 respectively. The first container 1602 may be provided with a protective cap according to any of the embodiments described herein (e.g., protective cap 114 (see FIG. 2A)) or as generally known to those of skill in the art.

As illustrated in the exploded view of the system 1600 shown in FIG. 25B, the port assembly 1606 generally includes: (1) a two-part port housing 1620 with an axially fixed actuator 1622 configured to open the first container 1602, (2) a main body including (a) a two-part retainer 1624 for docking the first container 1602 to the port assembly 1606 and (b) an activation collar 1626 for activating the system 1600 upon rotation, (3) an axially moveable plug member 1628 having a seal 1632 for fluidly sealing the fluid passageway between the port housing 1620 and the second container 1604 prior to activating the system 1600, and (4) a hanger 1630 for hanging the system 1600 after activation so that a medicinal fluid can be delivered to a patient.

As shown, the two-part port housing 1620 includes an inner port housing part 1620*a* and an outer port housing part 1620*b*. Likewise, the two-part retainer 1624 includes an inner retainer part 1624*a* and an outer retainer part 1624*b*. Although shown as two-part components, in another embodiment, the port housing 1620 and retainer 1624 may be designed and manufactured as single unitary components. One skilled in the art would understand that if manufacturing permits, any component described herein could be designed as a single or multi-part component. For simplicity, the two-part port housing 1620 and two-part retainer 1624 are principally described herein as single unitary components with reference to FIGS. 31A-E and 34A-D.

Figure 26:
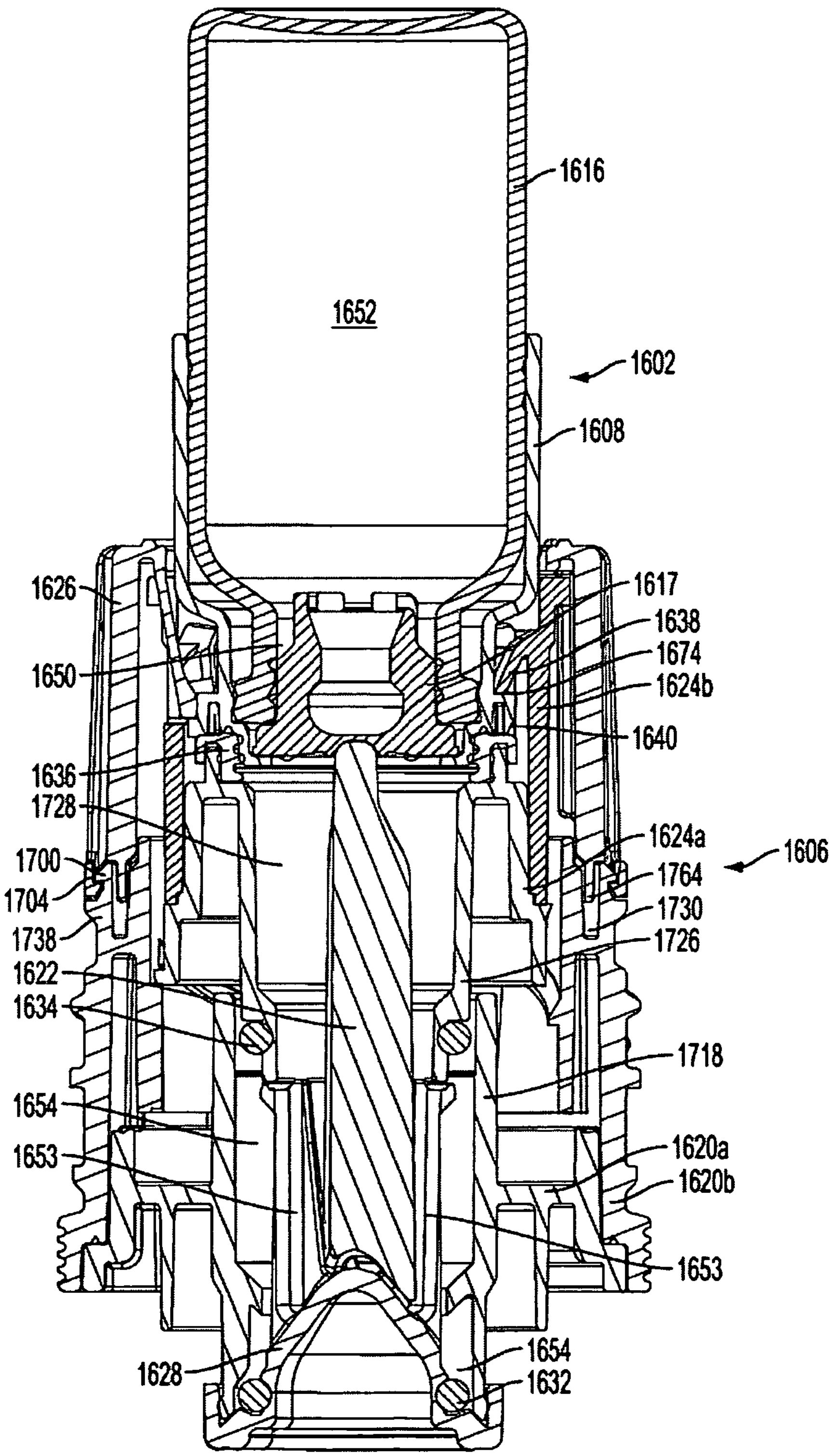
FIG. 26 illustrates the system shown in FIG. 25A in the docked position prior to activation.
Figure 27:
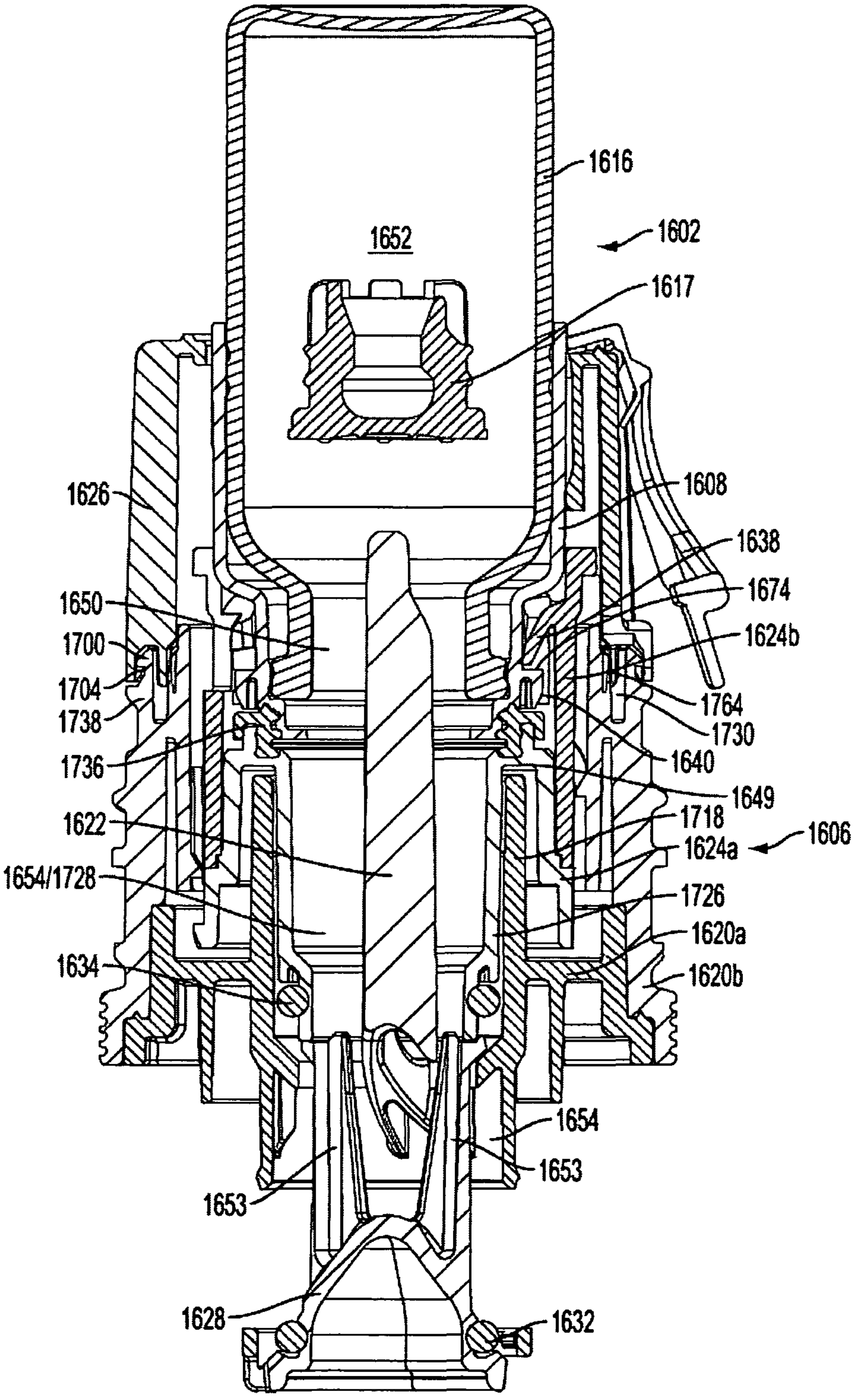
FIG. 27 illustrates the system shown in FIG. 25A in the activated position.
Figure 28A:
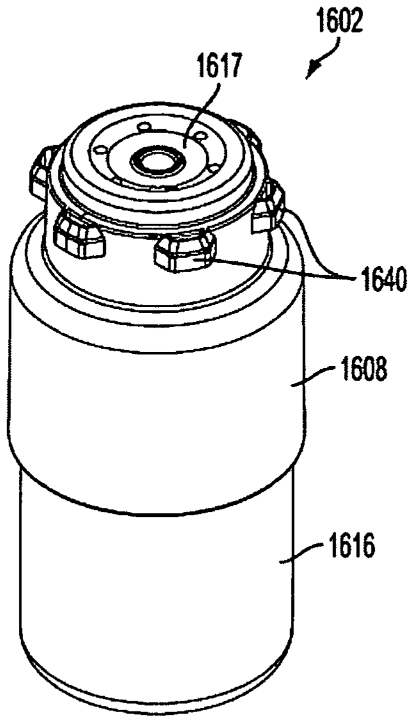
FIG. 28A is an isometric view of an exemplary first container of the system shown in FIG. 25A.
Figure 28B:
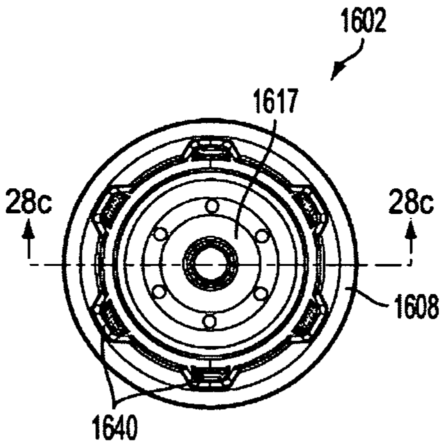
FIG. 28B is a top view of the first container shown in FIG. 28A.
Figure 28C:
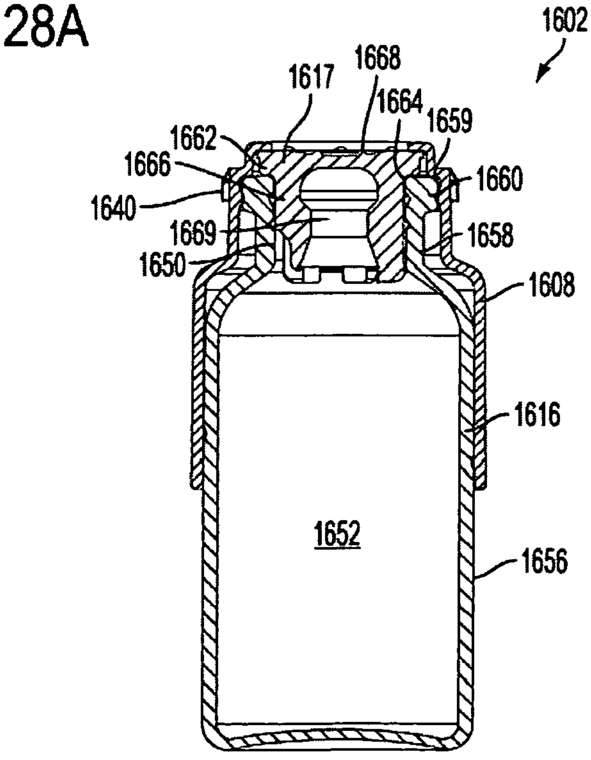
FIG. 28C is a cross-sectional view of the first container shown in FIG. 28A.
Figure 29A:
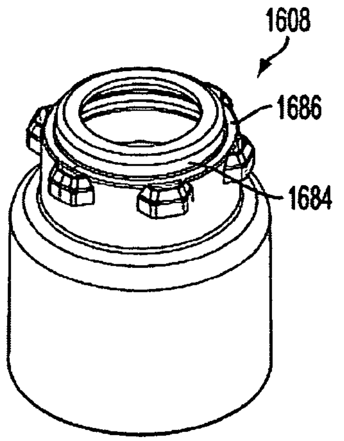
FIG. 29A is an isometric view of an exemplary body cap of the first container shown in FIG. 28A.
Figure 29B:
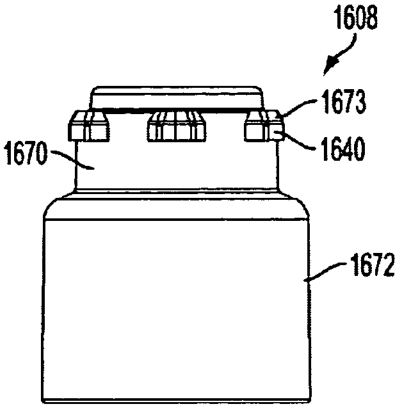
FIG. 29B is a side view of the body cap shown in FIG. 29A.
Figure 29C:
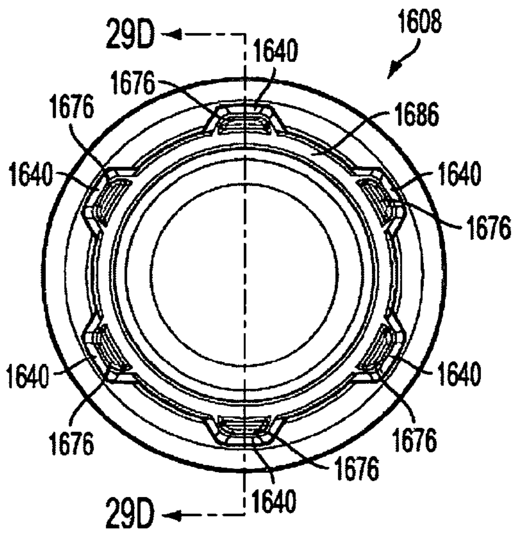
FIG. 29C is a top view of the body cap shown in FIG. 29A.
Figure 29D:
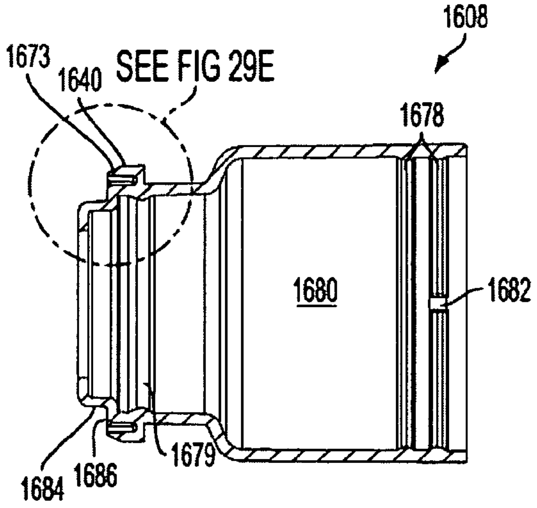
FIG. 29D is a cross-sectional view of the body cap shown in FIG. 29A.
Figure 29E:
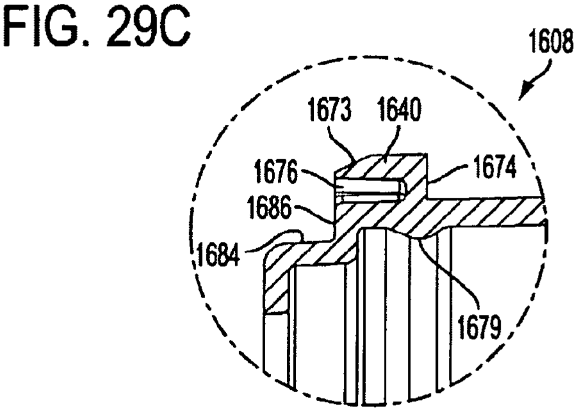
FIG. 29E is a zoomed-in cross-sectional view of Section A-A of FIG. 29D.
Figure 30A:
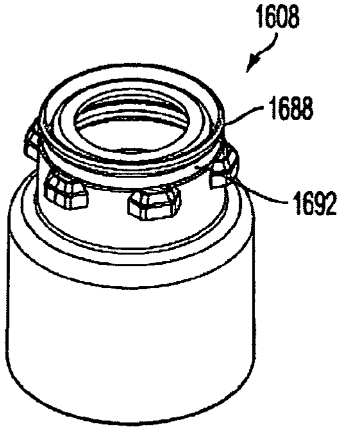
FIG. 30A is an isometric view of another exemplary body cap that may be used with the first container shown in FIG. 28A.
Figure 30B:
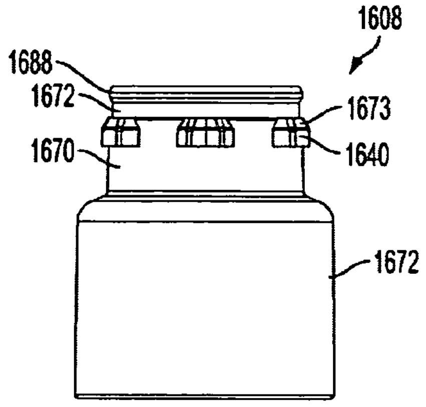
FIG. 30B is a side view of the body cap shown in FIG. 30A.
Figure 30C:
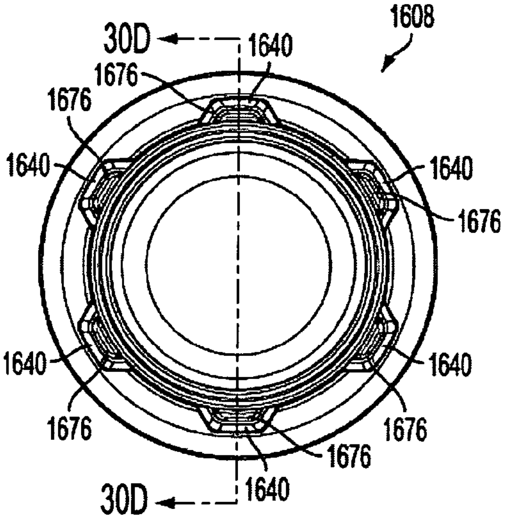
FIG. 30C is a top view of the body cap shown in FIG. 30A.
Figure 30D:
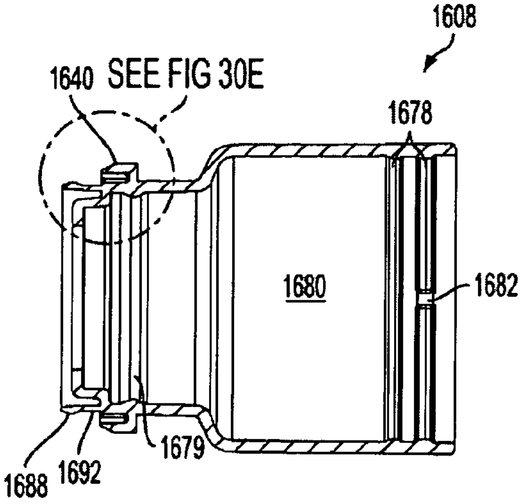
FIG. 30D is a cross-sectional view of the body cap shown in FIG. 30A.
Figure 30E:
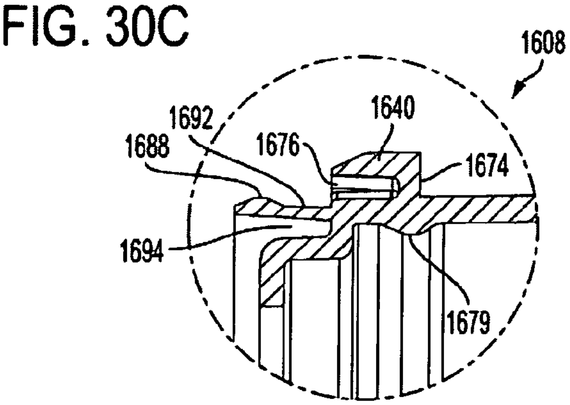
FIG. 30E is a zoomed-in cross-sectional view of Section A-A of FIG. 30D.

The port assembly 1606 also includes three fluid-tight seals 1632, 1634, 1636 to prevent fluid leakage. As shown in FIGS. 26-27, seal 1632 of the plug member 1628 is provided between the body of the plug member 1628 and the port housing 1620. Seal 1634 is provided between the port housing 1620 and the retainer 1624. This seal 1634 is configured to seal a portion of the fluid passageway defined by the bore 1654 of the port housing 1620 to a portion of the fluid passageway defined by the bore 1728 of the retainer 1624. Seal 1636 is provided within the retainer 1624 and is configured to sealingly engage the first container 1602 when the first container 1602 is docked to the port assembly 1606 and during activation of the system 1600.

To use the system 1600 a user performs two simple steps. First, the user docks the first container 1602 to the port assembly 1606 (FIG. 26 shows the system in the docked position). Second, the user activates the system 1600 (FIG. 27 shows the system in the activated position). Activation of the system 1600 results in fluid communication between the first and the second containers 1602, 1604.

A user docks the first container 1602 to the port assembly 1606 by inserting the first container 1602 into the proximal end of port assembly 1606 until retention tabs 1638 of the retainer 1624 engage protrusions 1640 of the body cap 1608. At this point, the first container 1602 is irreversibly connected to the port assembly 1606, and both the first and second containers 1602, 1604 remain sealed by stopper 1617 and plug/seal 1628/1632 respectively.

A user activates the system 1600 by rotating the activation collar 1626 relative to the port housing 1620. Rotation of the activation collar 1626 causes the retainer 1624, which is engaged to (1) the port housing 1620 via threads 1642, 1644 (see, e.g., FIGS. 31A and 34A) and (2) the activation collar 1626 via an axial spline-groove arrangement 1646, 1648 (see, e.g., FIGS. 31A and 34A), to rotate and move axially in the distal direction relative to the port housing 1620. This rotational and axial movement is a result of the retainer 1624 being threaded into the port housing 1620 as the user rotates the activation collar 1626. Because the first container 1602 is secured to the retainer 1624 via engagement between the protrusions 1640 and tabs 1638, the first container 1602 moves in the distal direction with the retainer 1624 during this process. As the retainer 1624 and first container 1602 move in the distal direction relative to the port housing 1620, the actuator 1622, which is axially fixed in the port housing 1620, forces the stopper 1617 out of the opening 1650 of the first container and into the cavity 1652 of the first container, thereby opening the first container 1602. Concurrently, the distal end of the retainer 1624 pushes on the proximal end of the legs 1653 of the plug 1628, which forces the plug 1628/seal 1632 out of the bore 1654 of the port housing 1620 and into an open position partially within the second container 1604, thereby opening the fluid passageway to the second container 1604. Accordingly, the plug member 1628/seal 1632 moves axially relative to the port housing 1620 and actuator 1622 to open the fluid passageway. As a result, fluid communication is established between the first and second containers 1602, 1604 via the fluid passageway defined by the bore 1654 of the port housing 1620 and the bore 1728 of the retainer 1624.

The individual components of the system 1600 will now be described in detail. Like the first container 102 shown in FIGS. 2A-F, the first container 1602 of this embodiment includes a container body having an opening 1650 fluidly connected to a cavity defined by the container body. In one embodiment shown best in FIG. 28C, the first container 1602 includes a vial 1616 partially encased by a body cap 1608. The vial 1616 generally includes a body portion 1656 and a neck portion 1658 having an annular flange (or shoulder) 1660 at its distal end that defines an opening 1650 in which a stopper 1617 is located. In its sealed position, the stopper 1617 engages both the opening 1650 and the distal surface 1659 of the vial shoulder 1660.

The stopper 1617 has a body portion 1666 that is configured to engage the opening 1650 of the vial 1616 and an annular flange 1662 radially extending from the body portion 1666 that is configured to engage the distal surface 1659 of the vial shoulder 1660. In the embodiment shown, the distal surface of the stopper 1617 has a depression 1668, which assists in reducing the force required to transition the stopper 1617 from a first sealed position in the opening 1650 of the vial 1616 to a second unsealed position in the cavity 1652 of the vial 1616 (the stopper "push-in-force") when the system is activated. The depression 1668 may also serve as a target when inserting a syringe needle or cannula into the vial 1616 in order to make additions to and/or extract contents from the vial 1616. While a depression 1668 may be useful in some embodiments, other embodiments may utilize a stopper 1617 without such a feature. To further reduce the stopper push-in-force, the stopper 1617 is also provided with a cavity 1669. The cavity 1669 enables the flange 1662 to fold more easily when the stopper 1617 is being pushed into the cavity 1652 of the vial 1616. In addition, an undercut (not shown) may be provided about the circumference of the stopper 1617 to further assist in reducing the stopper push-in force by enabling the flange 1662 to fold more easily when the stopper 1617 is being pushed into the cavity 1652 of the vial 1616, as described in U.S. Pat. No. 8,075,545, which is incorporated by reference herein in its entirety.

The opening 1650 of the vial 1616 may have a constant diameter throughout the neck and shoulder portions 1658, 1660 or may have a larger diameter at its distal end to facilitate the transition of the stopper 1617 from the first sealed position in the vial opening 1650 to the second unsealed position within the vial cavity 1652. In an embodiment where the diameter of the opening 1650 is greater near its distal end, the stopper push-in-force may be further reduced as such a configuration also allows the flange 1662 of the stopper 1617 to fold more easily. A larger opening 1650 can be accomplished by enlarging the radius at the edge 1664 of the opening 1650.

The stopper push-in force should be achievable by the average user. In embodiments where the stopper 1617 is designed to be dual-use (i.e., capable of being used with the system 1600 described herein or being used separately with a syringe needle or cannula), the stopper 1617 should be configured such that a syringe needle or cannula can be inserted through the stopper 1617 without dislodging the stopper 1617 from its sealed position in the opening 1650 of the first container 1602. At the same time, the stopper 1617 should maintain the appropriate push-in force so that it can be used with the system 1600 by an average user. Accordingly, in one embodiment, the stopper push-in force is in the range of about 4-20 pounds of force. In another embodiment, the stopper push-in force is in the range of about 5-15 pounds of force. In a further embodiment, the stopper push-in force is in the range of about 8-13 pounds of force.

The body cap 1608 of the first container 1602 is generally positioned around the neck 1658 and upper region of the body portion 1656 of the vial 1616. The body cap 1608 has at least one axial locking member that is configured to engage at least one complimentary mating member of the port assembly 1606 to dock the first container 1602 to the port assembly 1606. In the embodiment shown best in FIGS. 29A-E, the axial locking member of the body cap 1608 includes a plurality of protrusions 1640 that are configured to engage a plurality of retention tabs 1638 of the retainer 1624 to irreversibly connect the first container 1602 to the retainer 1624 such that the first container 1602 cannot be pulled out of the port assembly 1606. As shown, the protrusions 1640 are located near the distal end of the body cap 1608. In other embodiments, however, the protrusions 1640 may be located closer or further away from the distal end of the body cap 1608. Moreover, the protrusions 1640 may be located around the neck portion 1670 of the body cap 1608 (as shown in FIGS. 29A-E) or around the body portion 1672 of the body cap 1608.

The tapered geometry 1673 of the distal portion of each of the protrusions 1640 helps to center the first container 1602 in the port assembly 1606 during the docking step while the underside 1674 of each of the protrusions 1640 provides a surface for the retention tabs 1638 of the retainer 1624 to engage in order to securely dock the first container 1602 to the port assembly 1606. As shown best in FIG. 29E, each protrusion 1640 includes a cavity 1676, which reduces the likelihood of sinks being created during molding by decreasing the thickness of the material.

In the depicted embodiment, there are six protrusions 1640; however, the number of protrusions 1640 may vary depending on design. For example, the body cap 1608 may include a single annular docking protrusion in the form of a flange that extends radially outward from the neck 1670 or body portion 1672 of the body cap 1608.

In certain embodiments of the port assembly 1606, one or more of the protrusions 1640 are not used to dock the first container 1602 to the port assembly 1606 but are instead unlocking members used to unlock the port assembly 1606 for activation. For example, in one embodiment, three of the six protrusions ("docking protrusions") 1640 are used to dock the first container 1602 to the port assembly 1606 while the other three protrusions ("unlocking protrusions") 1640 are unlocking members used to unlock a locking mechanism of the port assembly 1606 so that a user can rotate the activation collar 1626 relative to the port housing 1620. In other words, prior to unlocking the locking mechanism of the port assembly 1606, the activation collar 1626 cannot rotate relative to the port housing 1620. In such an embodiment, the retainer 1624 may have three retention tabs 1638 that extend radially inward for engaging the three docking protrusions 1640 of the body cap 1608, as shown in FIGS. 34A-D. However, whether used for docking or used for unlocking, the protrusions 1640 may be identical, which eliminates the need for a user to match the protrusions with corresponding features of the retainer 1624. Moreover, the number of docking and unlocking protrusions may vary.

The body cap 1608 is configured to sealingly engage both the vial 1616 and the port assembly 1606 of the second container 1604 such that fluid and/or contaminants are prevented from entering and/or escaping out of the fluid flow path established between the first and second containers 1602, 1604 during use (e.g., during activation, during mixing, or during fluid delivery to a patient). To seal against the vial 1616, the body cap 1608 has two rib seals 1678 near its proximal end and another rib seal 1679 near its distal end. The rib seals 1678, 1679 extend radially inward from the interior surface of the body cap 1608. The proximal rib seals 1678 are positioned to seal against the body portion 1656 of the vial 1616 while the distal rib seal 1679 is positioned to seal against the flange 1660 of the vial 1616.

In one embodiment, each of the proximal rib seals 1678 is interrupted twice at approximately 180 degrees to allow for venting of the body cap cavity 1680. In such an embodiment, the interruptions (only one interruption 1682 is shown) of one of the rib seals 1678 may be offset 90 degrees from the interruptions of the other rib seal 1678 to provide a tortuous path for fluids and/or contaminants, thereby helping to preserve sterility of the system. Of course a different number of interruptions and other degrees of offset between the proximal rib seals 1678 are possible.

To sealingly engage the port assembly 1606, the body cap 1608 is provided with a radially-facing sealing surface 1684 near its distal end. The radially-facing sealing surface 1684 is configured to form a seal with seal 1636 in the cavity of the retainer 1624 when the first container 1602 is docked to the port assembly 1606, thereby radially sealing the first container 1602 to the port assembly 1606 prior to opening the first or second container. In other words, the seal is established before activation of the system (i.e., before the actuator 1622 forces the stopper 1617 into the cavity 1652 of the first container 1602, thereby opening the first container 1602, and before the plug 1628 is moved distally out of the bore 1654 of the port housing 1620, thereby opening the second container 1604). This ensures that once the first and second containers 1602, 1604 are opened during activation, fluid cannot escape the fluid-flow path between the two containers. As shown best in FIG. 29E, the body cap 1608 of this embodiment also includes an axially-facing sealing surface 1686 that is also configured to engage seal 1636 of the retainer 1624 upon docking the first container 1602 to the port assembly 1606. Accordingly, upon docking the first container 1602 to the port assembly 1606, two seals may be established between the first container 1602 and the port assembly 1606: a radial seal and an axial seal. In other embodiments, the body cap 1608 may include either a radially-facing sealing surface or an axially-facing sealing surface, but not both.

In another embodiment of the body cap 1608 shown in FIGS. 30A-E, the body cap 1608 is provided with a radial sealing bead 1688 near its distal end. Like the radial sealing surface 1684 described above, the radial sealing bead 1688 of the body cap 1608 is configured to form a radial seal with the retainer 1624 of the port assembly 1606 when the first container 1602 is docked to the port assembly 1606, prior to activation. In this embodiment, a seal such as seal 1636 does not need to be provided in the cavity of the retainer 1624. Instead, the sealing bead 1688 is configured to seal against a radially-facing sealing surface 1690 of the retainer 1624.

The sealing bead 1688 is positioned near the end of a distally extending annular flexible lip 1692 of the body cap 1608 that is adjacent an annular channel 1694. The channel 1694 allows the lip 1692 to deflect radially inward as it contacts the radially-facing sealing surface 1690 of the retainer 1624 when the first container 1602 is inserted into the retainer 1624 of the port assembly 1606 during docking. As the lip 1692 deflects radially inward, the resilient nature of the lip 1692 biases the lip 1692 radially outward to ensure that a seal is established between the sealing bead 1688 and sealing surface 1690.

Turning now to the port housing 1620 shown in FIGS. 31A-E, the port housing 1620 has a first end (proximal end) and a second end (distal end). A distal portion 1696 of the outer surface of the port housing 1620 serves as a mounting surface for the second container 1604. In another embodiment, the mounting surface 1696 may comprise substantially the entire outer surface of the port housing 1620. To assist in mounting the second container 1604 to the port housing 1620, the outer surface includes ribs 1698 that increase the mountable surface area. In order to prevent the contents of the second container 1604 from leaking, a fluid tight seal should be established between the second container 1604 and port assembly 1606 during the mounting process. Any known mounting/sealing technique in the art may be used. (e.g., heat sealing, RF welding, or a blow-fill-seal procedure).

The proximal end of the port housing 1620 is configured to rotatably attach to the activation collar 1626. In the embodiment shown in FIGS. 31A-E, the proximal end of the port housing 1620 includes a plurality of radial protrusions 1700 annularly spaced around the proximal end of the outer surface of the port housing 1620. The radial protrusions 1700 are configured to engage an annular recess 1702 on the inner surface of an outer annular skirt 1704 of the activation collar 1626, which allows rotation of the activation collar 1626 relative to the port housing 1620 but prevents axial disengagement therebetween. While a plurality of protrusions 1700 are shown, other embodiments may include a single annular flange that circumscribes the outer surface of the port housing 1620. In an embodiment where the port housing 1620 is a two-part component, the radial protrusions 1700 may be provided on the outer port housing part 1620*b* (see FIGS. 33A-E).

In the embodiment shown in FIGS. 31A-E, the radial protrusions 1700 are in the form of one-way ratchet teeth that are configured to allow rotation of the activation collar 1626 in one direction (i.e., the direction that activates the system) but prevent rotation in the opposite direction. In such an embodiment, the activation collar 1626 is provided with one or more protrusions on the inner surface of the outer annular skirt 1704 that are configured to engage the ratchet teeth 1700 during rotation such that activation of the system cannot be reversed. This may be beneficial because it prevents the first container 1602 from being backed out of (or unthreaded from) the port assembly 1606 after activation.

The outer surface of the port housing 1620 may also include a feature for attaching a protective cap. In the embodiment shown in FIGS. 31A-E, the outer surface of the port housing 1620 is provided with threads 1706 for engaging corresponding threads on the inner surface of the protective cap 1612. Other attachment mechanisms well known to those of skill in the art may also be used.

The interior of the port housing 1620 defines a cavity 1710 that is open at its proximal end. The interior surface 1711 of the cavity 1720 includes threads 1642 that are configured to engage corresponding threads 1644 on the outer surface of the retainer 1624. Accordingly, the retainer 1624 can be threaded into the port housing 1620 during activation of the system. As the retainer 1624 is threaded into the port housing 1620, the retainer 1624 moves axially in the distal direction relative to the port housing 1620. In an embodiment where the port housing 1620 is a two-part component, the threads 1642 may be provided on an interior surface 1711 of the outer port housing part 1620*b* (see FIG. 33A-E).

In order to prevent the retainer 1624 from being axially displaced without being rotated, the interior surface 1711 of the port housing 1620 includes at least one stop feature 1712, shown best in FIGS. 33A-E. As shown, the port housing 1620 includes three stop features 1712, each of which intersects the distal portion of the threads 1642. When the retainer 1624 is initially attached to the port housing 1620, each of the three threads 1644 of the retainer sits on top of a respective one of the stop features 1712 of the port housing. Thus, axial movement of the retainer 1624 is precluded. To engage the threads 1644 of the retainer 1624 with the threads 1642 of the port housing 1620, the retainer 1624 must be rotated which causes the threads 1644 of the retainer 1624 to slide off the stop features 1712 and engage the adjacent threads 1642 of the port housing 1620. This may be beneficial because it may prevent premature activation of the system. Without these stop features 1712, a user may unintentionally push the first container 1602 into the port assembly 1606 with force sufficient to cause the retainer 1624 to be displaced distally past the docking position, thereby opening the first and second containers 1602, 1604 by causing the actuator 1622 to push the stopper 1617 of the first container 1602 into the cavity 1652 of the first container and the plug 1628 to move distally at least partially into the second container 1604.

Turning back to FIGS. 31A-E, axially aligned in the cavity 1710 of the port housing 1620 is an actuator 1622 that extends in the proximal direction from a position near the distal end of the port housing 1620 and terminates at a proximal tip 1714. As shown, the actuator extends past the proximal end of the port housing 1620. In other embodiments, however, the actuator 1622 may terminate at or below the proximal end of the port housing 1620. Additionally, the actuator 1622 may extend from a position closer or further away from the distal end of the port housing 1620. In an embodiment where the port housing 1620 is a two-part component, the actuator 1622 is provided on the inner port housing part 1620*a* (see FIGS. 32A-E).

The actuator 1622 includes three support members 1716 that extend radially from a common axis. The support members 1716 and bore 1654 define the distal portion of the fluid passageway that is configured to allow fluid to be transferred between the first and second containers 1602, 1604 in order to mix the contents of the containers. As shown, the support members 1716 are attached to a distal portion of the wall 1718 of the bore 1654. In other embodiments, the support members 1716 may be attached to the wall 1718 of the bore 1654 along substantially the entire length of the bore 1654.

Figure 31A:
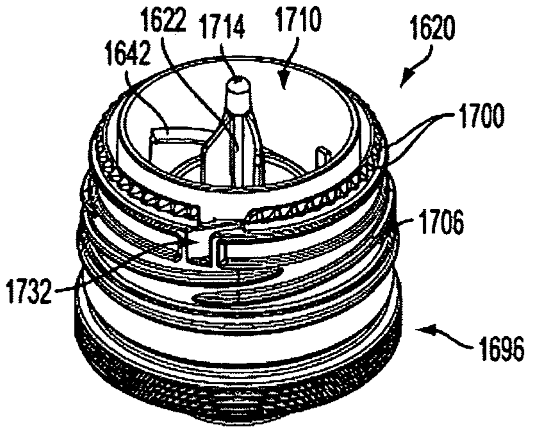
FIG. 31A is an isometric view of an exemplary port housing of the port assembly shown in FIGS. 25A-B.
Figure 31B:
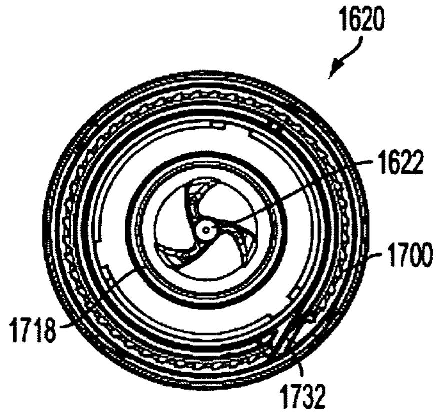
FIG. 31B is a top view of the port housing shown in FIG. 31A.
Figure 31C:
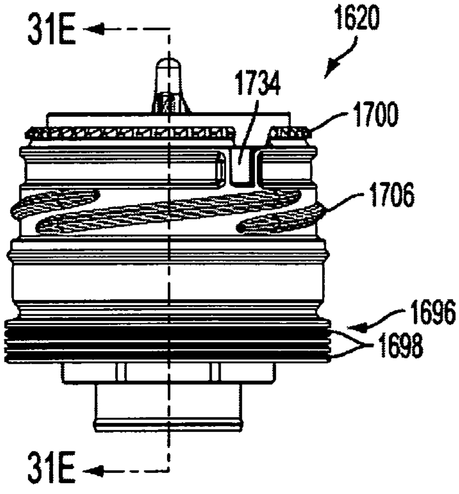
FIG. 31C is a side view of the port housing shown in FIG. 31A.
Figure 31D:
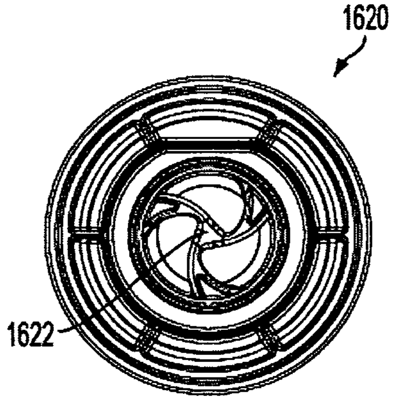
FIG. 31D is a bottom view of the port housing shown in FIG. 31A.

As shown best in FIGS. 31B and 31D, the support members 1716 are curved between the axis of the actuator 1622 and the wall 1718 of the bore 1654 to enhance the torsional rigidity of the actuator 1622. Although this embodiment has three support members 1716, the number of support members 1716 can vary as long as the support members 1716 are strong enough to withstand the axial and rotational force associated with transitioning the stopper 1617 of the first container 1602 from the first sealed position in the opening 1650 of the first container 1602 to the second unsealed position in the cavity 1652 of the first container 1602 during activation. In addition, the support members 1716 should not occlude the fluid passageway of the port assembly 1606 such that fluid cannot easily be transferred between the first and second containers 1602, 1604.

The proximal portion of each support member 1716 includes a tapered section 1724 as the support member 1716 transitions to the actuator tip 1714. This tapered section 1724 is configured to prevent interference between the flange 1662 of the stopper 1617 and the support members 1716 when the tip 1714 of the actuator 1622 forces the stopper 1617 into the cavity 1652 of the first container 1602 during activation. Without such a tapered section 1724, the flange 1662 of the stopper 1617 may become wedged between the support members 1716 and the internal surface of the neck 1658/opening 1650 of the first container 1602 when the flange 1662 folds.

Figure 31E:
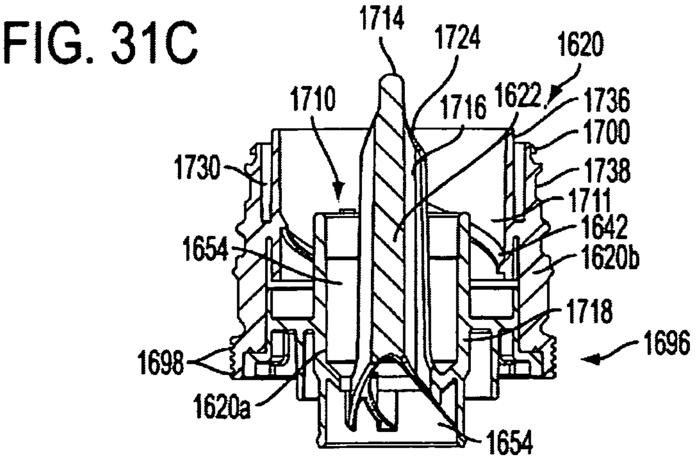
FIG. 31E is a cross-sectional view of the port housing shown in FIG. 31A.
Figure 32A:
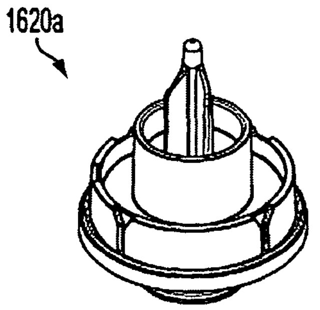
FIG. 32A is an isometric view of the inner port housing part of the port housing shown in FIGS. 31A-E.
Figure 32B:
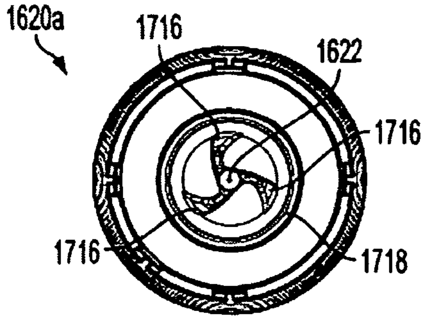
FIG. 32B is a top view of the inner port housing part shown in FIG. 32A.
Figure 32C:
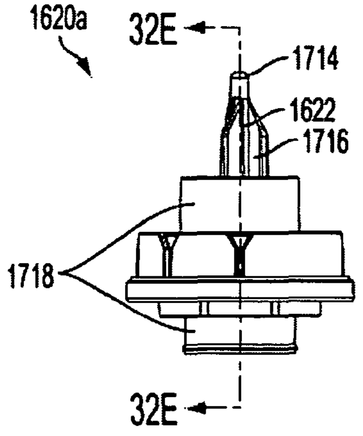
FIG. 32C is a side view of the inner port housing part shown in FIG. 32A.
Figure 32E:
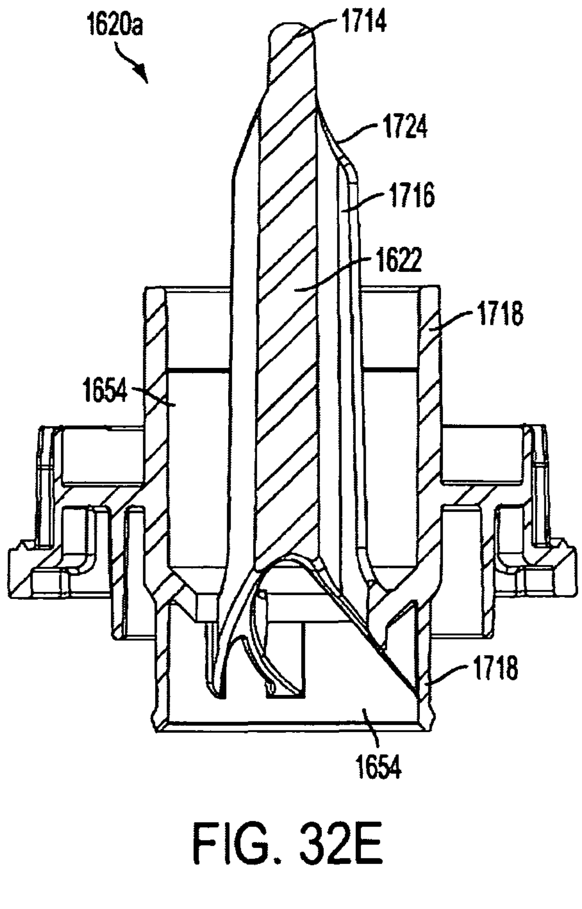
FIG. 32E is a cross-sectional view of the inner port housing part shown in FIG. 32A.
Figure 32D:
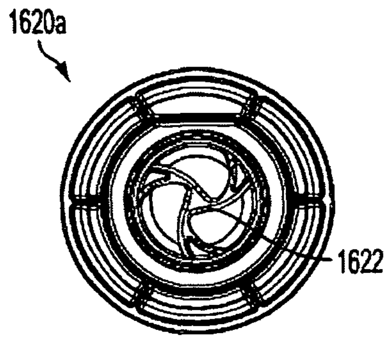
FIG. 32D is a bottom view of the inner port housing part shown in FIG. 32A.
Figure 33A:
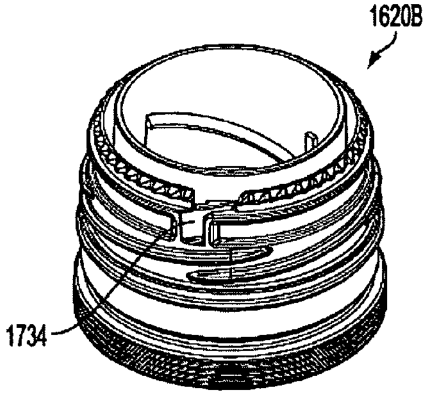
FIG. 33A is an isometric view of the outer port housing part of the port housing shown in FIGS. 31A-E.
Figure 33B:
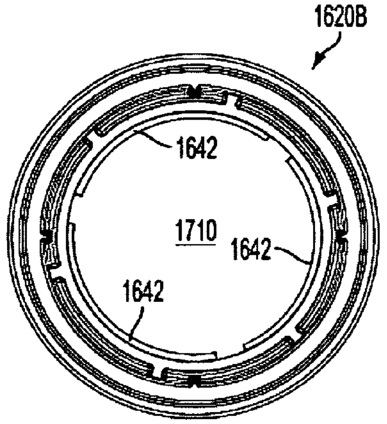
FIG. 33B is a bottom view of the outer port housing part shown in FIG. 33A.
Figure 33C:
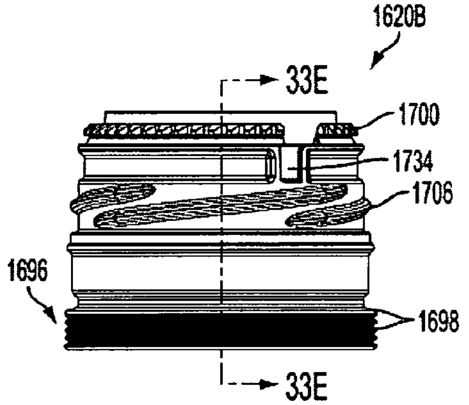
FIG. 33C is a side view of the outer port housing part shown in FIG. 33A.
Figure 33D:
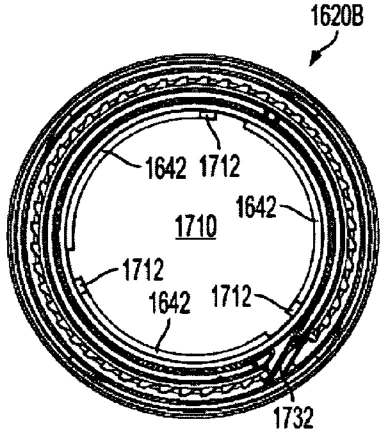
FIG. 33D is a top view of the outer port housing part shown in FIG. 33A.
Figure 33E:
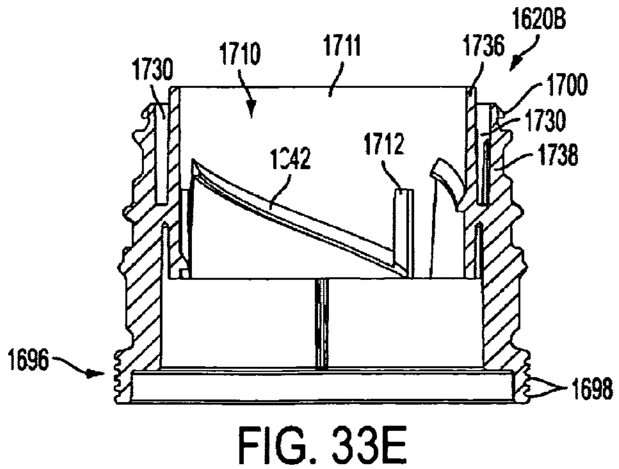
FIG. 33E is a cross-sectional view of the outer port housing part shown in FIG. 33A.
Figure 34A:
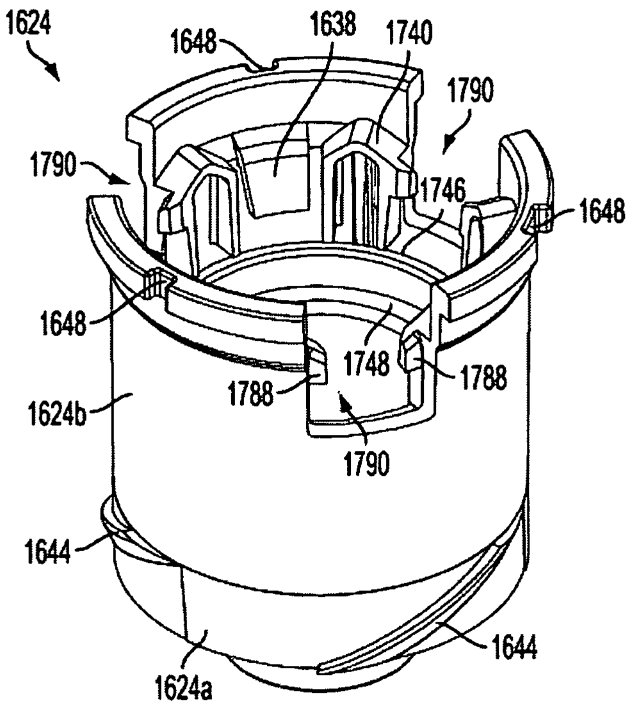
FIG. 34A is an isometric view of an exemplary retainer of the port assembly shown in FIGS. 25A-B.
Figure 34B:
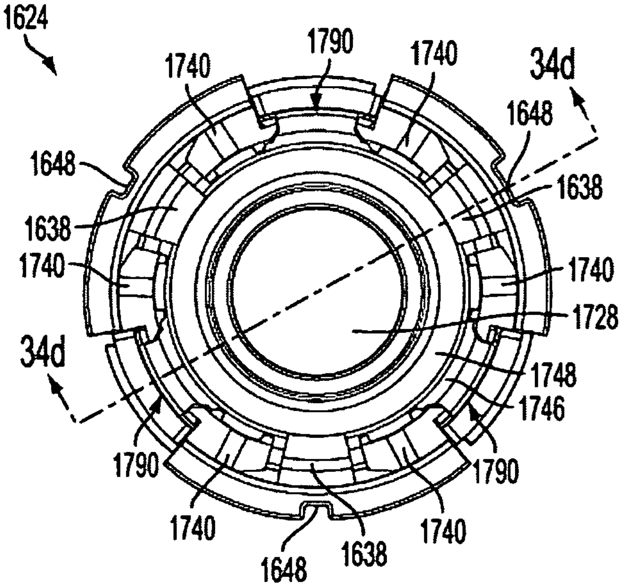
FIG. 34B is a top view of the retainer shown in FIG. 34A.
Figure 34C:
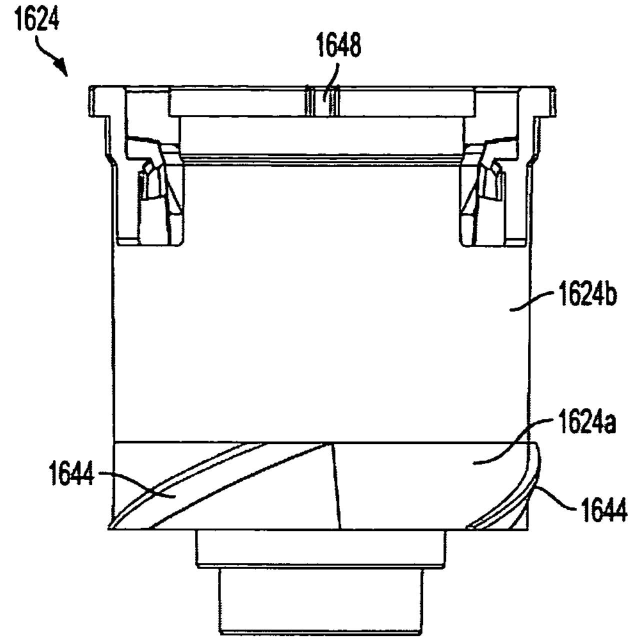
FIG. 34C is a side view of the retainer shown in FIG. 34A.
Figure 34D:
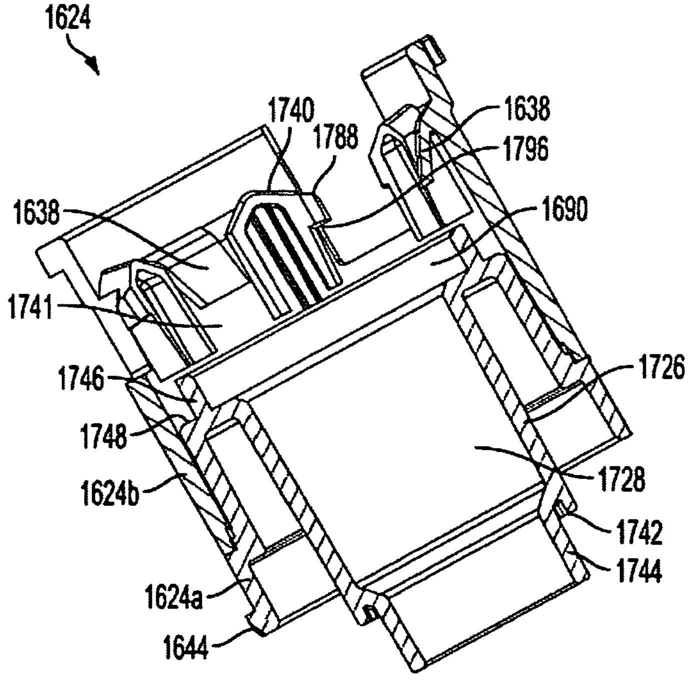
FIG. 34D is a cross-sectional view of the retainer shown in FIG. 34A.
Figure 35A:
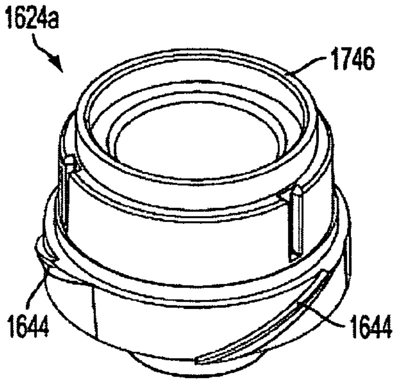
FIG. 35A is an isometric view of the inner retainer part of the retainer shown in FIGS. 34A-D.
Figure 35B:
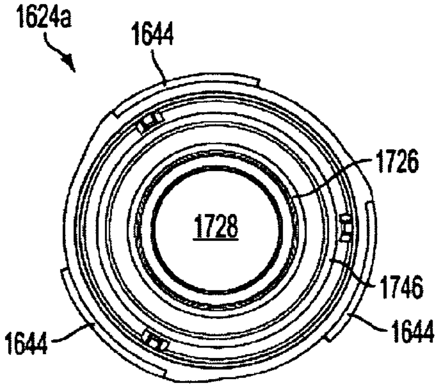
FIG. 35B is a top view of the inner retainer part shown in FIG. 35A.
Figure 35C:
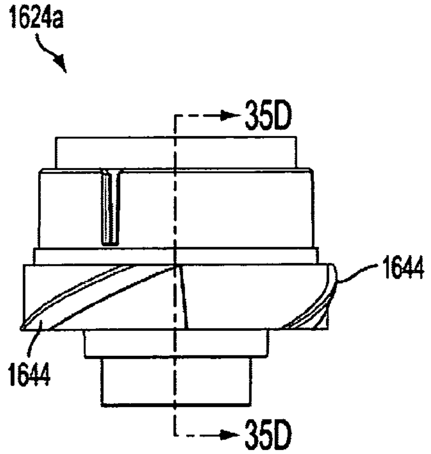
FIG. 35C is a side view of the inner retainer part shown in FIG. 35A.
Figure 35D:
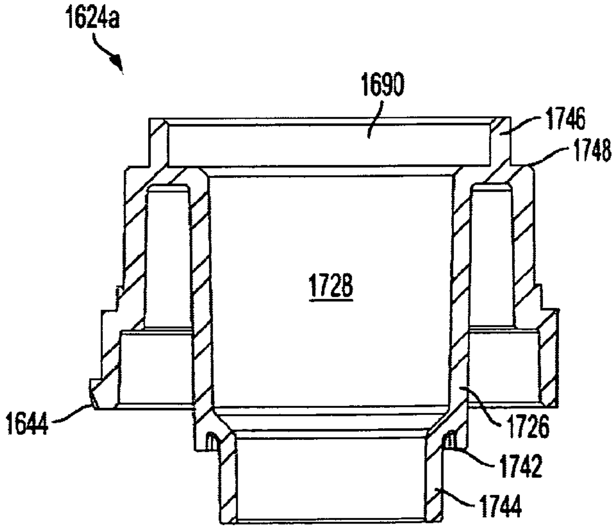
FIG. 35D is a cross-sectional view of the inner retainer part shown in FIG. 35A.
Figure 36A:
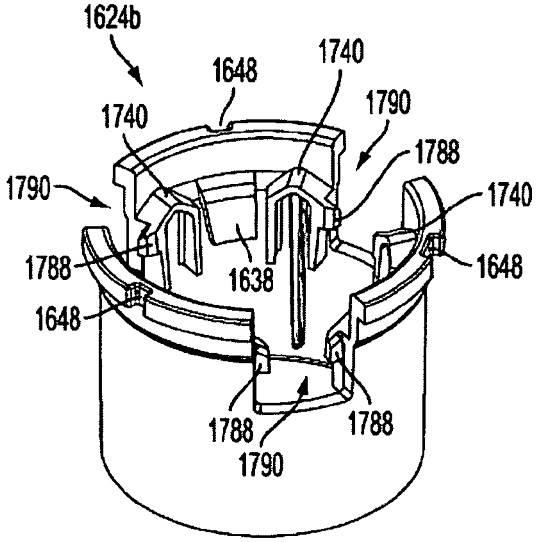
Figure 36B:
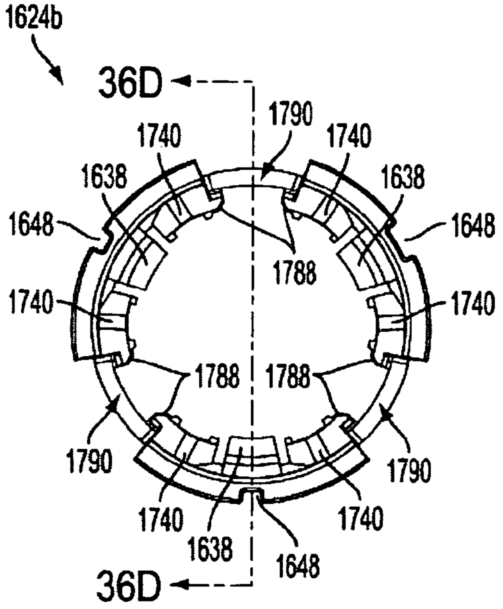
Figure 36C:
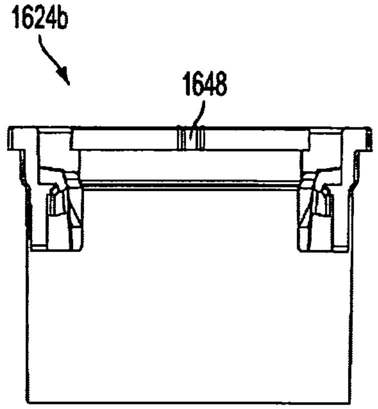
Figure 36D:
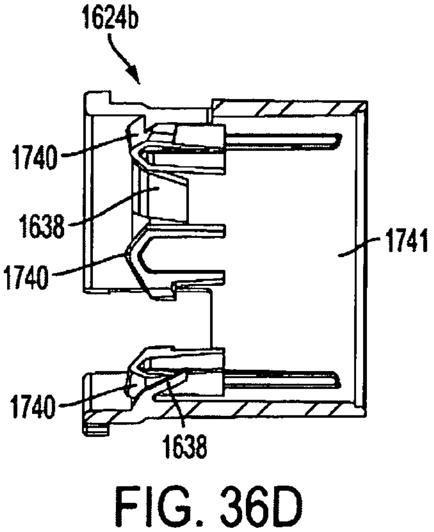
Figure 37A:
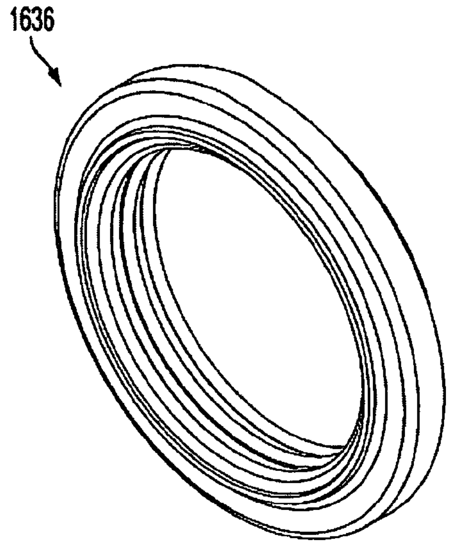
Figure 37B:
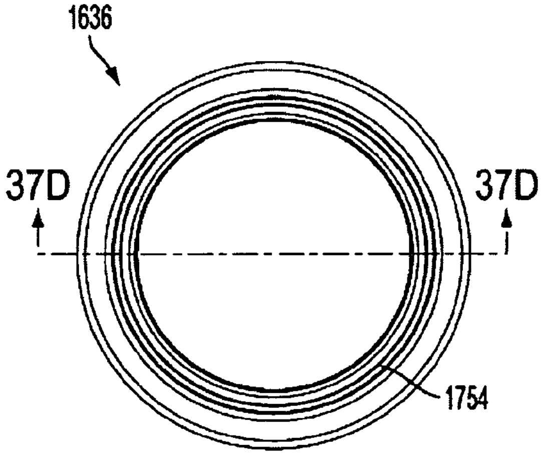
Figure 37C:
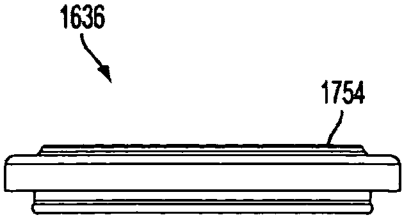
Figure 37D:
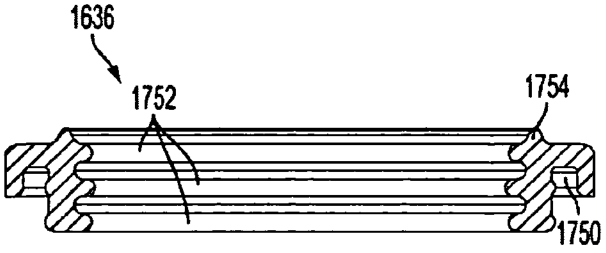

As shown best in FIG. 31E, the proximal portion of the port housing 1620 includes a circumferential guide slot 1730 that is configured to house a hanger 1630 prior to activation and to guide the hanger 1630 out of an exit slot 1732 of the port housing 1620 during activation. To facilitate the transition of the hanger 1630 from the non-activated, non-hanging position in the slot 1730, to the activated hanging position outside the slot 1730, an angular surface 1734 is provided that connects the inner lip 1736 of the port housing 1620 to the outer lip 1738 of the port housing 1620. The angular surface 1734 is configured to force the hanger 1630 out of the exit slot 1732 upon rotation of the activation collar 1626 relative to the port housing 1620 so that it is presented to the user and operable for hanging the system 1600 after activation. Accordingly, in this embodiment, the hanger is only operable when fluid communication is established between the first and second containers 1602, 1604.

The guide slot 1730 is also configured to receive the guide tabs 1764 of the activation collar 1626, as shown in FIGS. 26 and 27. This tab-slot engagement helps maintain axial alignment between the activation collar 1626 and the port housing 1620 and ensures smooth rotation of the activation collar 1626 relative to the port housing 1620 during activation.

Turning now to the retainer 1624 shown in FIGS. 34A-D, the retainer 1624 is configured to receive and dock the first container 1602. To dock the first container 1602, the retainer 1624 includes a plurality of resilient retention tabs 1638, each configured to engage one of the protrusions 1640 of the first container 1602 when the first container 1602 is inserted into the port assembly 1606. As shown, the tabs 1638 extend distally and radially inward from a proximal portion of the retainer 1624. Shown best in FIG. 34B, there are three tabs 1638 equally spaced around the axis of the retainer 1624; however, any number of tabs 1638 can be used as long as they are capable of securing the first container 1602 to the port assembly 1606 and preventing disengagement. In an embodiment where the retainer 1624 is a two-part component, the tabs 1638 may be provided on the outer retainer part 1624*b* (see FIGS. 36A-D).

The tabs 1638 should be constructed of a material that allows the tabs 1638 to flex inward when the first container 1602 is inserted into the port assembly 1606, and to thereafter allow the tabs 1638 to spring back to their original positions once the protrusions 1640 of the first container 1602 pass the distal end of the tabs 1638, thereby securely docking the first container 1602 to the port assembly 1606. The tabs 1638 allow the first container 1602 to be inserted into the port assembly 1606 but prevent removal of the first container 1602 after the first container 1602 is in the docked position. By preventing removal of the first container 1602 from the port assembly 1606, drug tampering, contamination, and accidental discharge of the contents is prevented.

The tabs 1638 of the retainer 1624 are axially positioned such that the first container 1602 can be docked to the port assembly 1606 without opening the first container 1602. This may be beneficial because it allows the first container 1602 to be docked to the second container 1604 (via the port assembly 1606) without exposing the contents of the first container 1602 to the outside environment. Thus, the shelf life of the first container's contents is not compromised. Moreover, this configuration may allow the first container 1602 to be selected and docked to the rest of the system by, for example, a pharmacist, and then transported to the location of the patient for activation and subsequent delivery by, for example, a nurse.

When the first container 1602 is docked to the port assembly 1606, the actuator tip 1714 is positioned below the stopper 1617, or in some embodiments such as the one shown is FIG. 26, the actuator 1714 tip may abut the stopper without dislodging it from its sealed position in the opening 1650 of the vial 1616.

The retainer 1624 is also be provided with alignment features 1740 that align the protrusions 1640 on the body cap 1608 of the first container 1602 with the tabs 1638 and openings 1790 of the retainer 1624. This ensures that the tabs 1638 properly engage the protrusions 1640 during docking. As shown best in FIG. 34D, the alignment features 1740 extend radially inward from an inner surface 1741 of the retainer 1624 and each include two angled surfaces at their proximal end. The angled surfaces of two adjacent guide features 1740 guide the protrusions 1640 to the correct locations during docking of the first container 1602 to the retainer 1624.

The retainer 1624 includes a bore 1728 that defines the proximal portion of the fluid passageway of the port assembly 1606. As shown in FIGS. 26-27, the inner diameter of the retainer bore wall 1726 is greater than the diameter of the actuator 1622 in order to allow the retainer 1624 to move distally about the actuator 1622 during activation. The outer diameter of the retainer bore wall 1726 is less than the inner diameter of the port housing bore wall 1718 in order to allow the retainer 1624 to move distally within the port housing 1620 during activation.

The outer surface of the retainer bore wall 1726 is provided with a step 1742 that serves as a proximal stop for the seal 1634 that circumscribes the smaller diameter portion 1744 of the bore wall 1726. The step 1742 prevents the seal 1634 from moving in the proximal direction as the retainer 1624 moves in the distal direction into the port housing 1620 during activation. As noted above, the seal 1634 is configured to seal the portion of the fluid passageway defined by the bore 1728 of the retainer 1624 to the portion of the fluid passageway defined by the bore 1654 of the port housing 1620 in order to prevent fluid from escaping the fluid passageway during use. As shown in FIGS. 26-27, the seal 1634 is located between the outer surface of the retainer bore wall 1726 and the inner surface of the port housing bore wall 1718.

Below the tabs 1638, the retainer 1624 includes an annular lip 1746 that extends proximally from a proximal facing surface 1748 in the cavity of the retainer 1624. The lip 1746 is configured to engage an annular groove 1750 in the seal 1636, which is configured to seal the first container 1602 to the retainer 1624 during docking and before activation of the system. The seal 1636 may be fixed to the retainer 1624 using any known technique in the art.

In one embodiment of the seal 1636 shown in FIGS. 37A-37D, the seal 1636 includes a plurality of circumferential sealing surfaces that are configured to seal against the radially-facing sealing surface 1684 of the body cap 1608 of the first container 1602. These sealing surfaces may be provided as three inwardly extending radial ribs 1752. However, during use, all three ribs 1752 may not actually provide a seal, rather, only one or two of the ribs 1752 may actually abut and seal against the body cap 1608 of the first container 1602. Moreover, any number of radial ribs 1752 may be used. In addition to the radial ribs 1752, the seal 1636 includes an axial rib 1754 that is configured to seal against the axially-facing sealing surface 1686 of the body cap 1608 of the first container 1602. Any number of axial ribs 1752 may be used. During use, however, the axial rib 1754 may not actually seal against the axially-facing sealing surface 1686 due to proximal "spring back" of the first container 1602 after it passes the distal end of the tabs 1638.

Turning back to the retainer 1624 shown in FIGS. 34A-D, the outer surface of the retainer 1624 includes threads 1644 that, as noted above, are complimentary to the internal threads 1642 of the port housing 1620. The threads 1644 allow the retainer 1624 to be threaded into the port housing 1620 during activation of the system. The retainer 1624 has three threads 1644, each configured to engage one of the corresponding threads 1642 of the port housing 1620. In other embodiments, the number of threads 1642, 1644 may vary. As shown best in FIG. 34C, the threads 1644 only span a distal portion of the outer surface of the retainer 1624 but in other embodiments they may span more of the length of the retainer. In an embodiment where the retainer 1624 is a two-part component, the threads 1644 may be located on the distal portion of the inner retainer part 1624*a* (see FIGS. 35A-D).

The retainer 1624 also includes three notches 1648 at its proximal end that are equally spaced around the axis of the retainer 1624 and are configured to engage three corresponding splines 1646 on the internal surface of the activation collar 1626. Engagement between notches 1648 and splines 1646 allows the retainer 1624 to fixedly rotate with the activation collar 1626. In particular, as the activation collar 1626 is rotated relative to the port housing 1620, the engagement between the splines 1646 of the collar 1626 and notches 1648 of the retainer 1624 causes the retainer 1624 to rotate. In turn, this rotation causes the retainer 1624 to be threaded into the port housing 1620. As the retainer 1624 is threaded into the port housing 1620, the notches 1648 of the retainer 1624 slide distally along the splines 1646 of the activation collar 1626.

As the retainer 1624 moves axially in the distal direction relative to the port housing 1620, the axially fixed actuator 1622 forces the stopper 1617 of the first container 1602 into the cavity 1652 of the first container 1602. In other embodiments, the same functional relationship between the retainer 1624 and activation collar 1626 may be achieved by providing the outer surface of the retainer 1624 with spline-like features and the inner surface of the activation collar 1626 with notches/grooves.

As shown in FIG. 27, to prevent the retainer 1624 from moving too far in the distal direction after activation, the proximal end of the bore wall 1718 of the port housing 1620 is positioned such that after activation the proximal end of the bore wall 1718 contacts or is in close proximity to a distally facing surface 1649 of the retainer 1624. Accordingly, the retainer 1624 cannot move any further in the distal direction.

In an embodiment where the port assembly 1606 does not include a seal 1636 in the cavity of the retainer 1624, for example, when the body cap 1608 of the first container 1602 is provided with a radial sealing bead 1688 as described above, the radially facing surface 1690 of the annular lip 1746 may provide a sealing surface for the sealing bead 1688. In such an embodiment, the radial sealing bead 1688 of the first container 1602 abuts and seals against the radially-facing sealing surface 1690 when the first container 1602 is docked to the port assembly 1606, prior to activation.

Turning to the activation collar 1626 shown in FIGS. 38A-E, the activation collar 1626 is generally cylindrical. The outer surface of the activation collar 1626 is provided with ribs/ridges 1756 so that a user can easily grip and rotate the activation collar 1626 in order to activate the system. In other embodiments, the outer surface of the activation collar 1626 may be smooth, provided with depressions/dimples or bumps instead of ribs 1756, or may simply be provided with a surface finish that enhances the friction between the activation collar 1626 and user's hands. The diameter of the proximal opening 1758 of the activation collar 1626 is larger than the outside diameter of the first container 1602 so that the first container 1602 can be inserted through the proximal opening 1758 and docked to the retainer 1624 of the port assembly 1606. When assembled as shown in FIGS. 26-27, the collar 1626 circumscribes the retainer 1624.

The inner surface of the activation collar 1626 includes splines 1646 that are configured to slidably engage corresponding notches 1648 in the outer surface of the proximal end of the retainer 1624. As shown, the activation collar 1626 includes three splines 1646. Although three splines 1646 are shown, any number of splines 1646 and corresponding notches 1648 are possible as long as rotation of the activation collar 1626 can be translated into rotation of the retainer 1624 and the notches 1648 of the retainer 1624 are free slide axially along the splines 1646.

As noted above, the distal end of the activation collar 1626 is configured to rotatably attach to the port housing 1620. As shown best in FIGS. 26-27 and 38A, the distal end of the activation collar 1626 includes two distally extending annular skirts 1704, 1764 that define an annular channel 1762 that is configured to receive the outer annular lip 1738 of the port housing 1620. The outer annular skirt 1704 of the collar 1626 includes a radial groove (or recess) 1702 that is configured to receive the one-way ratchet teeth 1700 at the proximal end of the outer annular lip 1738 of the port housing 1620. The groove 1702 axially engages the one-way ratchet teeth 1700 of the port housing 1620 in a snap-fit manner, which allows rotation but prevents axial disengagement between the activation collar 1626 and the port housing 1620.

As shown best in FIG. 38E, the distal portion of the inner annular skirt 1764 of the activation collar 1626 includes a plurality of guide tabs that are configured to engage the annular slot 1730 at the proximal end of the port housing 1620. This tab-slot engagement helps maintain axial alignment between the activation collar 1626 and the port housing 1620 and ensures smooth rotation of the activation collar 1626 relative to the port housing 1620.

The outer surface of the activation collar 1626 is also provided with a region 1766 for the hanger 1630 to rest in its non-activated non-hanging position. This hanger region 1766 is void of any ridges/ribs 1756. A male snap feature 1768 is provided near the distal end of the hanger region 1766 to temporarily hold the hanger 1630 against the outer surface of the activation collar 1626 prior to activation. The male snap feature 1768 is configured to engage a female snap recess 1770 on the backside of the hanger 1630 (see FIG. 39D).

The hanger 1630 may be provided as a separate part that is attached to the activation collar 1626 or may be molded as an integral part of the activation collar 1626 with a living hinge. As shown best in FIG. 27, the hanger 1630 is configured so that it can swing away from the activation collar 1626 for use. As shown in FIGS. 39A and 39C-D, the hanger 1630 includes a through-hole 1772 for conveniently hanging the system on an appropriate device (e.g., pole, rack or stand).

When the port assembly 1606 is in the non-activated non-hanging condition shown in FIG. 26, the hanger 1630 is not accessible to the user. Upon activation of the system, the hanger 1630 transitions from the non-activated non-hanging condition to an activated hanging condition in which the hanger 1630 is presented to the user, as shown in FIG. 27. In one embodiment, the release of the hanger 1630 and the establishment of fluid communication occur simultaneously. Accordingly, the hanger is only operable when fluid communication has been established between the first and the second containers.

As explained above with reference to FIGS. 31A-E, the circumferential guide slot 1730 near the proximal end of the port housing 1620 includes an exit slot 1732 that is defined by the angled surface 1734 and the outer annular lip 1738 of the port housing 1620. Prior to activation, the distal tab 1774 (shown in FIGS. 39A and 39C-D) of the hanger 1630 is positioned in the guide slot 1730 of the port housing 1620. As the activation collar 1626 is rotated in order to activate the system, the tab 1774 of the hanger 1630 slides within the guide slot 1730 until it contacts the angled surface 1734 of the port housing 1620 which disengages the male snap feature 1768 of the collar 1626 from the female snap feature 1770 of the hanger 1630 and forces the hanger 1630 out of exit slot 1732 of the guide slot 1730. The amount of rotation needed to transition the hanger 1630 from the non-activated non-hanging position to the activated hanging position and to activate the system may vary, and in particular may be between about 120-200 degrees.

In an embodiment where the hanger 1630 is a separate component that is attached to the activation collar 1626, as shown in FIGS. 39A-D, the hanger 1630 may include a living hinge 1776 between a main body 1778 of the hanger 1630 and the hanger attachment feature 1780. As shown best in FIGS. 39A-B, the hanger attachment feature 1780 is provided with two holes 1782 for receiving two posts 1784 of the activation collar 1626. The posts 1784 of the activation collar 1626 may be attached to the holes 1782 of the hanger 1630 using any known connection mechanism in the art (e.g., ultrasonic welding).

As noted above, the port assembly 1606 described with respect to FIGS. 25A-40B, may also be provided with a locking mechanism that prevents inadvertent rotation between the activation collar 1626 and the port housing 1620, thereby preventing premature activation of the system 1600. In one embodiment, the locking mechanism includes locking elements on both the activation collar 1626 (e.g., a first locking element) and retainer 1624 (e.g., a second locking element) that cooperate with each other to prevent rotational and axial movement of the collar 1626 and retainer 1624 relative to the port housing 1620. As shown in the embodiment of FIGS. 38A-E, the first locking element on the activation collar 1626 includes three locking tabs 1786 that extend distally and radially inwardly and are configured to engage the second locking element of the retainer which includes the locking protrusions 1788 (see FIGS. 34A-D) in the openings 1790 of the retainer 1624. This engagement is present prior to the first container 1602 being inserted into and docked to the retainer 1624. More specifically, each of the three locking tabs 1786 includes two wings 1792, each wing 1792 having a step 1794 configured to engage the distal end 1796 (see FIG. 34D) of a respective one of the locking protrusions 1788 on the retainer 1624.

When the locking tabs 1786 are engaged with the locking protrusions 1788 via the steps 1794 of the wings 1792, the activation collar 1626 and the retainer 1624 are prevented from rotating relative to the port housing 1620 because the retainer 1624 cannot move axially due to the distal ends 1796 of the locking protrusions 1788 being engaged with the steps 1794 of the wings 1792 of the locking tabs 1786. In other words, as a user tries to rotate the activation collar 1626, the retainer 1624 cannot be threaded into the port housing 1620 because the retainer 1624 cannot move axially. Engagement between the locking protrusions 1788 and steps 1794 of the wings 1792 is shown best in FIGS. 40A-B.

To unlock the locking mechanism, the locking tabs 1786 must be forced radially outward, thereby releasing engagement between the locking tabs 1786 of the collar 1626 and the locking protrusions 1788 of the retainer 1624. To accomplish this, a user simply inserts and connects the first container 1602 to the port assembly 1606. As the first container 1602 is inserted into the port assembly 1606, the alignment features 1740 of the retainer 1624 align the docking protrusions 1640 with the retention tabs 1638 of the retainer 1624 and the unlocking protrusions 1640 with the locking tabs 1786 of the retainer 1624. Accordingly, as the first container 1602 enters the port assembly 1606, three of the protrusions ("unlocking protrusions") 1640 on the body cap 1608 contact the three locking tabs 1786 of the collar 1626 and force the locking tabs 1786 radially outward which unlocks the port assembly 1606. At substantially the same time, the other three protrusions ("docking protrusions") 1640 engage the retention tabs 1638 of the retainer 1624, thereby docking the first container 1602 to the port assembly 1606. In such an embodiment, the three unlocking protrusions 1640 and the three docking protrusions 1640 alternate around the body cap 1608 as dictated by the configuration of the retainer 1624 shown in FIGS. 34A-D.

Other locking mechanisms may be used, including, for example, the ones shown and described above with reference to FIGS. 12A-14C.

Several alternative embodiments and examples have been described and illustrated herein. A person of ordinary skill in the art will further appreciate that any of the embodiments could be provided in any combination with the other embodiments disclosed herein. Additionally, the terms "first," "second," "third," etc. as used herein are intended for illustrative purposes only and do not limit the embodiments in any way. Further, the term "plurality" as used herein indicates any number greater than one, either disjunctively or conjunctively, as necessary, up to an infinite number. Additionally, the term "having" as used herein in both the disclosure and claims, is utilized in an open-ended manner.

A person of ordinary skill in the art will understand that the invention may be embodied in other forms without departing from the spirit or central characteristics thereof. The present examples and embodiments are to be considered in all respects as illustrative and not restrictive, and the invention is not to be limited to the details given herein. Accordingly, while specific embodiments have been illustrated and described, numerous modifications and/or combinations may be made to these embodiments without departing from the spirit of the invention and the scope of protection, which is only limited by the scope of the accompanying claims.

The invention claimed is:

1. A system for mixing the contents of a first container and a second container, the system comprising:

a first container comprising an opening to a cavity containing a first substance, and a stopper sealing the opening;

a second container having a cavity containing a second substance; and a port assembly comprising (i) a port housing connected to the second container, (ii) a retainer for connecting to the first container, the retainer configured to rotate relative to the port housing, wherein rotation of the retainer relative to the port housing places the first container and the second container in fluid communication, (iii) an actuator configured to force the stopper of the first container into the cavity of the first container during rotation of the retainer relative to the port housing, and (iv) a locking mechanism that prevents rotation of the retainer relative to the port housing when the first container is not connected to the retainer, wherein the first container comprises at least one unlocking member configured to unlock the locking mechanism, wherein the at least one unlocking member comprises a protrusion extending radially from the first container.

2. The system of claim 1, wherein a first set of threads is formed on a surface of the port housing and wherein a second set of threads is formed on a surface of the retainer, the first and second sets of threads constructed to rotationally engage and move the retainer axially relative to the port housing upon rotation of the retainer relative to the port housing.

3. The system of claim 1, the port assembly further comprising a collar that is rotationally fixed to the retainer, wherein the collar comprises a first locking element and the retainer comprises a second locking element that engages the first locking element to prevent rotation of the collar and retainer relative to the port housing when the first container is not connected to the retainer.

4. The system of claim 3, wherein engagement of the first locking element and the second locking element prevents axial movement of the retainer relative to the collar and the port housing when the first container is not connected to the retainer.

5. The system of claim 3, wherein the collar circumscribes the retainer, the first locking element comprises a tab extending radially inwardly from the collar, the second locking element comprises a protrusion, and wherein the tab of the first locking element is constructed to engage the protrusion of the second locking element to prevent rotation of the collar and retainer relative to the port housing when the first container is not connected to the retainer.

6. The system of claim 1, wherein the first container comprises a vial with body cap, wherein the body cap comprises the unlocking member.

7. The system of claim 1, wherein the first container further comprises at least one axial locking member for irreversibly connecting the first container to the retainer.

8. The system of claim 6, wherein the body cap further comprises at least one axial locking member for irreversibly connecting the first container to the retainer.

9. A system for mixing the contents of a first container and a second container, the system comprising:

a first container comprising (i) an opening to a cavity containing a first substance, (ii) a stopper sealing the opening, (iii) at least one axial locking member, and (iv) at least one unlocking member, wherein the at least one unlocking member comprises a protrusion extending radially from the first container, and a second container containing a second substance, wherein the second container comprises a port assembly comprising a port housing and a main body, the main body configured to receive the first container and to rotate relative to the port housing, wherein rotation of the main body relative to the port housing places the first container and the second container in fluid communication, wherein the main body comprises at least one retention tab constructed to engage the at least one axial locking member of the first container to prevent axial removal of the first container from the main body after the first container has been connected to the main body, and wherein the main body further comprises a locking mechanism constructed to prevent rotation of the main body relative to the port housing when the first container is not connected to the main body, wherein the at least one unlocking member of the first container is constructed to unlock the locking mechanism when the first container is connected to the main body.

10. The system of claim 9, wherein the port housing further comprises a seal that prevents fluid communication between the first container and the second container prior to rotation of the main body relative to the port housing.

11. The system of claim 9, wherein the main body further comprises a collar and a retainer comprising the at least one retention tab, wherein the collar and retainer are rotationally fixed and wherein the collar comprises a first locking element of the unlocking mechanism and the retainer comprises a second locking element of the locking mechanism that cooperates with the first locking element to prevent rotation of the main body relative to the port housing.

12. The system of claim 11, wherein a first set of threads is formed on a surface of the port housing and wherein a second set of threads is formed on a surface of the retainer, the first and second sets of threads constructed to rotationally engage and move the retainer axially relative to the port housing upon rotation of the main body relative to the port housing.

13. The system of claim 10, wherein the seal is a plug member constructed to move axially relative to the port housing when the main body rotates relative to the port housing.

14. The system of claim 10, wherein the seal is a septum or film.

15. A medicament container comprising:

an opening to a cavity containing a first substance;

a stopper sealing the opening;

at least one axial locking member, wherein the at least one axial locking member is configured to prevent axial removal of the medicament container from a port assembly of a second container after the medicament container is connected to a port assembly of a second container; via engagement of the at least one axial locking member of the medicament container and a retainer of a port assembly of a second container; and at least one unlocking member, wherein the at least one unlocking member comprises a protrusion extending radially from the medicament container, wherein the at least one unlocking member is configured to unlock a rotational locking mechanism associated with a port assembly of a second container when the medicament container is connected to a port assembly of a second container, thereby allowing a retainer of a port assembly of a second container to rotate relative to a port housing of a port assembly of a second container, which places the medicament container and a second container in fluid communication.

16. The medicament container of claim 15, wherein the at least one axial locking member comprises a protrusion extending radially from the medicament container.

17. The medicament container of claim 15, wherein the stopper is configured to be forced into the cavity of the medicament container when the medicament container is connected to a port assembly of a second container.

18. The medicament container of claim 15, wherein the at least one axial locking member comprises at least two axial locking members.

19. The medicament container of claim 15, wherein the at least one unlocking member comprises at least two unlocking members.

* * * * *